United States Patent
Maerkl et al.

(10) Patent No.: US 7,143,785 B2
(45) Date of Patent: Dec. 5, 2006

(54) MICROFLUIDIC LARGE SCALE INTEGRATION

(75) Inventors: Sebastian J. Maerkl, Pasadena, CA (US); Todd A. Thorsen, Arlington, MA (US); Xiaoyan Bao, Pasadena, CA (US); Stephen R. Quake, San Marino, CA (US); Vincent Studer, Paris (FR)

(73) Assignee: California Institute of Technology, Pasadena, CA (US)

( * ) Notice: Subject to any disclaimer, the term of this patent is extended or adjusted under 35 U.S.C. 154(b) by 248 days.

(21) Appl. No.: 10/670,997

(22) Filed: Sep. 24, 2003

(65) Prior Publication Data

US 2004/0112442 A1 Jun. 17, 2004

Related U.S. Application Data

(60) Provisional application No. 60/413,860, filed on Sep. 25, 2002.

(51) Int. Cl.
*F16K 11/20* (2006.01)
*F16K 7/00* (2006.01)

(52) U.S. Cl. .................. 137/597; 251/28; 251/61.1

(58) Field of Classification Search ............... 137/597; 251/28, 61.1
See application file for complete search history.

(56) References Cited

U.S. PATENT DOCUMENTS

| | | | |
|---|---|---|---|
| 3,570,515 A | 3/1971 | Kinner | |
| 3,599,525 A * | 8/1971 | Klann | 137/594 |
| 3,747,628 A | 7/1973 | Holster et al. | |
| 4,046,159 A | 9/1977 | Pegourie | |
| 4,119,368 A | 10/1978 | Yamazaki | |
| 4,153,855 A | 5/1979 | Feingold | |
| 4,245,673 A | 1/1981 | Bouteille et al. | |
| 4,250,929 A * | 2/1981 | Andreev et al. | 137/607 |
| 4,434,704 A | 3/1984 | Surjaatmadja | |
| 4,898,582 A | 2/1990 | Faste | |
| 4,992,312 A | 2/1991 | Frisch | |
| 5,085,562 A | 2/1992 | Van Lintel | |
| 5,088,515 A | 2/1992 | Kamen | |

(Continued)

FOREIGN PATENT DOCUMENTS

EP 0 592 094 A2 4/1994

(Continued)

OTHER PUBLICATIONS

Unger M A et al. : "Monolithic Microfabricated Valves and Pumps by Multilayer Soft Lithography" Science, American Association for the Advancement of Science, US, vol. 288, Apr. 7, 2000, pp. 113-116, XP002192277 ISSN: 0036-8075.

(Continued)

*Primary Examiner*—Stephen M. Hepperle
(74) *Attorney, Agent, or Firm*—Townsend and Townsend and Crew LLP

(57) ABSTRACT

High-density microfluidic chips contain plumbing networks with thousands of micromechanical valves and hundreds of individually addressable chambers. These fluidic devices are analogous to electronic integrated circuits fabricated using large scale integration (LSI). A component of these networks is the fluidic multiplexor, which is a combinatorial array of binary valve patterns that exponentially increases the processing power of a network by allowing complex fluid manipulations with a minimal number of inputs. These integrated microfluidic networks can be used to construct a variety of highly complex microfluidic devices, for example the microfluidic analog of a comparator array, and a microfluidic memory storage device resembling electronic random access memories.

21 Claims, 42 Drawing Sheets

U.S. PATENT DOCUMENTS

| | | | |
|---|---|---|---|
| 5,096,388 A | 3/1992 | Weinberg | |
| 5,126,115 A | 6/1992 | Fujita et al. | |
| 5,164,558 A | 11/1992 | Huff et al. | |
| 5,171,132 A | 12/1992 | Miyazaki | |
| 5,224,843 A | 7/1993 | Van Lintel | |
| 5,259,737 A | 11/1993 | Kamisuki et al. | |
| 5,265,327 A | 11/1993 | Faris et al. | |
| 5,290,240 A | 3/1994 | Horres, Jr. | |
| 5,336,062 A | 8/1994 | Richter | |
| 5,346,372 A | 9/1994 | Naruse et al. | |
| 5,375,979 A | 12/1994 | Trah | |
| 5,376,252 A | 12/1994 | Ekstrom | |
| 5,400,741 A | 3/1995 | DeTitta et al. | |
| 5,423,287 A | 6/1995 | Usami et al. | |
| 5,529,465 A | 6/1996 | Zengerle et al. | |
| 5,593,130 A | 1/1997 | Hansson et al. | |
| 5,642,015 A | 6/1997 | Whitehead et al. | |
| 5,659,171 A | 8/1997 | Young et al. | |
| 5,660,370 A | 8/1997 | Webster | |
| 5,681,024 A * | 10/1997 | Lisec et al. | 251/11 |
| 5,705,018 A | 1/1998 | Hartley | |
| 5,759,014 A | 6/1998 | Van Lintel | |
| 5,775,371 A * | 7/1998 | Pan et al. | 137/597 |
| 5,788,468 A | 8/1998 | Dewa et al. | |
| 5,836,750 A | 11/1998 | Cabuz | |
| 5,842,787 A | 12/1998 | Kopf-Sill et al. | |
| 5,875,817 A | 3/1999 | Carter | |
| 5,876,187 A | 3/1999 | Forster et al. | |
| 5,932,799 A | 8/1999 | Moles | |
| 5,942,443 A | 8/1999 | Parce et al. | |
| 6,007,309 A | 12/1999 | Hartley | |
| 6,043,080 A | 3/2000 | Lipshutz et al. | |
| 6,102,068 A * | 8/2000 | Higdon et al. | 137/341 |
| 6,123,769 A | 9/2000 | Sanjoh | |
| 6,155,282 A | 12/2000 | Zachary et al. | |
| 6,174,365 B1 | 1/2001 | Sanjoh | |
| 6,202,687 B1 * | 3/2001 | Park | 137/597 |
| 6,296,673 B1 | 10/2001 | Santarsiero et al. | |
| 6,345,502 B1 | 2/2002 | Tai et al. | |
| 6,408,878 B1 * | 6/2002 | Unger et al. | 137/597 |
| 6,409,832 B1 | 6/2002 | Weigl et al. | |
| 6,767,706 B1 | 7/2004 | Quake et al. | |
| 2001/0027745 A1 | 10/2001 | Weigl et al. | |

FOREIGN PATENT DOCUMENTS

| | | |
|---|---|---|
| EP | 0 703 364 A1 | 3/1996 |
| EP | 0 706 004 A2 | 4/1996 |
| EP | 0 779 436 A2 | 6/1997 |
| EP | 0 829 360 A2 | 3/1998 |
| EP | 0 845 603 A1 | 6/1998 |
| EP | 0 999 055 A2 | 5/2000 |
| GB | 2 155 152 A | 9/1985 |
| GB | 2 308 460 A | 6/1997 |
| WO | WO 98/07069 A1 | 2/1998 |
| WO | WO 99/00655 A2 | 1/1999 |
| WO | WO 99/04361 A1 | 1/1999 |
| WO | WO 99/17093 A1 | 4/1999 |
| WO | WO 99/52633 A1 | 10/1999 |
| WO | WO 00/00678 A1 | 1/2000 |
| WO | WO 00/43748 A1 | 7/2000 |
| WO | WO 00/60345 A1 | 10/2000 |
| WO | WO 01/09595 A2 | 2/2001 |
| WO | WO 01/09595 A3 | 2/2001 |

OTHER PUBLICATIONS

Thorsen, Todd: "Microfluidic technologies for high-throughput screening applications" (Online) Sep. 23, 2002 California Institute of Technology Pasadena, USA, XP002302465; Retrieved from the Internet: URL: http://resolver.caltech.edu/CaltechETD:etd-12012002-092026.

Todd Thorsen; Sebastian J. Maerkl, Stephen R. Quake: "Microfluidic Large-scale Integration" SCIENCE vol. 298, No. 5593 Oct. 18, 2002, pp. 580-584, XP002302473 Washington DC, USA.

"Biochips," Nature Biotechnology, vol. 18, Supplement 2000, pp. IT43-IT44, 2000.

"Chapter 9: Microfluidic Devices," Micromachined Transducers Sourcebook, pp. 779-882, 1998.

"Electro Microfluidic Dual In-Line Package (EMDIP)," Sandia National Laboratories, 2 pages, no date.

"Last Chance For Micromachines," The Economist Technology Quarterly, printed from website http://www.economist.com/science/displayStory.cfm?Story_ID=442930 on Jan. 25, 2001, 8 pages, Dec. 7, 2000.

"The Liver Chip," Technology Review, pp. 64-67, Mar. 2003.

Ahn, Chong H. et al., "Fluid Micropumps Based On Rotary Magnetic Actuators," Proceedings of 1995 IEEE Micro Electro Mechanical Systems Workshop (MEMS '95), Amsterdam, Netherlands, pp. 408-412, Jan. 29-Feb. 2, 1995.

Anderson, Rolfe C. et al., "Microfluidic Biochemical Analysis System," Transducers '97, 1997 International Conference on Solid-State Sensors and Actuators, Chicago, Illinois, pp. 477-480, Jun. 16-19, 1997.

Angell, James B. et al., "Silicon Micromechanical Devices," Scientific American, pp. cover, 44-55, Apr. 1983.

Armani, Deniz et al., "Re-Configurable Fluid Circuits By PDMS Elastomer Micromachining," IEEE Int. Conf. Micro Electro Mech. Syst. Tech. Digest, vol. 12, pp. 222-227, 1999.

Ashkin, A. et al., "Optical Trapping And Manipulation Of Single Cells Using Infrared Laser Beams," Nature, vol. 330, No. 24, pp. 769-771, Dec. 31, 1987.

Ashkin, A. et al., "Optical Trapping And Manipulation Of Viruses And Bacteria," Science, vol. 235, pp. 1517-1520, Mar. 20, 1987.

Ballantyne, J. P. et al., "Selective Area Metallization By Electron-Beam Controlled Direct Metallic Deposition," J. Vac. Sci. Technol., vol. 10, No. 6, pp. 1094-1097, Nov. 1973.

Benard, W. L. et al., "A Titanium-Nickel Shape-Memory Alloy Actuated Micropump," Transducers '97, 1997 International Conference on Solid-State Sensors and Actuators, Chicago, Illinois, pp. 361-364, Jun. 16-19, 1997.

Black, Harvey, "Tiny Technology Promises Tremendous Profits," The Scientist, vol. 15, No. 21, 4 pages, Oct. 29, 2001.

Bloomstein, T. M. et al., "Laser-Chemical Three-Dimensional Writing For Microelectromechanics And Application To Standard-Cell Microfluidics," J. Vac. Sci. Technol. B, vol. 10, No. 6, pp. 2671-2674, Nov. 1992.

Bousse, Luc et al., "Electrokinetically Controlled Microfluidic Analysis Systems," Annu. Rev. Biophys. Biomol. Struct., vol. 29, pp. 155-181, 2000.

Brechtel, R. et al., "Control Of The Electroosmotic Flow By Metal-Salt-Containing Buffers," Journal of Chromatography A, vol. 716, pp. 97-105, 1995.

Bryzek, Janusz et al., "Micromachines On The March", IEEE Spectrum, vol. 31, No. 5, pp. 20-31, May 1994.

Buchaillot, Lionel et al., "Silicon Nitride Thin Films Young's Modulus Determination By An Optical Non Destructive Method," Jpn. J. Appl. Phys., vol. 36, Part 2, No. 6B, pp. L794-L797, Jun. 15, 1997.

Buican, Tudor N. et al., "Automated Single-Cell Manipulation And Sorting By Light Trapping," Applied Optics, vol. 26, No. 24, pp. 5311-5316, Dec. 15, 1987.

Burbaum, Jonathan J. et al., "New Technologies For High-Throughput Screening," Current Opinion in Chemical Biology, vol. 1, pp. 72-78, 1997.

Cai, Weiwen, et al., "High-Resolution Restriction Maps Of Bacterial Artificial Chromosomes Constructed By Optical Mapping," Proc. Natl. Acad. Sci. USA, vol. 95, pp. 3390-3395, Mar. 1998.

Calkins, Kathryn, "Mycometrix: Rubber Chips," BioCentury, 2 pages, Oct. 16, 2000.

Castro, Alonso et al., "Fluorescence Detection And Size Measurement Of Single DNA Molecules," Analytical Chemistry, vol. 85, No. 7, pp. 849-852, Apr. 1, 1993.

Chang, Jun Keun et al., "Functional Integration Of Serial Dilution And Capillary Electrophoresis On A PDMS Microchip," Biotechnology and Bioprocess Engineering, vol. 8, No. 4, pp. 233-239, 2003.

Chen, Chichen et al., "Gray-Scale Photolithography Using Microfluidic Photomasks," PNAS, vol. 100, No. 4, pp. 1499-1504, Feb. 18, 2003.

Chiu, Chi-Sung et al., "Single Molecule Measurements Calibrate Green Fluorescent Protein Surface Densities On Transparent Beads For Use With 'Knock-In' Animals And Other Expression Systems," Journal of Neuroscience Methods, vol. 105, pp. 55-63, 2001.

Chiu, Daniel T. et al., "Patterned Deposition Of Cells And Proteins Onto Surfaces By Using Three-Dimensional Microfluidic Systems," PNAS, vol. 97, No. 6, pp. 2408-2413, Mar. 14, 2000.

Chou, Hou-Pu et al., "A Microfabricated Device For Sizing And Sorting DNA Molecules," Proc. Natl. Acad. Sci., vol. 96, pp. 11-13, Jan. 1999.

Chou, Hou-Pu et al., "A Microfabricated Rotary Pump," Biomedical Microdevices, vol. 3, No. 4, pp. 323-330, 2001.

Chou, Hou-Pu et al., "Integrated Elastomer Fluidic Lab-On-A-Chip-Surface Patterning And DNA Diagnostics," Proceedings of the Solid State Actuator and Sensor Workshop, Hilton Head, South Carolina, 4 pages, 2000.

Chou, Hou-Pu et al., "Multiple Disease Diagnostics On A Single Chip," Biophysics Lab, Caltech, pp. 1-4, Mar. 1, 2000.

Delamarche, Emmanuel et al., "Patterned Delivery Of Immunoglobulins To Surfaces Using Microfluidic Networks," Science, vol. 276, pp. 779-781, May 2, 1997.

Duffy, David C. et al., "Patterning Electroluminescent Materials With Feature Sizes As Small As 5µm Using Elastomeric Membranes As Masks For Dry Lift-Off," Advanced Materials, vol. 11, No. 7, pp. 546-552, 1999.

Duffy, David C. et al., "Rapid Prototyping Of Microfluidic Switches In Poly(dimethyl siloxane) And Their Actuation By Electro-Osmotic Flow," J. Micromech. Microeng., vol. 9, pp. 211-217, 1999.

Duffy, David C. et al., "Rapid Prototyping Of Microfluidic Systems In Poly(dimethylsiloxane)," Analytical Chemistry, vol. 70, No. 23, pp. 4974-4984, Dec. 1, 1998.

Effenhauser, Carlo S. et al., "Integrated Capillary Electrophoresis On Flexible Silicone Microdevices: Analysis Of DNA Restriction Fragments And Detection Of Single DNA Molecules On Microchips," Analytical Chemistry, vol. 69, No. 17, pp. 3451-3457, Sep. 1, 1997.

Effenhauser, Carlo S. et al., "Integrated Chip-Based Capillary Electrophoresis," Electrophoresis, vol. 18, pp. 2203-2213, 1997.

Eyal, Shulamit et al., "Velocity-Independent Microfluidic Flow Cytometry," Electrophoresis, vol. 23, pp. 2653-2657, 2002.

Fahrenberg, J. et al., "A Microvalve System Fabricated By Thermoplastic Molding," J. Micromech. Microeng., vol. 5, pp. 169-171, 1995.

Fettinger, J. C. et al., "Stacked Modules For Micro Flow Systems In Chemical Analysis: Concept And Studies Using An Enlarged Model," Sensors and Actuators B, vol. 17, pp. 19-25, 1993.

Fitzgerald, Deborah A., "making Every Nanoliter Count," The Scientist, vol. 15, No. 21, 8 pages, Oct. 10, 2001.

Folch, A. et al., "Molding Of Deep Polydimethylsiloxane Microstructures For Microfluidics And Biological Applications," Journal of Biomechanical Engineering, vol. 121, pp. 28-34, Feb. 1999.

Fu, Anne Y. et al., "A Microfabricated Fluorescence-Activated Cell-Sorter," Nature Biotechnology, vol. 17, pp. 1109-1111, Nov. 1999.

Galambos, Paul et al., "Electrical And Fluidic Packaging Of Surface Micromachined Electro-Microfluidic Devices," 8 pages, no date.

Gao, Jun et al., "Integrated Microfluidic System Enabling Protein Digestion, Peptide Separation, And Protein Identification," Analytical Chemistry, vol. 73, No. 11, pp. 2648-2655, Jun. 1, 2001.

Garno, Jayne C. et al., "Production Of Periodic Arrays Of Protein Nanostructures Using Particle Lithography," Langmuir, vol. 18, No. 21, pp. 8186-8192, 2002.

Gass, V. et al., "Integrated Flow-Regulated Silicon Micropump," Sensors and Actuators A, vol. 43, pp. 335-338, 1994.

Gerlach, Torsten, "Pumping Gases By A Silicon Micro Pump With Dynamic Passive Valves," Transducers '97, 1997 International Conference on Solid-State Sensors and Actuators, Chicago, Illinois, pp. 357-360, Jun. 16-19, 1997.

Goll, C. et al., "Microvalves With Bistable Buckled Polymer Diaphragms," J. Micromech. Microeng., vol. 6, pp. 77-79, 1996.

Gravesen, Peter et al., "Microfluidics-A Review," J. Micromech. Microeng., vol. 3, pp. 168-192, 1993.

Greene, Chana, "Characterizing The Properties Of PDMS," pp. 1-11, Summer 2000.

Grover, William H. et al., "Monolithic Membrane Valves And Diaphragm Pumps For Practical Large-Scale Integration Into Glass Microfluidic Devices," Sensors and Actuators B, vol. 89, pp. 315-323, 2003.

Guérin, L. J. et al., "Simple And Low Cost Fabrication Of Embedded Micro-Channels By Using A New Thick-Film Photoplastic," Transducer '97, 1997 International Conference on Solid- State Sensors and Actuators, Chicago, Illinois, pp. 1419-1422, Jun. 18-19, 1997.

Hansen, Carl. L. et al., "A Robust And Scalable Microfluidic Metering Method That Allows Protein Crystal Growth By Free Interface Diffusion," PNAS, vol. 99, No. 26, pp. 16531-16536, Dec. 24, 2002.

Harrison, D. Jed et al., "Micromachining A Miniaturized Capillary Electrophoresis-Based Chemical Analysis System On A Chip," Science, vol. 261, pp. 895-897, Aug. 13, 1993.

Hicks, Jennifer, "Genetics And Drug Discovery Dominate Microarray Research," R&D Magazine, pp. 28-33, Feb. 1999.

Hofmann, Oliver et al., "Modular Approach To Fabrication Of Three-Dimensional Microchannel Systems In PDMS—Application To Sheath Flow Microchips," Lab on a Chip, vol. 1, pp. 108-114, 2001.

Horn, Howard, "Lab Chips Sector: Microtechnologies Are Changing Healthcare And More," Life Sciences, pp. 19-21, Mar. 20, 2001.

Hornbeck, Larry J. et al., "Bistable Deformable Mirror Device," Spatial Light Modulators and Applications 1988 Technical Digest Series, Summaries of papers presented at the Spatial Light Modulators and Applications Topical Meeting, Optical Society of America, vol. 8, Postconference Edition, A215, pp. 107-110, Jun. 15-17, 1988.

Hosokawa, Kazuo et al., "A Microfluidic Device For Mixing Of Capillary-Drive Liquids," IEEJ Trans. SM, vol. 123, No. 1, pp. 23-24, 2003.

Hosokawa, Kazuo et al., "Handling Of Picoliter Liquid Samples In A Poly(dimethylsiloxane)-Based Microfluidic Device," Analytical Chemistry, vol. 71, No. 20, pp. 4781-4785, Oct.15, 1999.

Ikuta, Koji et al., "Three Dimensional Micro Integrated Fluid Systems (MIFS) Fabricated By Stereo Lithography," IEEE, pp. 1-6, 1994.

Jacobson, Stephen C. et al., "High-Speed Separations On A Microchip," Analytical Chemistry, vol. 66, No. 7, pp. 1114-1118, Apr. 1, 1994.

Jacobson, Stephen C. et al., "Microfluidic Devices For Electrokinetically Driven Parallel And Serial Mixing," Analytical Chemistry, vol. 71, No. 20, pp. 4455-4459, Oct. 15, 1999.

Jerman, Hal, "Electrically-Activated, Normally-Closed Diaphragm Valves," Transducers '91, 1991 International Conference on Solid-State Sensors and Actuators, pp. cover, 1045-1048, 1991.

Jo, Byung-Ho et al., "Fabrication Of Three-Dimensional Microfluidic Systems By Stacking Molded Polydimethylsiloxane (PDMS) Layers" SPIE, vol. 3877, pp. 222-229, Sep. 1999.

Jo, Byung-Ho et al., "Three-Dimensional Micro-Channel Fabrication In Polydimethylsiloxane (PDMS) Elastomer," Journal of Microelectromechanical Systems, vol. 9, No. 1, pp. 76-81, Mar. 2000.

Jung, D. R. et al., "Chemical And Physical Interactions At Metal/Self-Assembled Organic Monolayer Interfaces," pp. 1-54, 1994.

Kagan, C. R., "Organic-Inorganic Hybrid Materials As Semiconducting Channels In Thin-Film Field-Effect Transistors," Science, vol. 286, pp. 945-947, Oct. 29, 1999.

Kapur, Ravi et al., "Fabrication And Selective Surface Modification Of 3-Dimensionally Textured Biomedical Polymers From Etched Silicon Substrates," Journal of Biomedical Materials Research, vol. 33, pp. 205-216, 1996.

Keller, Richard A. et al., "Single-Molecule Fluorescence Analysis In Solution," Applied Spectroscopy, vol. 50, No. 7, pp. 12A-30A, Jul. 1996.

Kenis, Paul J. A. et al., "Microfabrication Inside Capillaries Using Multiphase Laminar Flow Patterning," Science, vol. 285, pp. 83-85, Jul. 2, 1999.

Khoo, Melvin et al., "A Novel Micromachined Magnetic Membrane Microfluid Pump," pp. 1-4, no date.

Kim, Enoch et al., "Micromolding In Capillaries: Applications In Materials Science," J. Am. Chem. Soc., vol. 118, No. 24, pp. 5722-5731, 1996.

Kim, Enoch et al., "Polymer Microstructures Formed By Moulding In Capillaries," Nature, vol. 376, pp. 581-584, Aug. 17, 1995.

Kirk-Othmer, "Concise Encyclopedia of Chemical Technolgy," John Wiley & Sons, 5 pages, no date.

Kopp, Martin U. et al., "Chemical Amplification: Continuous-Flow PCR On A Chip," Science, vol. 280, pp. 1046-1048, May 15, 1998.

Kuhn, Lawrence et al., "Silicon Charge Electrode Array For Ink Jet Printing," IEEE Transactions on Electron Devices, vol. ED-25, No. 10, pp. 1257-1260, Oct. 1978.

Kumar, Amit et al., "Features Of Gold Having Micrometer To Centimeter Dimensions Can Be Formed Through A Combination Of Stamping With An Elastomeric Stamp And An Alkanethiol 'Ink' Followed By Chemical Etching," Appl. Phys. Lett., vol. 63, No. 14, pp. 2002-2004, Oct. 4, 1993.

Kumar, Amit et al., "Patterning Self-Assembled Monolayers: Applications In Materials Science," Langmuir, vol. 10, pp. 1498-1511, 1994.

Lagally, Eric T. et al., "Fully Integrated PCR-Capillary Electrophoresis Microsystem For DNA Analysis," Lab On A Chip, vol. 1, pp. 102-107, 2001.

Lagally, Eric T. et al., "Monolithic Integrated Microfluidic DNA Amplification And Capillary Electrophoresis Analysis System," Sensors and Actuators B, vol. 63, pp. 138-146, 2000.

Lagally, E. T. et al., "Single-Molecule DNA Amplification And Analysis In An Integrated Microfluidic Device," Analytical Chemistry, vol. 73, No. 3, pp. 565-570, Feb. 1, 2001.

Lammerink, T. S. J. et al., "Modular Concept For Fluid Handling Systems," IEEE, pp. 389-394, 1996.

Lessard, Guillaume A. et al., "A Scanning Apertureless Fluorescence Microscope," 8 pages, no date.

Li, Paul C. H. et al., "Transport, Manipulation, And Reaction Of Biological Cells On-Chip Using Electrokinetic Effects," Analytical Chemistry, vol. 69, No. 8, pp. 1564-1568, Apr. 15, 1997.

Licklider, Larry et al., "A Micromachined Chip-Based Electrospray Source For Mass Spectrometry," Analytical Chemistry, vol. 72, No. 2, pp. 367-375, Jan. 15, 2000.

Lin, L. Y. et al., "Free-Space Micromachined Optical Switches For Optical Networking," IEEE Journal of Selected Topics In Quantum Electronics, vol. 5, No. 1, pp. 4-9, Jan. 1999.

Liu, Jian et al., "A Nanoliter Rotary Device For Polymerase Chain Reaction," Electrophoresis, vol. 23, pp. 1531-1536, 2002.

Lötters, J C et al., "The Mechanical Properties Of The Rubber Elastic Polymer Polydimethylsiloxane For Sensor Applications," J. Micromech. Microeng., vol. 7, pp. 145-147, 1997.

Lucy, Charles A. et al., "Characterization Of The Cationic Surfactant Induced Reversal Of Electroosmotic Flow In Capillary Electrophoresis," Anal. Chem., vol. 68, pp. 300-305, 1996.

Maluf, N., "An Introduction To Microelectromechanical Systems Engineering," Artech House Publishers, Boston London, pp. 42-45, Dec. 1999.

Manz, A. et al., "Micromachining Of Monocrystalline Silicon And Glass For Chemical Analysis Systems," Trends in Analytical Chemistry, vol. 10, No. 5, pp. 144-149, 1991.

Marshall, Sid, "Fundamental Changes Ahead For Lab Instrumentation," R&D Magazine, 5 pages, Feb. 1999.

Marsili, Ray, "Lab-On-A-Chip Poised To Revolutionize Sample Prep," R&D Magazine, 5 pages, Feb. 1999.

McDonald, J. Cooper et al., "Fabrication Of Microfluidic Systems In Poly(dimethylsiloxane)," Electrophoresis, vol. 21, pp. 27-40, 2000.

McDonald, J. Cooper et al., "Poly(dimethylsiloxane) As A Material For Fabricating Microfluidic Devices," Accounts of Chemical Research, vol. 35, No. 7, pp. 491-499, 2002.

Muller, Richard S. et al., "Surface-Micromachined Microoptical Elements And Systems," Proceedings of the IEEE, vol. 86, No. 8, pp. 1705-1720, Aug. 1998.

Ng, Jessamine M. K. et al., "Components For Integrated Poly(Dimethylsiloxane) Microfluidic Systems," Electrophoresis, vol. 23, pp. 3461-3473, 2002.

Oleschuk, Richard D. et al., "Analytical Microdevices For Mass Spectrometry," Trends In Analytical Chemistry, vol. 19, No. 6., pp. 379-388, 2000.

Olsson, Anders et al., "Simulation Studies Of Diffuser And Nozzle Elements For Valve-Less Micropumps," Transducers '97, 1997 International Conference on Solid-State Sensors and Actuators, Chicago, Illinois, pp. 1039-1042, Jun. 16-19, 1997.

Pethig, Ronald et al., "Applications Of Dielectrophoresis In Biotechnology," Tibtech, vol. 15, pp. 426-432, Oct. 1997.

Qin, Dong et al., "Elastomeric Light Valves," Adv. Mater., vol. 9, No. 5, pp. 407-410, 1997.

Qin, Dong et al., "Photolithography With Transparent Reflective Photomasks," J. Vac. Sci. Technol. B, vol. 16, No. 1, pp. 98-103, Jan. 1998.

Quake, Stephen R. et al., "From Micro- To Nanofabrication With Soft Materials," Science, vol. 290, pp. 1536-1540, Nov. 24, 2000.

Rapp, R. et al., "LIGA Micropump For Gases And Liquids," Sensors and Actuators A, vol. 40, pp. 57-61, Jan. 1994.

Roylance, Lynn Michelle et al., "A Batch-Fabricated Silicon Accelerometer," IEEE Transactions on Electron Devices, vol. ED-26, No. 12, pp. 1911-1917, Dec. 1979.

Samad, Akhtar et al., "Optical Mapping: A Novel, Single-Molecule Approach To Genomic Analysis," Genome Research, pp. 1-4, 1995.

Sanjoh, Akira et al., "Spatiotemporal Protein Crystal Growth Studies Using Microfluidic Silicon Devices," Journal of Crystal Growth, vol. 196, pp. 691-702, 1999.

Sasserath, J. et al., "Rapid Protyping And Development Of Microfluidic And BioMEMS Devices," IVD Technology, 12 pages, Jun. 2002.

Schasfoort, Richard B. M. et al., "Field-Effect Flow Control For Microfabricated Fluidic Networks," Science, vol. 286, pp. 942-945, Oct. 29, 1999.

Schueller, Olivier J. A. et al., "Fabrication Of Glassy Carbon Microstructures By Soft Lithography," Sensors and Actuators A, vol. 72, pp. 126-139, 1999.

Schwartz, David C. et al., "Optical Mapping Approaches To Molecular Genomics," Current Opinion in Biotechnolgy, vol. 8, pp. 70-74, 1997.

Shoji Shuichi, "Fluids For Sensor Systems," Topics in Current Chemistry, vol. 194, pp. 167-188, 1998.

Shoji, Shuichi et al., "Smallest Dead Volume Microvalves For Integrated Chemical Analyzing Systems," Transducers '91, 1991 International Conference on Solid-State Sensors and Actuators, San Francisco, California, pp. cover, 1052-1055, 1991.

Smits, J.G., "Piezoelectric Micropump With Three Valves Working Peristaltically," Sensors and Actuators, vol. A21-A23, pp. 203-206, 1990.

Sohn, L. L. et al., "Capacitance Cytometry: Measuring Biological Cells One By One," PNAS, vol. 97, No. 20, pp. 10687-10690, Sep. 26, 2000.

Thompson, L. F. et al., "Introduction To Microlithography," 185th Meeting of the American Chemical Society, Seattle, WA, pp. 2 cover pages, 1-13, Mar. 20-25, 1983.

Thorsen, Todd et al., "Dynamic Pattern Formation In A Vesicle-Generating Microfluidic Device," Physical Review Letters, vol. 86, No. 18, pp. 4163-4166, Apr. 30, 2001.

Thorsen, Todd et al., "Microfluidic Large-Scale Integration," Science, vol. 298, No. 5593, pp. 580-584, Oct. 18, 2002.

Tufte, O. N. et al., "Silicon Diffused-Element Piezoresistive Diaphragms," Journal of Applied Physics, vol. 33, No. 11, pp. 3322-3327, Nov. 1962.

Ullmann's Encyclopedia of Industrial Chemistry, Sections 6 to 6.3, Topic: Carbon Black, Sixth Edition, 7 pages, 1999.

Unger, Marc A. et al., "Monolithic Microfabricated Valves And Pumps By Multilayer Soft Lithography," Science, vol. 288, pp. 113-116, Apr. 7, 2000.

Unger, Marc A. et al., "Single-Molecule Fluorescence Observed Wtih Mercury Lamp Illumination," Biotechniques, vol. 27, No. 5, pp. 1008-1014, Nov. 1999.

Van De Pol, F.C.M. et al., "A Thermo-Pneumatic Actuation Principle For A Microminature Pump And Other Micromechanical Devices," Sensors and Actuators, vol. 17, Nos. 1-2, pp. 139-143, pp. 139-143, May 3, 1989.

Van De Pol, F.C.M. et al., "Micro Liquid Handling Devices—A Review," Micro Systems Technologies, vol. 90, pp. 799-805, 1990.

Van Den Berg, A. et al., "Micro Total Analysis Systems," Proceedings of the µTAS '94 Workshop, University of Twente, The Netherlands, 17 pages, Nov. 21-22, 1994.

Van Der Woerd, Mark et al., "Lab-On-A-Chip Based Protein Crystallization," National Aeronautics and Space Administration and Caliper, pp. 1-27, Oct. 25, 2001.

Van Der Woerd, Mark et al., "The Promise Of Macromolecular Crystallization In Microfluidic Chips," Journal of Structural Biology, vol. 142, pp. 180-187, 2003.

Verpoorte, Elisabeth M. J. et al., "Three-Dimensional Micro Flow Manifolds For Minaturized Chemical Analysis Systems," J. Micromech. Microeng., vol. 7, pp. 246-256, 1994.

Vieider, Christian et al., "A Pneumatically Actuated Micro Valve With A Silicon Rubber Membrane For Integration With Fluid Handling Systems," Transducers '95, 8th International Conference on Solid-State Sensors and Actuators and Eurosensors IX, Stockholm, Sweden, pp. 284-286, Jun. 25-29, 1995.

Washizu, Masao et al., "Molecular Dielectrophoresis Of Biopolymers," IEEE Transactions on Industry Applications, vol. 30, No. 4, pp. 835-843, Jul. 1994.

Whitesides, George M. et al., "Flexible Methods For Microfluidics," Physics Today, pp. 42-48, Jun. 2001.

Whitesides, George M. et al., "Soft Lithography In Biology And Biochemistry," Annu. Rev. Biomed. Eng., vol. 3, pp. 335-373, 2001.

Wilbur, James L. et al., "Lithographic Molding: A Convenient Route To Structures With Sub-Micrometer Dimensions," Adv. Mater., vol. 7, No. 7, pp. 649-652, 1995.

Wu, Hongkai et al., "Fabrication Of Complex Three-Dimensional Microchannel Systems In PDMS," J. Am. Chem. Soc., vol. 125, No. 2, pp. 554-559, 2003.

Xia, Younan et al., "Complex Optical Surfaces Formed By Replica Molding Against Elastomeric Masters," Science, vol. 273, pp. 347-349, Jul. 19, 1996.

Xia, Younan et al., "Micromolding Of Polymers In Capillaries: Applications In Microfabrication," Chem. Mater., vol. 8, No. 7, pp. 1559-1566, 1996.

Xia, Younan et al., "Reduction In The Size Of Features Of Patterned SAMs Generated By Microcontact Printing With Mechanical Compression Of The Stamp," Adv. Mater., vol. 7, No. 5, pp. 471-473, 1995.

Xia, Younan et al., "Soft Lithography," Angew. Chem. Int. Ed., vol. 37, pp. 551-575, 1998.

Xu, Bing et al., "Making Negative Poisson's Ratio Microstructures By Soft Lithography," Adv. Mater., vol. 11, No. 14, pp. 1186-1189, 1999.

Yang, T. J. et al., "An Apertureless Near-Field Microscope For Fluorescence Imaging," Applied Physics Letters, vol. 76, No. 3, pp. 378-380, Jan. 17, 2000.

Yang, Xing et al., "A Low Power MEMS Silicone/Parylene Valve," Solid-State Sensor and Actuator Workshop, Hilton Head Island, South Carolina, 4 pages, Jun. 7-11, 1998.

Yang, Xing et al., "A MEMS Thermopneumatic Silicone Membrane Valve," IEEE 10th Annual International Workshop of Micro Electro Mechanical Systems, Nagoya, Japan, pp. cover, 114-118, Jan. 26-30, 1997.

Yazdi, Navid et al., "Micromachined Inertial Sensors," Proceedings of IEEE, vol. 86, No. 8, pp. 1640-1659, Aug. 1998.

Young, A. M. et al., "Contoured Elastic-Membrane Microvalves For Microfluidic Network Integration," Journal of Biomechanical Engineering, vol. 121, pp. 2-6, Feb. 1999.

Zengerle, R. et al., "A Micro Membrane Pump With Electrostatic Actuation," Micro Electro Mechanical Systems '92, Travemünde, Germany, pp. 19-24, Feb. 4-7, 1992.

Zengerle, R. et al., "Performance Simulation Of Microminiaturized Membrane Pumps," 7th International Conference on Solid-State Sensors and Actuators, Yokohama, Japan, pp. 2 cover pages, 106-109, Jun. 7-10, 1993.

Zhao, Zhan, et al., "An Integrated Biochip Design And Fabrication," Proceedings of SPIE, vol. 4936, pp. 321-326, 2002.

\* cited by examiner

Fig. 10
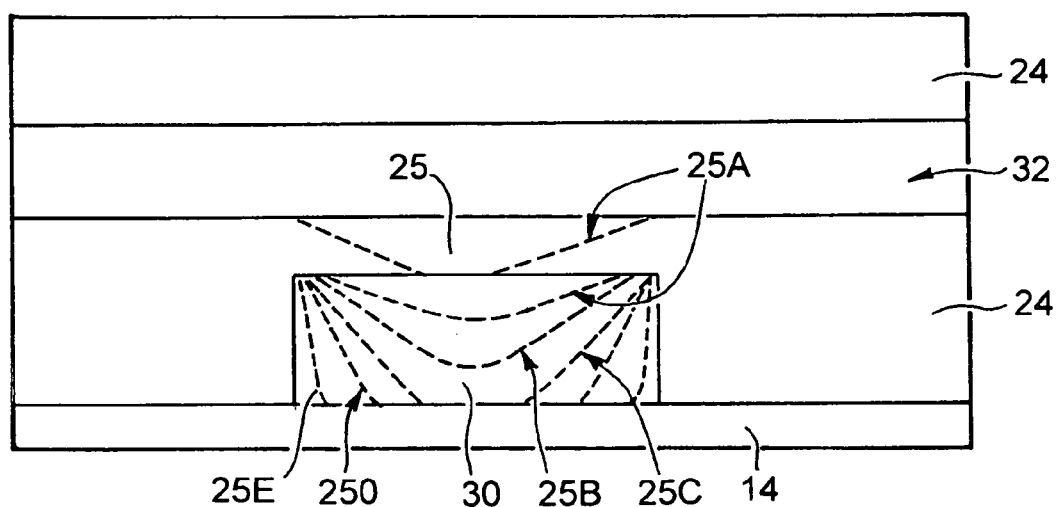
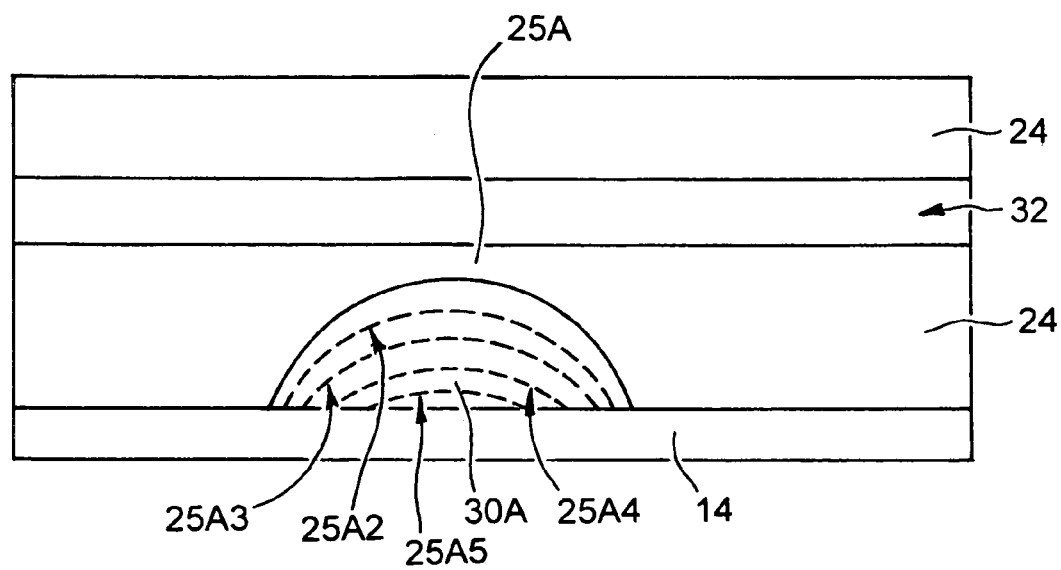
Fig. 11

011=3

Loading

Compartmentalization

Mixing

500 μm

Purging

MICROFLUIDIC LARGE SCALE INTEGRATION

CROSS-REFERENCE TO RELATED APPLICATIONS

The instant patent application claims priority from U.S. provisional patent application Ser. No. 60/413,860 filed Sep. 25, 2002, hereby incorporated by reference for all purposes.

STATEMENT AS TO RIGHTS TO INVENTIONS MADE UNDER FEDERALLY SPONSORED RESEARCH AND DEVELOPMENT

Work described herein has been supported, in part, by NSF a grant from the Army Research Office (No. DAAD19-00-1-0392) and the DARPA Bioflips program. The United States Government may therefore have certain rights in the invention.

BACKGROUND OF THE INVENTION

In the first part of the 20th century, engineers faced a problem commonly called the "Tyranny of Numbers": there is a practical limit to the complexity of macroscopically assembled systems. Using discrete components such as vacuum tubes, complex circuits quickly became very expensive to build and operate. The ENIAC I, created at the university of Pennsylvania in 1946, consisted of 19,000 vacuum tubes, weighed thirty tons, and used 200 kilowatts of power. The transistor was invented at Bell Laboratories in 1947 and went on to replace the bulky vacuum tubes in circuits, but connectivity remained a problem.

Although engineers could in principle design increasingly complex circuits consisting of hundreds of thousands of transistors, each component within the circuit had to be hand-soldered: an expensive, labor-intensive process. Adding more components to the circuit decreased its reliability as even a single cold solder joint rendered the circuit useless.

In the late 1950s Kilby and Noyce solved the "Tyranny of Numbers" problem for electronics by inventing the integrated circuit. By fabricating all of the components out of a single semiconductor—initially germanium, then silicon—Kilby and Noyce created circuits consisting of transistors, capacitors, resistors and their corresponding interconnects in situ, eliminating the need for manual assembly. By the mid-1970s, improved technology led to the development of large scale integration (LSI): complex integrated circuits containing hundreds to thousands of individual components.

Microfluidics offers the possibility of solving similar system integration issues for biology and chemistry. For example, Unger et al., Science, 288 (5463): 113 (2000) previously presented a candidate plumbing technology that allows fabrication of chips with monolithic valves made from the silicone elastomer polydimethylsiloxane (PDMS).

However, devices to date have lacked a method for a high degree of integration, other than simple repetition. Microfluidic systems have been used to demonstrate a diverse array of biological applications, including biomolecular separations, enzymatic assays, polymerase chain reaction (PCR), and immunohybridization reactions.

While these are excellent individual examples of scaled down processes of laboratory techniques, they are also stand-alone functionalities, comparable to a single component within an integrated circuit. The current industrial approach to addressing true biological integration has come in the form of enormous robotic fluidic workstations that take up entire laboratories and require considerable expense, space and labor, reminiscent of the macroscopic approach to circuits consisting of massive vacuum-tube based arrays in the early twentieth century.

Accordingly, there is a need in the art for high density, large scale integrated microfluidic devices, and methods for fabricating same

SUMMARY OF THE INVENTION

High-density microfluidic chips contain plumbing networks with thousands of micromechanical valves and hundreds of individually addressable chambers. These fluidic devices are analogous to electronic integrated circuits fabricated using large scale integration. A component of these networks is the fluidic multiplexor, which is a combinatorial array of binary valve patterns that exponentially increases the processing power of a network by allowing complex fluid manipulations with a minimal number of inputs. These integrated microfluidic networks can be used to construct the microfluidic analog of a comparator array and a microfluidic memory storage device resembling electronic random access memories.

An embodiment of a microfludic device in accordance with the present invention comprises a microfluidic flow channel formed in a first layer, and a first microfluidic control channel formed in a second layer adjacent to the first layer, the first microfluidic control channel separated from the microfluidic flow channel by a first deflectable membrane. A second microfluidic control channel is adjacent to the first microfluidic control channel and separated from the first microfluidic control channel by a second deflectable membrane.

An embodiment of a method in accordance with the present invention for controlling flow in a microfluidic structure, comprises, applying pressure to a control channel of a first control channel network separated from an adjacent flow channel by a first membrane, such that the first membrane is deflected into the flow channel. While pressure is maintained in the first control channel network, a pressure is applied to a control channel of a second control channel network separated from the first flow channel network by a second membrane, such that the second membrane is deflected into and seals the control channel of the first control channel network. While maintaining pressure in the control channel of the second control channel network, pressure in the first control channel network is released such that the first membrane remains deflected into the flow channel.

An embodiment of a microfabricated structure in accordance with the present invention comprises an array of storage locations defined by a first plurality of parallel flow channels orthogonal to a second plurality of parallel flow channels. A network of control lines is adjacent to the storage locations to define deflectable valves for isolating the storage locations. A first multiplexor structure is configured to govern flow through the first plurality of parallel flow channels. A second multiplexor structure configured to govern flow through the second plurality of parallel flow channels.

An embodiment of a microfabricated one-way valve in accordance with the present invention comprises a first elastomer layer comprising a vertical via portion and a seat portion, and a second elastomer layer comprising a flexible membrane. The flexible membrane has an integral end and a nonintegral end, the nonintegral end in contact with the seat portion and configured to be deflected into a second vertical via portion.

An alternative embodiment of a microfluidic device in accordance with the present invention, comprises, an elongated first flow channel, and a control channel overlapping the elongated first flow channel to define a first valve structure, the valve structure configured to deflect into the elongated first flow channel to define first and second segments of the first flow channel. A second flow channel is in fluid communication with the first segment, and a third flow channel in fluid communication with the second segment.

An embodiment of a method in accordance with the present invention for isolating elements of heterogeneous sample, comprises, flowing a sample comprising heterogeneous elements down a first elongated microfluidic flow channel. A first valve overlying the first elongated flow channel is actuated to define first and second segments, such that the first segment contains a first element of the heterogeneous sample and the second segment contains a second element of the heterogeneous sample.

An alternative embodiment of a microfluidic device in accordance with the present invention, comprises, a selectively-addressable storage location defined within elastomer material. A first flow channel is in selective fluid communication with the storage location through a valve. A second flow channel is in selective fluid communication with the storage location through a second valve.

An embodiment of a method in accordance with the present invention for selectively storing and recovering a material in a microfluidic device, comprises, providing a chamber defined within an elastomer material. A material is selectively flowed into the chamber through a first valve in a first flow channel, and the material is selectively flowed from the chamber through a second valve in a second flow channel.

These and other embodiments of the present invention, as well as its advantages and features, are described in more detail in conjunction with the text below and attached figures.

BRIEF DESCRIPTION OF THE DRAWINGS

FIG. 10 is a front sectional view of the valve of FIG. 7B showing actuation of the membrane.

FIG. 11 is a front sectional view of an alternative embodiment of a valve having a flow channel with a curved upper surface.

DETAILED DESCRIPTION OF THE PRESENT INVENTION

I. Microfabrication Overview

The following discussion relates to formation of microfabricated fluidic devices utilizing elastomer materials, as described generally in U.S. nonprovisional patent application Ser. No. 10/118,466 filed Apr. 5, 2002, Ser. No. 09/997,205 filed Nov. 28, 2001, Ser. No. 09/826,585 filed Apr. 6, 2001, Ser. No. 09/724,784 filed Nov. 28, 2000, and Ser. No. 09/605,520, filed Jun. 27, 2000. These patent applications are hereby incorporated by reference for all purposes.

1. Methods of Fabricating

Exemplary methods of fabricating the present invention are provided herein. It is to be understood that the present invention is not limited to fabrication by one or the other of these methods. Rather, other suitable methods of fabricating the present microstructures, including modifying the present methods, are also contemplated.

FIGS. 1 to 7B illustrate sequential steps of a first preferred method of fabricating the present microstructure, (which may be used as a pump or valve). FIGS. 8 to 18 illustrate sequential steps of a second preferred method of fabricating the present microstructure, (which also may be used as a pump or valve).

As will be explained, the preferred method of FIGS. 1 to 7B involves using pre-cured elastomer layers which are assembled and bonded. In an alternative method, each layer of elastomer may be cured "in place". In the following description "channel" refers to a recess in the elastomeric structure which can contain a flow of fluid or gas.

Figure 1:
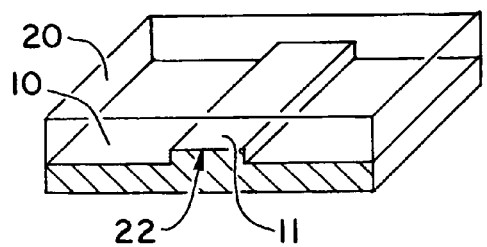
FIG. 1 is an illustration of a first elastomeric layer formed on top of a micromachined mold.

Referring to FIG. 1, a first micro-machined mold 10 is provided. Micro-machined mold 10 may be fabricated by a number of conventional silicon processing methods, including but not limited to photolithography, ion-milling, and electron beam lithography.

As can be seen, micro-machined mold 10 has a raised line or protrusion 11 extending therealong. A first elastomeric layer 20 is cast on top of mold 10 such that a first recess 21 will be formed in the bottom surface of elastomeric layer 20, (recess 22 corresponding in dimension to protrusion 11), as shown.

Figure 2:
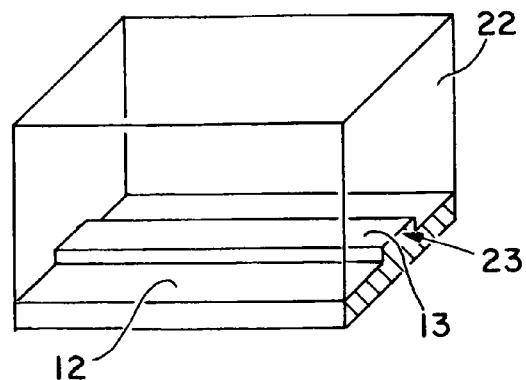
FIG. 2 is an illustration of a second elastomeric layer formed on top of a micromachined mold.

As can be seen in FIG. 2, a second micro-machined mold 12 having a raised protrusion 13 extending therealong is also provided. A second elastomeric layer 22 is cast on top of mold 12, as shown, such that a recess 23 will be formed in its bottom surface corresponding to the dimensions of protrusion 13.

Figure 3:
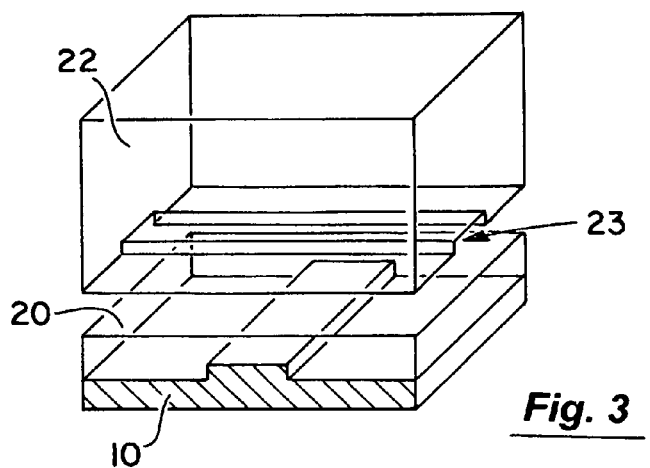
FIG. 3 is an illustration of the elastomeric layer of FIG. 2 removed from the micromachined mold and positioned over the top of the elastomeric layer of FIG. 1
Figure 4:
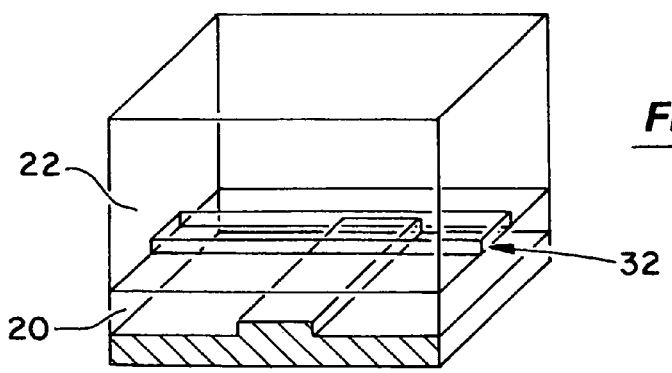
FIG. 4 is an illustration corresponding to FIG. 3, but showing the second elastomeric layer positioned on top of the first elastomeric layer.

As can be seen in the sequential steps illustrated in FIGS. 3 and 4, second elastomeric layer 22 is then removed from mold 12 and placed on top of first elastomeric layer 20. As can be seen, recess 23 extending along the bottom surface of second elastomeric layer 22 will form a flow channel 32.

Figure 5:
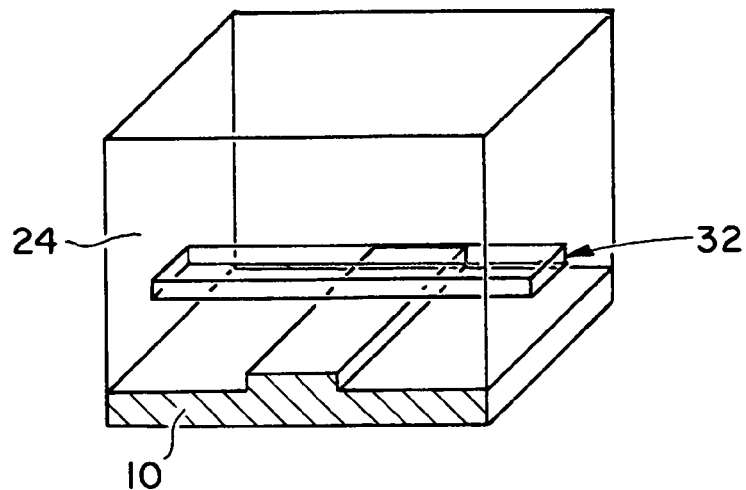
FIG. 5 is an illustration corresponding to FIG. 4, but showing the first and second elastomeric layers bonded together.

Referring to FIG. 5, the separate first and second elastomeric layers 20 and 22 (FIG. 4) are then bonded together to form an integrated (i.e.: monolithic) elastomeric structure 24.

Figure 6:
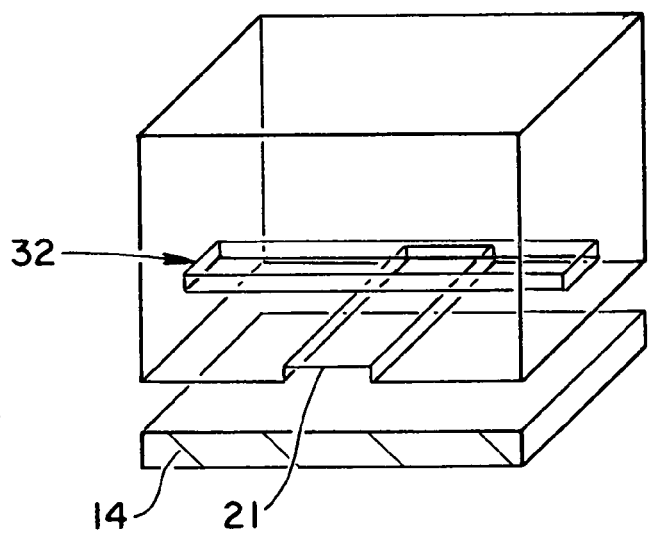
FIG. 6 is an illustration corresponding to FIG. 5, but showing the first micromachined mold removed and a planar substrate positioned in its place.
Figure 7A:
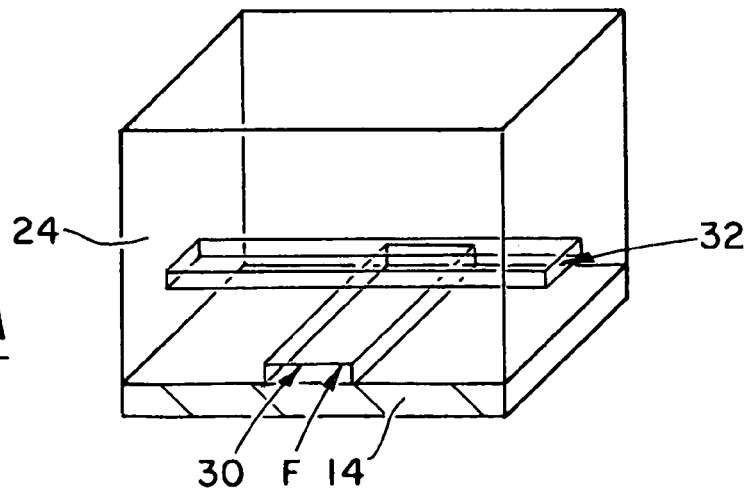
FIG. 7A is an illustration corresponding to FIG. 6, but showing the elastomeric structure sealed onto the planar substrate.
Figure 7B:
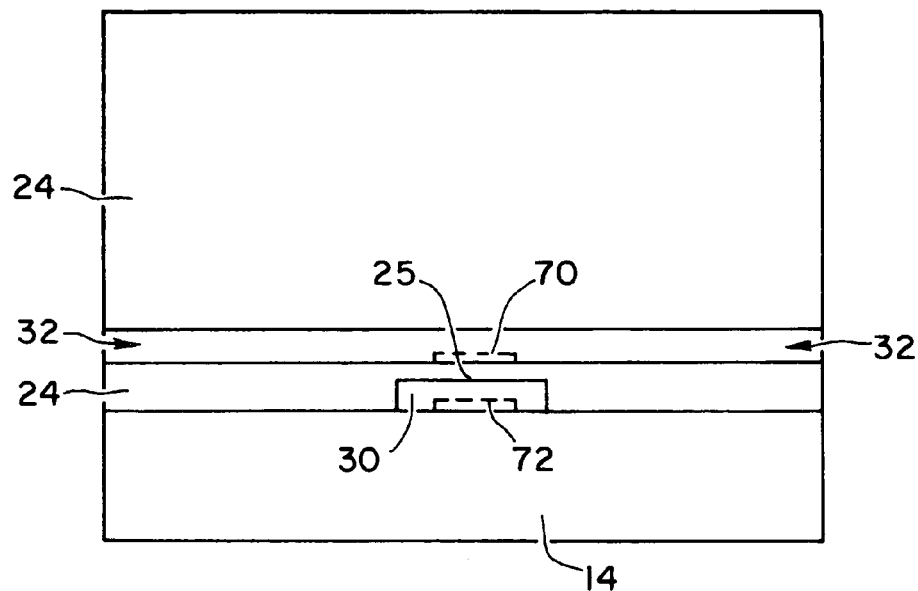
FIG. 7B is a front sectional view corresponding to FIG. 7A, showing an open flow channel.

As can been seen in the sequential step of FIGS. 6 and 7A, elastomeric structure 24 is then removed from mold 10 and positioned on top of a planar substrate 14. As can be seen in FIGS. 7A and 7B, when elastomeric structure 24 has been sealed at its bottom surface to planar substrate 14, recess 21 will form a flow channel 30.

The present elastomeric structures form a reversible hermetic seal with nearly any smooth planar substrate. An advantage to forming a seal this way is that the elastomeric structures may be peeled up, washed, and re-used. In preferred aspects, planar substrate 14 is glass. A further advantage of using glass is that glass is transparent, allowing optical interrogation of elastomer channels and reservoirs. Alternatively, the elastomeric structure may be bonded onto a flat elastomer layer by the same method as described above, forming a permanent and high-strength bond. This may prove advantageous when higher back pressures are used.

As can be seen in FIGS. 7A and 7B, flow channels 30 and 32 are preferably disposed at an angle to one another with a small membrane 25 of substrate 24 separating the top of flow channel 30 from the bottom of flow channel 32.

In preferred aspects, planar substrate 14 is glass. An advantage of using glass is that the present elastomeric structures may be peeled up, washed and reused. A further advantage of using glass is that optical sensing may be employed. Alternatively, planar substrate 14 may be an elastomer itself, which may prove advantageous when higher back pressures are used.

The method of fabrication just described may be varied to form a structure having a membrane composed of an elastomeric material different than that forming the walls of the channels of the device. This variant fabrication method is illustrated in FIGS. 7C–7G.

Figure 7H:
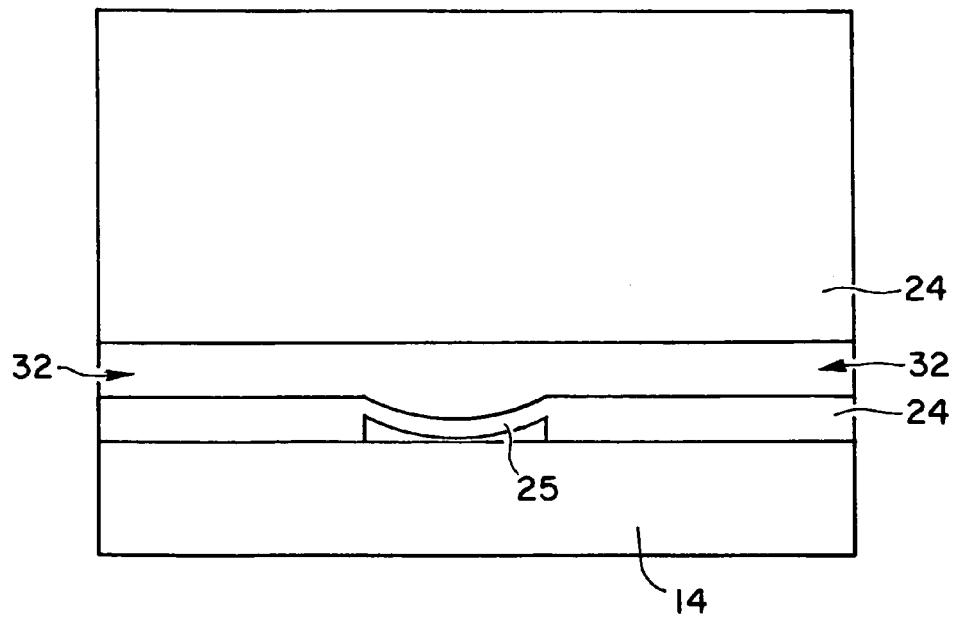
FIG. 7H is a front sectional view showing the valve of FIG. 7B in an actuated state.
Figure 7C:
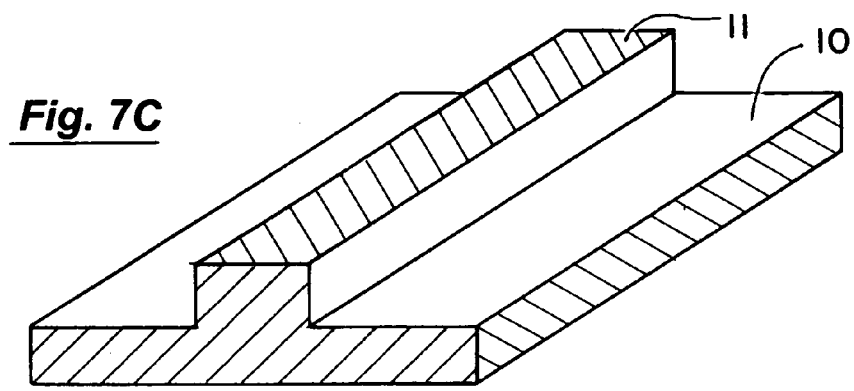
FIGS. 7C–7G are illustrations showing steps of a method for forming an elastomeric structure having a membrane formed from a separate elastomeric layer.
Figure 7D:
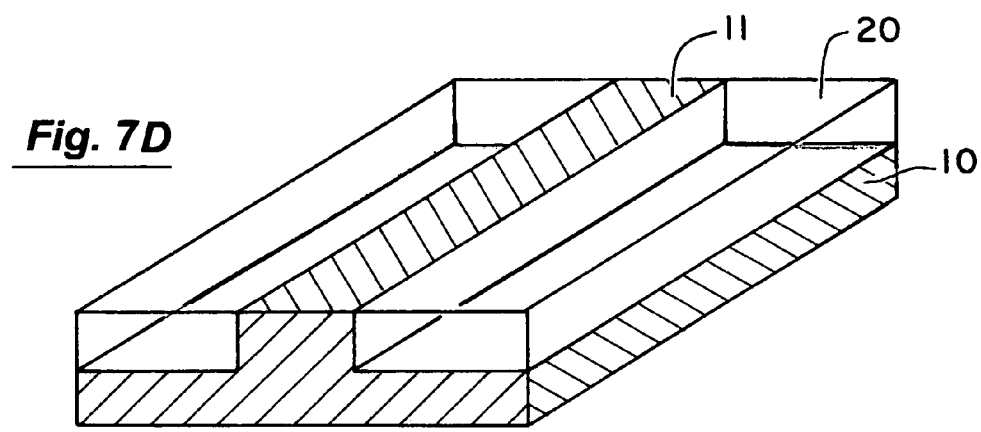

Referring to FIG. 7C, a first micro-machined mold 10 is provided. Micro-machined mold 10 has a raised line or protrusion 11 extending therealong. In FIG. 7D, first elastomeric layer 20 is cast on top of first micro-machined mold 10 such that the top of the first elastomeric layer 20 is flush with the top of raised line or protrusion 11. This may be accomplished by carefully controlling the volume of elastomeric material spun onto mold 10 relative to the known height of raised line 11. Alternatively, the desired shape could be formed by injection molding.

Figure 7E:
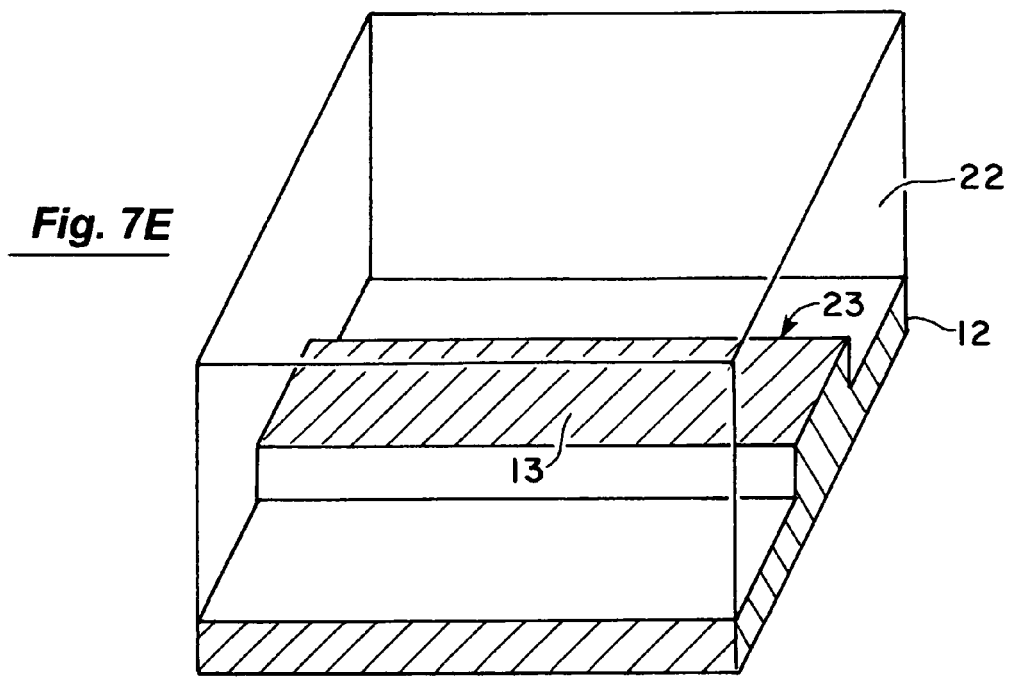

In FIG. 7E, second micro-machined mold 12 having a raised protrusion 13 extending therealong is also provided. Second elastomeric layer 22 is cast on top of second mold 12 as shown, such that recess 23 is formed in its bottom surface corresponding to the dimensions of protrusion 13.

Figure 7F:
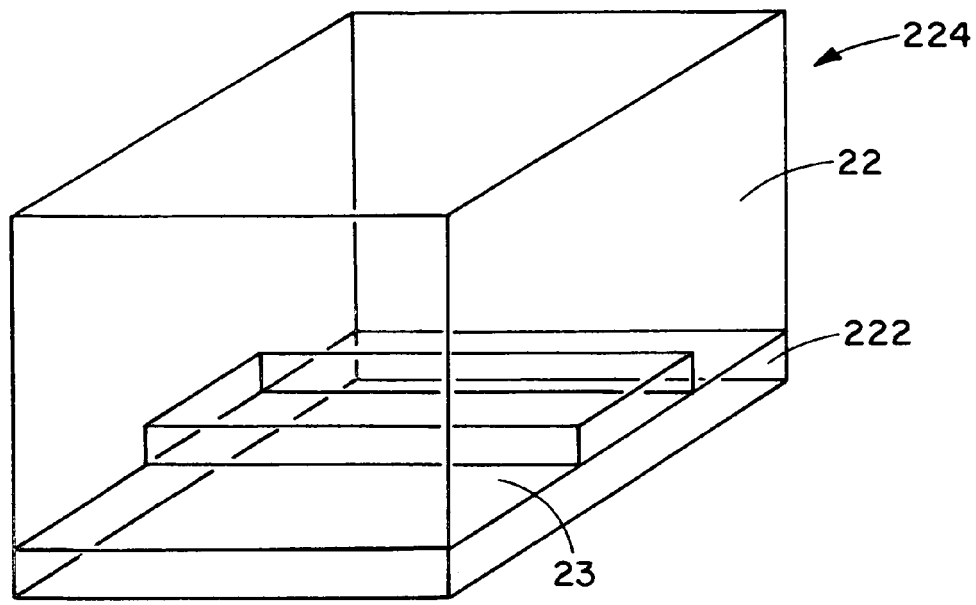

In FIG. 7F, second elastomeric layer 22 is removed from mold 12 and placed on top of third elastomeric layer 222. Second elastomeric layer 22 is bonded to third elastomeric layer 20 to form integral elastomeric block 224 using techniques described in detail below. At this point in the process, recess 23 formerly occupied by raised line 13 will form flow channel 23.

Figure 7G:
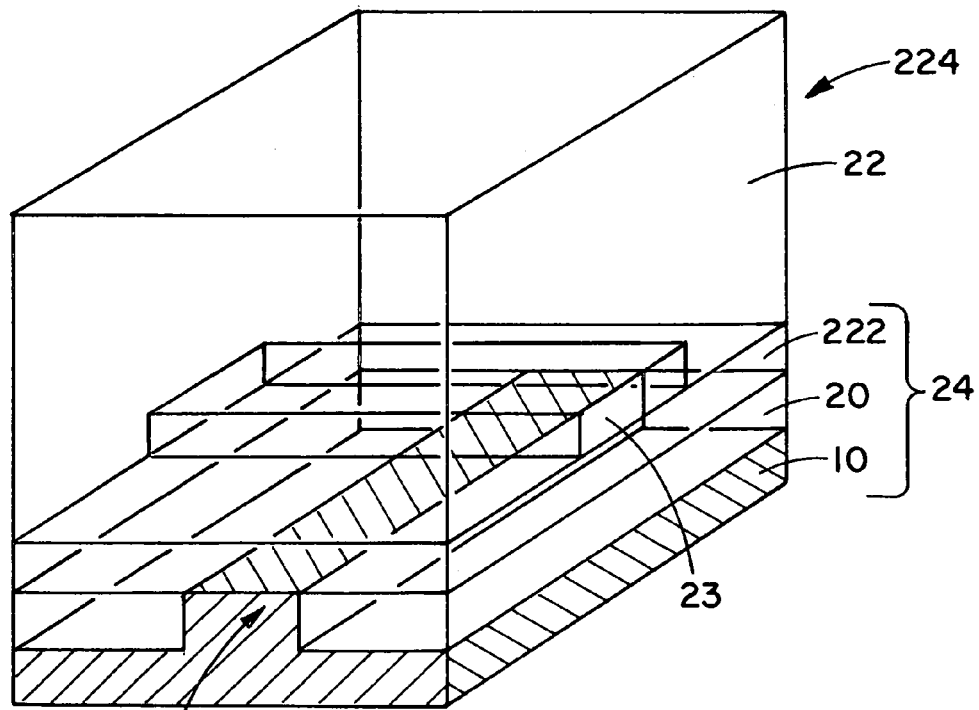

In FIG. 7G, elastomeric block 224 is placed on top of first micro-machined mold 10 and first elastomeric layer 20. Elastomeric block and first elastomeric layer 20 are then bonded together to form an integrated (i.e.: monolithic) elastomeric structure 24 having a membrane composed of a separate elastomeric layer 222.

When elastomeric structure 24 has been sealed at its bottom surface to a planar substrate in the manner described above in connection with FIG. 7A, the recess formerly occupied by raised line 11 will form flow channel 30.

The variant fabrication method illustrated above in conjunction with FIGS. 7C–7G offers the advantage of permitting the membrane portion to be composed of a separate material than the elastomeric material of the remainder of the structure. This is important because the thickness and elastic properties of the membrane play a key role in operation of the device. Moreover, this method allows the separate elastomer layer to readily be subjected to conditioning prior to incorporation into the elastomer structure. As discussed in detail below, examples of potentially desirable condition include the introduction of magnetic or electrically conducting species to permit actuation of the membrane, and/or the introduction of dopant into the membrane in order to alter its elasticity.

While the above method is illustrated in connection with forming various shaped elastomeric layers formed by replication molding on top of a micromachined mold, the present invention is not limited to this technique. Other techniques could be employed to form the individual layers of shaped elastomeric material that are to be bonded together. For example, a shaped layer of elastomeric material could be formed by laser cutting or injection molding, or by methods utilizing chemical etching and/or sacrificial materials as discussed below in conjunction with the second exemplary method.

An alternative method fabricates a patterned elastomer structure utilizing development of photoresist encapsulated within elastomer material. However, the methods in accordance with the present invention are not limited to utilizing photoresist. Other materials such as metals could also serve as sacrificial materials to be removed selective to the surrounding elastomer material, and the method would remain within the scope of the present invention. For example, gold metal may be etched selective to RTV 615 elastomer utilizing the appropriate chemical mixture.

2. Layer and Channel Dimensions

Microfabricated refers to the size of features of an elastomeric structure fabricated in accordance with an embodiment of the present invention. In general, variation in at least one dimension of microfabricated structures is controlled to the micron level, with at least one dimension being microscopic (i.e. below 1000 µm). Microfabrication typically involves semiconductor or MEMS fabrication techniques such as photolithography and spincoating that are designed for to produce feature dimensions on the microscopic level, with at least some of the dimension of the microfabricated structure requiring a microscope to reasonably resolve/image the structure.

In preferred aspects, flow channels 30, 32, 60 and 62 preferably have width-to-depth ratios of about 10:1. A non-exclusive list of other ranges of width-to-depth ratios in accordance with embodiments of the present invention is 0.1:1 to 100:1, more preferably 1:1 to 50:1, more preferably 2:1 to 20:1, and most preferably 3:1 to 15:1. In an exemplary aspect, flow channels 30, 32, 60 and 62 have widths of about 1 to 1000 microns. A non-exclusive list of other ranges of widths of flow channels in accordance with embodiments of the present invention is 0.01 to 1000 microns, more preferably 0.05 to 1000 microns, more preferably 0.2 to 500 microns, more preferably 1 to 250 microns, and most preferably 10 to 200 microns. Exemplary channel widths include 0.1 µm, 1 µm, 2 µm, 5 µm, 10 µm, 20 µm, 30 µm, 40 µm, 50 µm, 60 µm, 70 µm, 80 µm, 90 µm, 100 µm, 110 µm, 120 µm, 130 µm, 140 µm, 150 µm, 160 µm, 170 µm, 180 µm, 190 µm, 200 µm, 210 µm, 220 µm, 230 µm, 240 µm, and 250 µm.

Flow channels 30, 32, 60, and 62 have depths of about 1 to 100 microns. A non-exclusive list of other ranges of depths of flow channels in accordance with embodiments of the present invention is 0.01 to 1000 microns, more preferably 0.05 to 500 microns, more preferably 0.2 to 250 microns, and more preferably 1 to 100 microns, more preferably 2 to 20 microns, and most preferably 5 to 10 microns. Exemplary channel depths include including 0.01 µm, 0.02 µm, 0.05 µm, 0.1 µm, 0.2 µm, 0.5 µm, 1 µm, 2 µm, 3 µm, 4 µm, 5 µm, 7.5 µm, 10 µm, 12.5 µm, 15 µm, 17.5 µm, 20 µm, 22.5 µm, 25 µm, 30 µm, 40 µm, 50 µm, 75 µm, 100 µm, 150 µm, 200 µm, and 250 µm.

The flow channels are not limited to these specific dimension ranges and examples given above, and may vary in width in order to affect the magnitude of force required to deflect the membrane as discussed at length below in conjunction with FIG. 27. For example, extremely narrow flow channels having a width on the order of 0.01 µm may be useful in optical and other applications, as discussed in detail below. Elastomeric structures which include portions having channels of even greater width than described above are also contemplated by the present invention, and examples of applications of utilizing such wider flow channels include fluid reservoir and mixing channel structures.

The Elastomeric layers may be cast thick for mechanical stability. In an exemplary embodiment, elastomeric layer 22 of FIG. 1 is 50 microns to several centimeters thick, and more preferably approximately 4 mm thick. A non-exclusive list of ranges of thickness of the elastomer layer in accordance with other embodiments of the present invention is between about 0.1 micron to 10 cm, 1 micron to 5 cm, 10 microns to 2 cm, 100 microns to 10 mm.

Accordingly, membrane 25 of FIG. 7B separating flow channels 30 and 32 has a typical thickness of between about 0.01 and 1000 microns, more preferably 0.05 to 500 microns, more preferably 0.2 to 250, more preferably 1 to 100 microns, more preferably 2 to 50 microns, and most preferably 5 to 40 microns. As such, the thickness of elastomeric layer 22 is about 100 times the thickness of elastomeric layer 20. Exemplary membrane thicknesses include 0.01 μm, 0.02 μm, 0.03 μm, 0.05 μm, 0.1 μm, 0.2 μm, 0.3 μm, 0.5 μm, 1 μm, 2 μm, 3 μm, 5 μm, 7.5 μm, 10 μm, 12.5 μm, 15 μm, 17.5 μm, 20 μm, 22.5 μm, 25 μm, 30 μm, 40 μm, 50 μm, 75 μm, 100 μm, 150 μm, 200 μm, 250 m, 300 μm, 400 μm, 500 μm, 750 μm, and 1000 μm.

3. Soft Lithographic Bonding

Preferably, elastomeric layers are bonded together chemically, using chemistry that is intrinsic to the polymers comprising the patterned elastomer layers. Most preferably, the bonding comprises two component "addition cure" bonding.

In a preferred aspect, the various layers of elastomer are bound together in a heterogenous bonding in which the layers have a different chemistry. Alternatively, a homogenous bonding may be used in which all layers would be of the same chemistry. Thirdly, the respective elastomer layers may optionally be glued together by an adhesive instead. In a fourth aspect, the elastomeric layers may be thermoset elastomers bonded together by heating.

In one aspect of homogeneous bonding, the elastomeric layers are composed of the same elastomer material, with the same chemical entity in one layer reacting with the same chemical entity in the other layer to bond the layers together. In one embodiment, bonding between polymer chains of like elastomer layers may result from activation of a crosslinking agent due to light, heat, or chemical reaction with a separate chemical species.

Alternatively in a heterogeneous aspect, the elastomeric layers are composed of different elastomeric materials, with a first chemical entity in one layer reacting with a second chemical entity in another layer. In one exemplary heterogenous aspect, the bonding process used to bind respective elastomeric layers together may comprise bonding together two layers of RTV 615 silicone. RTV 615 silicone is a two-part addition-cure silicone rubber. Part A contains vinyl groups and catalyst; part B contains silicon hydride (Si—H) groups. The conventional ratio for RTV 615 is 10A:1B. For bonding, one layer may be made with 30A:1B (i.e. excess vinyl groups) and the other with 3A:1B (i.e. excess Si—H groups). Each layer is cured separately. When the two layers are brought into contact and heated at elevated temperature, they bond irreversibly forming a monolithic elastomeric substrate.

In an exemplary aspect of the present invention, elastomeric structures are formed utilizing Sylgard 182, 184 or 186, or aliphatic urethane diacrylates such as (but not limited to) Ebecryl 270 or Irr 245 from UCB Chemical.

In one embodiment in accordance with the present invention, two-layer elastomeric structures were fabricated from pure acrylated Urethane Ebe 270. A thin bottom layer was spin coated at 8000 rpm for 15 seconds at 170° C. The top and bottom layers were initially cured under ultraviolet light for 10 minutes under nitrogen utilizing a Model ELC 500 device manufactured by Electrolite corporation. The assembled layers were then cured for an additional 30 minutes. Reaction was catalyzed by a 0.5% vol/vol mixture of Irgacure 500 manufactured by Ciba-Geigy Chemicals. The resulting elastomeric material exhibited moderate elasticity and adhesion to glass.

In another embodiment in accordance with the present invention, two-layer elastomeric structures were fabricated from a combination of 25% Ebe 270/50% Irr245/25% isopropyl alcohol for a thin bottom layer, and pure acrylated Urethane Ebe 270 as a top layer. The thin bottom layer was initially cured for 5 min, and the top layer initially cured for 10 minutes, under ultraviolet light under nitrogen utilizing a Model ELC 500 device manufactured by Electrolite corporation. The assembled layers were then cured for an additional 30 minutes. Reaction was catalyzed by a 0.5% vol/vol mixture of Irgacure 500 manufactured by Ciba-Geigy Chemicals. The resulting elastomeric material exhibited moderate elasticity and adhered to glass.

Alternatively, other bonding methods may be used, including activating the elastomer surface, for example by plasma exposure, so that the elastomer layers/substrate will bond when placed in contact. For example, one possible approach to bonding together elastomer layers composed of the same material is set forth by Duffy et al, "Rapid Prototyping of Microfluidic Systems in Poly (dimethylsiloxane)", *Analytical Chemistry* (1998), 70, 4974–4984, incorporated herein by reference. This paper discusses that exposing polydimethylsiloxane (PDMS) layers to oxygen plasma causes oxidation of the surface, with irreversible bonding occurring when the two oxidized layers are placed into contact.

Yet another approach to bonding together successive layers of elastomer is to utilize the adhesive properties of uncured elastomer. Specifically, a thin layer of uncured elastomer such as RTV 615 is applied on top of a first cured elastomeric layer. Next, a second cured elastomeric layer is placed on top of the uncured elastomeric layer. The thin middle layer of uncured elastomer is then cured to produce a monolithic elastomeric structure. Alternatively, uncured elastomer can be applied to the bottom of a first cured elastomer layer, with the first cured elastomer layer placed on top of a second cured elastomer layer. Curing the middle thin elastomer layer again results in formation of a monolithic elastomeric structure.

Where encapsulation of sacrificial layers is employed to fabricate the elastomer structure, bonding of successive elastomeric layers may be accomplished by pouring uncured elastomer over a previously cured elastomeric layer and any sacrificial material patterned thereupon. Bonding between elastomer layers occurs due to interpenetration and reaction of the polymer chains of an uncured elastomer layer with the polymer chains of a cured elastomer layer. Subsequent curing of the elastomeric layer will create a bond between the elastomeric layers and create a monolithic elastomeric structure.

Referring to the first method of FIGS. 1 to 7B, first elastomeric layer 20 may be created by spin-coating an RTV mixture on microfabricated mold 12 at 2000 rpm's for 30 seconds yielding a thickness of approximately 40 microns. Second elastomeric layer 22 may be created by spin-coating an RTV mixture on microfabricated mold 11. Both layers 20 and 22 may be separately baked or cured at about 80° C. for 1.5 hours. The second elastomeric layer 22 may be bonded onto first elastomeric layer 20 at about 80° C. for about 1.5 hours.

Micromachined molds 10 and 12 may be patterned photoresist on silicon wafers. In an exemplary aspect, a Shipley SJR 5740 photoresist was spun at 2000 rpm patterned with a high resolution transparency film as a mask and then developed yielding an inverse channel of approximately 10 microns in height. When baked at approximately 200° C. for about 30 minutes, the photoresist reflows and the inverse channels become rounded. In preferred aspects, the molds may be treated with trimethylchlorosilane (TMCS) vapor for about a minute before each use in order to prevent adhesion of silicone rubber.

4. Suitable Elastomeric Materials

Allcock et al, *Contemporary Polymer Chemistry*, $2^{nd}$ Ed. describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials may be characterized by a Young's modulus. Elastomeric materials having a Young's modulus of between about 1 Pa–1 TPa, more preferably between about 10 Pa–100 GPa, more preferably between about 20 Pa–1 GPa, more preferably between about 50 Pa–10 MPa, and more preferably between about 100 Pa–1 MPa are useful in accordance with the present invention, although elastomeric materials having a Young's modulus outside of these ranges could also be utilized depending upon the needs of a particular application.

The systems of the present invention may be fabricated from a wide variety of elastomers. In an exemplary aspect, the elastomeric layers may preferably be fabricated from silicone rubber. However, other suitable elastomers may also be used.

In an exemplary aspect of the present invention, the present systems are fabricated from an elastomeric polymer such as GE RTV 615 (formulation), a vinyl-silane crosslinked (type) silicone elastomer (family). However, the present systems are not limited to this one formulation, type or even this family of polymer; rather, nearly any elastomeric polymer is suitable. An important requirement for the preferred method of fabrication of the present microvalves is the ability to bond multiple layers of elastomers together. In the case of multilayer soft lithography, layers of elastomer are cured separately and then bonded together. This scheme requires that cured layers possess sufficient reactivity to bond together. Either the layers may be of the same type, and are capable of bonding to themselves, or they may be of two different types, and are capable of bonding to each other. Other possibilities include the use an adhesive between layers and the use of thermoset elastomers.

Given the tremendous diversity of polymer chemistries, precursors, synthetic methods, reaction conditions, and potential additives, there are a huge number of possible elastomer systems that could be used to make monolithic elastomeric microvalves and pumps. Variations in the materials used will most likely be driven by the need for particular material properties, i.e. solvent resistance, stiffness, gas permeability, or temperature stability.

There are many, many types of elastomeric polymers. A brief description of the most common classes of elastomers is presented here, with the intent of showing that even with relatively "standard" polymers, many possibilities for bonding exist. Common elastomeric polymers include polyisoprene, polybutadiene, polychloroprene, polyisobutylene, poly(styrene-butadiene-styrene), the polyurethanes, and silicones.

Polyisoprene, Polybutadiene, Polychloroprene:

Polyisoprene, polybutadiene, and polychloroprene are all polymerized from diene monomers, and therefore have one double bond per monomer when polymerized. This double bond allows the polymers to be converted to elastomers by vulcanization (essentially, sulfur is used to form crosslinks between the double bonds by heating). This would easily allow homogeneous multilayer soft lithography by incomplete vulcanization of the layers to be bonded; photoresist encapsulation would be possible by a similar mechanism.

Polyisobutylene:

Pure Polyisobutylene has no double bonds, but is crosslinked to use as an elastomer by including a small amount (~1%) of isoprene in the polymerization. The isoprene monomers give pendant double bonds on the Polyisobutylene backbone, which may then be vulcanized as above.

Poly(styrene-butadiene-styrene):

Poly(styrene-butadiene-styrene) is produced by living anionic polymerization (that is, there is no natural chain-terminating step in the reaction), so "live" polymer ends can exist in the cured polymer. This makes it a natural candidate for the present photoresist encapsulation system (where there will be plenty of unreacted monomer in the liquid layer poured on top of the cured layer). Incomplete curing would allow homogeneous multilayer soft lithography (A to A bonding). The chemistry also facilitates making one layer with extra butadiene ("A") and coupling agent and the other layer ("B") with a butadiene deficit (for heterogeneous multilayer soft lithography). SBS is a "thermoset elastomer", meaning that above a certain temperature it melts and becomes plastic (as opposed to elastic); reducing the temperature yields the elastomer again. Thus, layers can be bonded together by heating.

Polyurethanes:

Polyurethanes are produced from di-isocyanates (A-A) and di-alcohols or di-amines (B-B); since there are a large variety of di-isocyanates and di-alcohols/amines, the number of different types of polyurethanes is huge. The A vs. B nature of the polymers, however, would make them useful for heterogeneous multilayer soft lithography just as RTV 615 is: by using excess A-A in one layer and excess B-B in the other layer.

Silicones:

Silicone polymers probably have the greatest structural variety, and almost certainly have the greatest number of commercially available formulations. The vinyl-to-(Si—H) crosslinking of RTV 615 (which allows both heterogeneous multilayer soft lithography and photoresist encapsulation) has already been discussed, but this is only one of several crosslinking methods used in silicone polymer chemistry.

5. Operation of Device

FIGS. 7B and 7H together show the closing of a first flow channel by pressurizing a second flow channel, with FIG. 7B (a front sectional view cutting through flow channel 32 in corresponding FIG. 7A), showing an open first flow channel 30; with FIG. 7H showing first flow channel 30 closed by pressurization of the second flow channel 32.

Referring to FIG. 7B, first flow channel 30 and second flow channel 32 are shown. Membrane 25 separates the flow channels, forming the top of first flow channel 30 and the bottom of second flow channel 32. As can be seen, flow channel 30 is "open".

As can be seen in FIG. 7H, pressurization of flow channel 32 (either by gas or liquid introduced therein) causes membrane 25 to deflect downward, thereby pinching off flow F passing through flow channel 30. Accordingly, by varying the pressure in channel 32, a linearly actuable valving system is provided such that flow channel 30 can be opened or closed by moving membrane 25 as desired. (For illustration purposes only, channel 30 in FIG. 7G is shown in a "mostly closed" position, rather than a "fully closed" position).

Since such valves are actuated by moving the roof of the channels themselves (i.e.: moving membrane 25) valves and pumps produced by this technique have a truly zero dead volume, and switching valves made by this technique have a dead volume approximately equal to the active volume of the valve, for example about 100×100×10 μm=100 pL. Such dead volumes and areas consumed by the moving membrane are approximately two orders of magnitude smaller than known conventional microvalves. Smaller and larger valves and switching valves are contemplated in the present invention, and a non-exclusive list of ranges of dead volume includes 1 aL to 1 uL, 100 aL to 100 nL, 1 fL to 10 nL, 100 fL to 1 nL, and 1 pL to 100 pL.

The extremely small volumes capable of being delivered by pumps and valves in accordance with the present invention represent a substantial advantage. Specifically, the smallest known volumes of fluid capable of being manually metered is around 0.1 μl. The smallest known volumes capable of being metered by automated systems is about ten-times larger (1 μl). Utilizing pumps and valves in accordance with the present invention, volumes of liquid of 10 nl or smaller can routinely be metered and dispensed. The accurate metering of extremely small volumes of fluid enabled by the present invention would be extremely valuable in a large number of biological applications, including diagnostic tests and assays.

Equation 1 represents a highly simplified mathematical model of deflection of a rectangular, linear, elastic, isotropic plate of uniform thickness by an applied pressure:

$$w=(BPb^4)/(Eh^3) \qquad (1)$$

where:

w=deflection of plate;

B=shape coefficient (dependent upon length vs. width and support of edges of plate);

p=applied pressure;

b=plate width

E=Young's modulus; and h=plate thickness.

Thus even in this extremely simplified expression, deflection of an elastomeric membrane in response to a pressure will be a function of: the length, width, and thickness of the membrane, the flexibility of the membrane (Young's modulus), and the applied actuation force. Because each of these parameters will vary widely depending upon the actual dimensions and physical composition of a particular elastomeric device in accordance with the present invention, a wide range of membrane thicknesses and elasticity's, channel widths, and actuation forces are contemplated by the present invention.

It should be understood that the formula just presented is only an approximation, since in general the membrane does not have uniform thickness, the membrane thickness is not necessarily small compared to the length and width, and the deflection is not necessarily small compared to length, width, or thickness of the membrane. Nevertheless, the equation serves as a useful guide for adjusting variable parameters to achieve a desired response of deflection versus applied force.

Figure 8A:
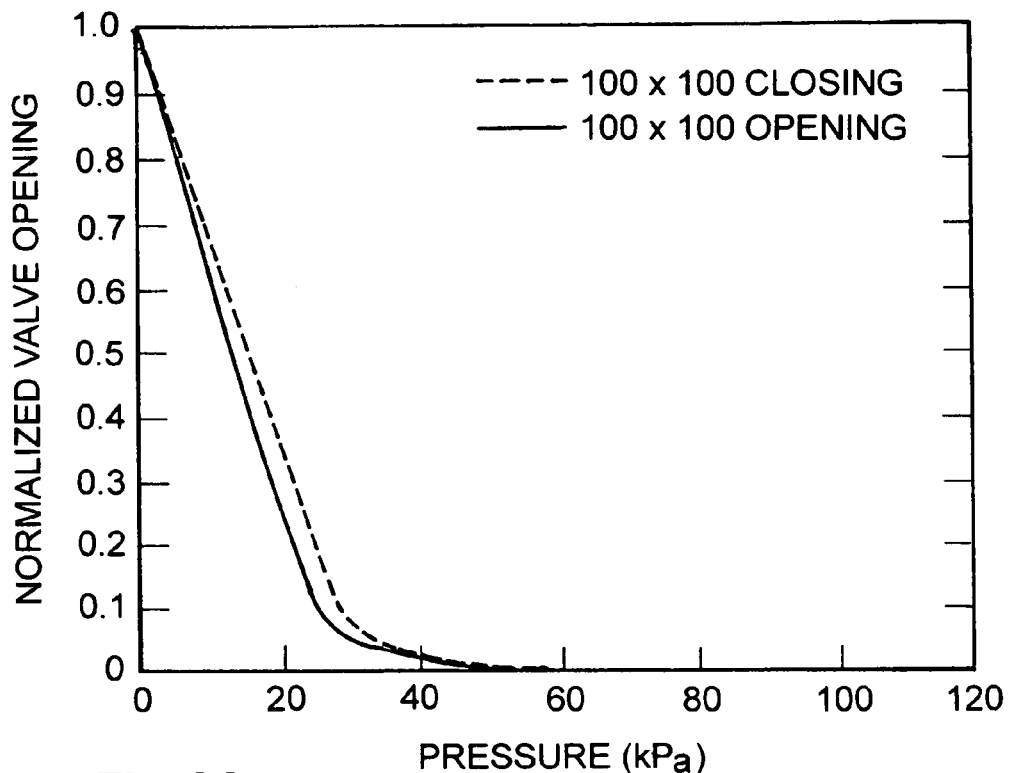
FIGS. 8A and 8B illustrates valve opening vs. applied pressure for various flow channels.
Figure 8B:
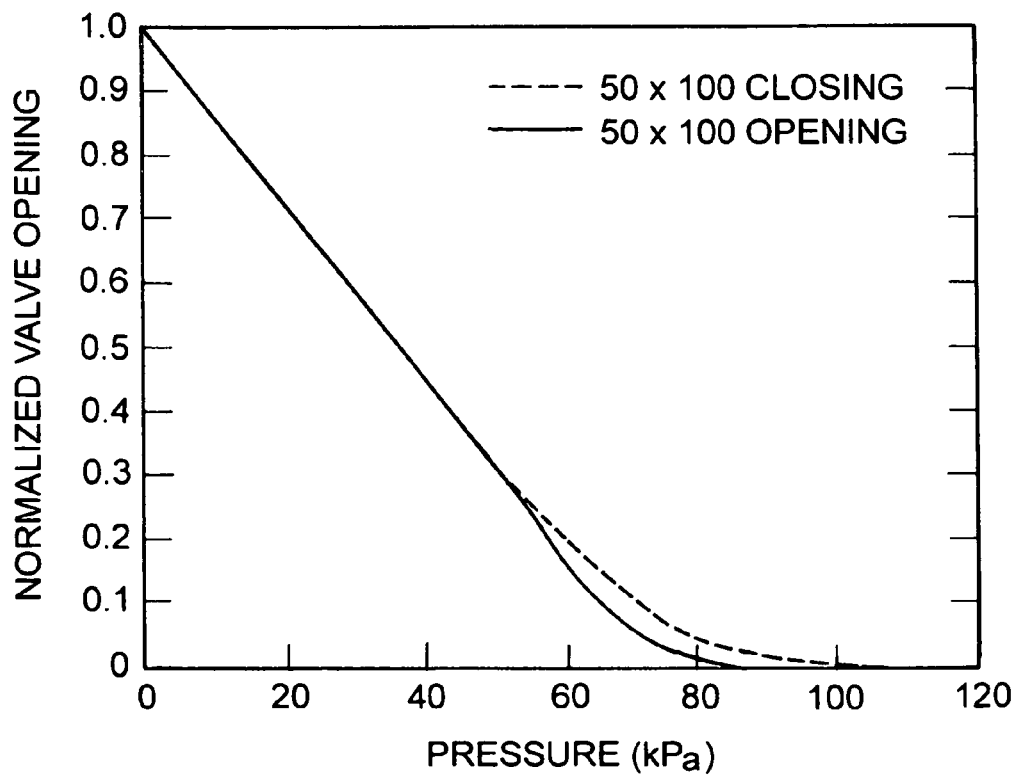
Figure 21:
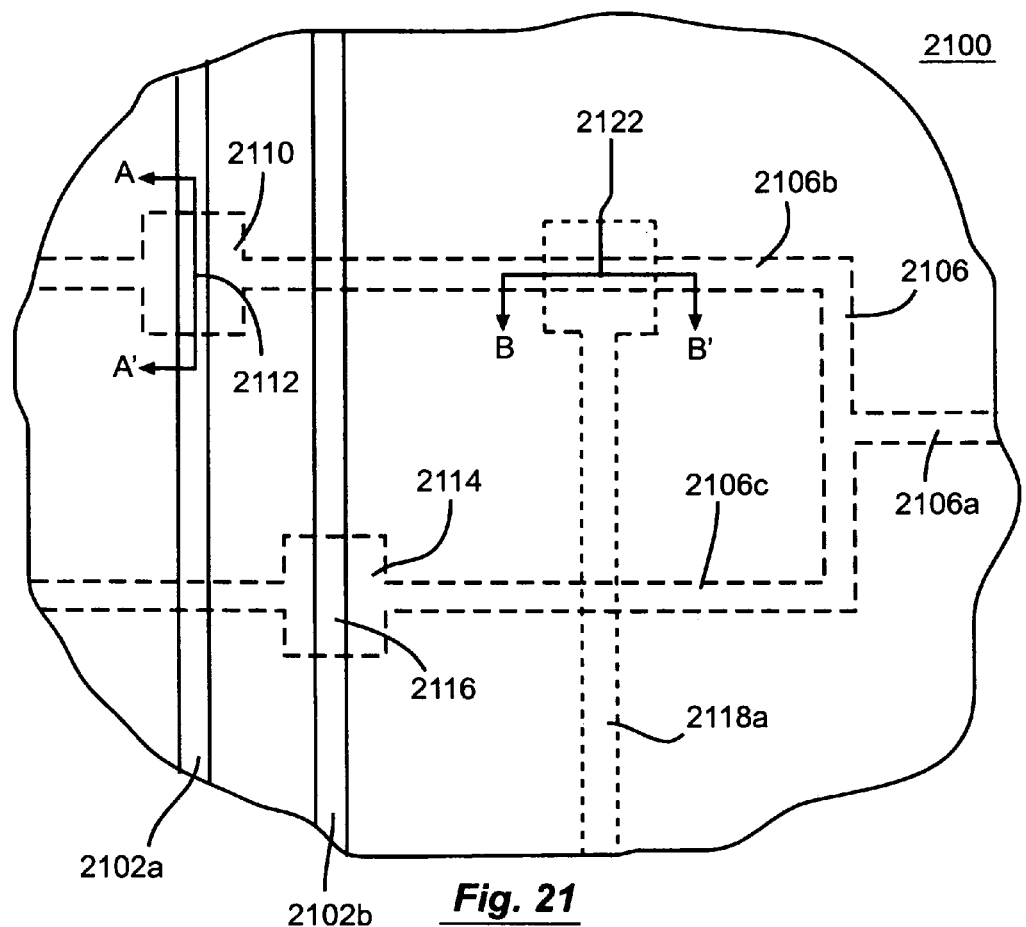
FIG. 21 shows a simplified plan view of an embodiment of a microfluidic structure utilizing control channels to control other control channels.
Figure 21A:
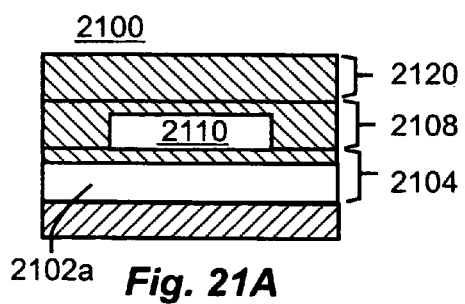
FIG. 21A shows a simplified cross-sectional view of the structure of FIG. 21 taken along the line 21A–21A'.
Figure 21B:
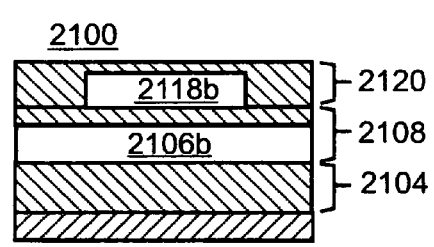
FIG. 21B shows a simplified cross-sectional view of the structure of FIG. 21 taken along the line 21B–21B'.

FIGS. 8A and 8B illustrate valve opening vs. applied pressure for a 100 μm wide first flow channel 30 and a 50 μm wide second flow channel 32. The membrane of this device was formed by a layer of General Electric Silicones RTV 615 having a thickness of approximately 30 μm and a Young's modulus of approximately 750 kPa. FIGS. 21a and 21b show the extent of opening of the valve to be substantially linear over most of the range of applied pressures.

Air pressure was applied to actuate the membrane of the device through a 10 cm long piece of plastic tubing having an outer diameter of 0.025" connected to a 25 mm piece of stainless steel hypodermic tubing with an outer diameter of 0.025" and an inner diameter of 0.013". This tubing was placed into contact with the control channel by insertion into the elastomeric block in a direction normal to the control channel. Air pressure was applied to the hypodermic tubing from an external LHDA miniature solenoid valve manufactured by Lee Co.

While control of the flow of material through the device has so far been described utilizing applied gas pressure, other fluids could be used.

For example, air is compressible, and thus experiences some finite delay between the time of application of pressure by the external solenoid valve and the time that this pressure is experienced by the membrane. In an alternative embodiment of the present invention, pressure could be applied from an external source to a noncompressible fluid such as water or hydraulic oils, resulting in a near-instantaneous transfer of applied pressure to the membrane. However, if the displaced volume of the valve is large or the control channel is narrow, higher viscosity of a control fluid may contribute to delay in actuation. The optimal medium for transferring pressure will therefore depend upon the particular application and device configuration, and both gaseous and liquid media are contemplated by the invention.

While external applied pressure as described above has been applied by a pump/tank system through a pressure regulator and external miniature valve, other methods of applying external pressure are also contemplated in the present invention, including gas tanks, compressors, piston systems, and columns of liquid. Also contemplated is the use of naturally occurring pressure sources such as may be found inside living organisms, such as blood pressure, gastric pressure, the pressure present in the cerebrospinal fluid, pressure present in the intra-ocular space, and the pressure exerted by muscles during normal flexure. Other methods of regulating external pressure are also contemplated, such as miniature valves, pumps, macroscopic peristaltic pumps, pinch valves, and other types of fluid regulating equipment such as is known in the art.

As can be seen, the response of valves in accordance with embodiments of the present invention have been experimentally shown to be almost perfectly linear over a large portion of its range of travel, with minimal hysteresis. Accordingly, the present valves are ideally suited for microfluidic metering and fluid control. The linearity of the valve response demonstrates that the individual valves are well modeled as Hooke's Law springs. Furthermore, high pressures in the flow channel (i.e.: back pressure) can be countered simply by increasing the actuation pressure. Experimentally, the present inventors have achieved valve closure at back pressures of 70 kPa, but higher pressures are also contemplated. The following is a nonexclusive list of pressure ranges encompassed by the present invention: 10 Pa–25 MPa; 100 Pa–10 Mpa, 1 kPa–1 MPa, 1 kPa–300 kPa, 5 kPa–200 kPa, and 15 kPa–100 kPa.

While valves and pumps do not require linear actuation to open and close, linear response does allow valves to more easily be used as metering devices. In one embodiment of the invention, the opening of the valve is used to control flow rate by being partially actuated to a known degree of closure. Linear valve actuation makes it easier to determine the amount of actuation force required to close the valve to a desired degree of closure. Another benefit of linear actuation is that the force required for valve actuation may be easily determined from the pressure in the flow channel. If actuation is linear, increased pressure in the flow channel may be countered by adding the same pressure (force per unit area) to the actuated portion of the valve.

Linearity of a valve depends on the structure, composition, and method of actuation of the valve structure. Furthermore, whether linearity is a desirable characteristic in a valve depends on the application. Therefore, both linearly and non-linearly actuable valves are contemplated in the present invention, and the pressure ranges over which a valve is linearly actuable will vary with the specific embodiment.

Figure 9:
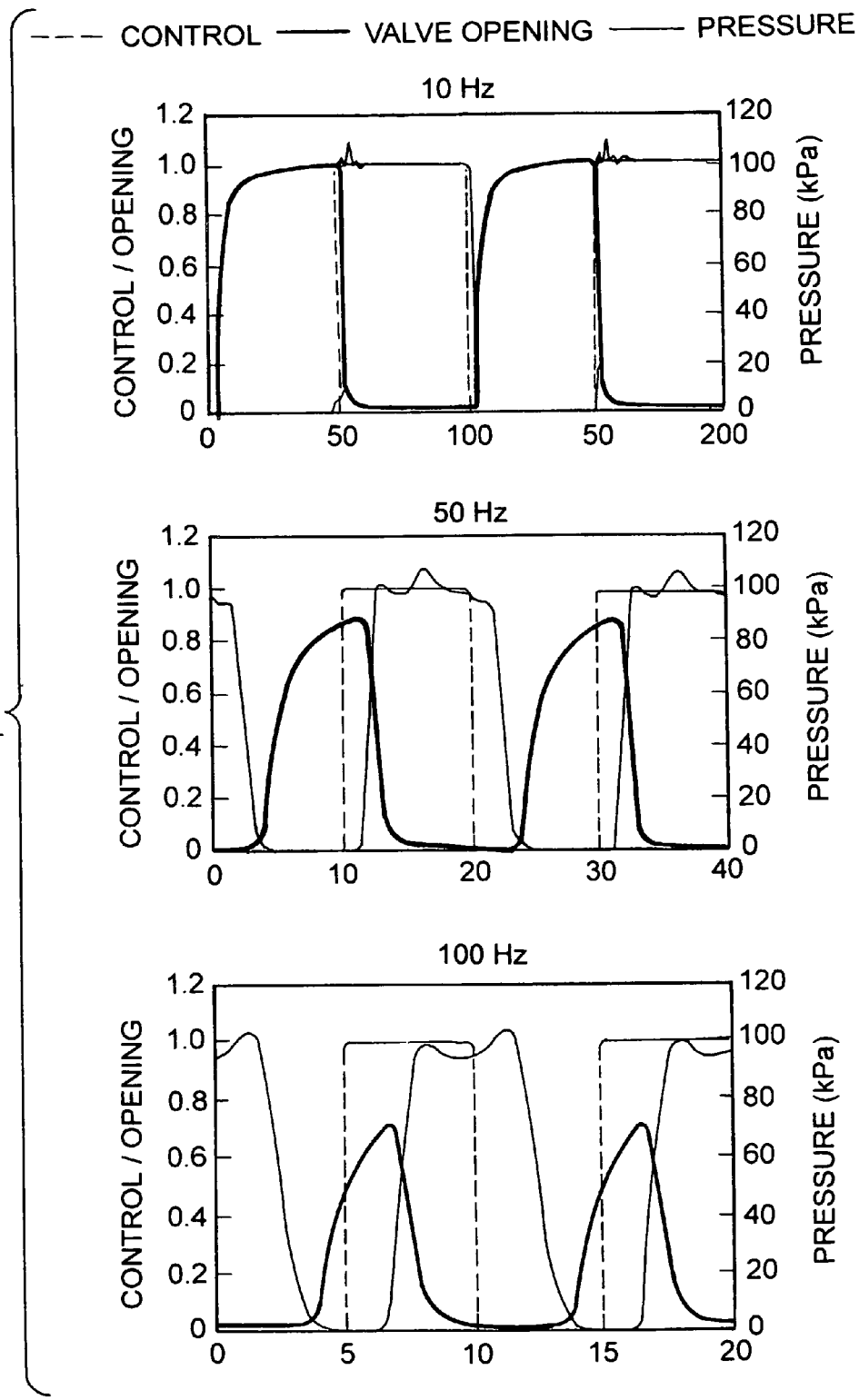
FIG. 9 illustrates time response of a 100 µm×100 µm×10 µm RTV microvalve.

FIG. 9 illustrates time response (i.e.: closure of valve as a function of time in response to a change in applied pressure) of a 100 μm×100 μm×10 μm RTV microvalve with 10-cm-long air tubing connected from the chip to a pneumatic valve as described above.

Two periods of digital control signal, actual air pressure at the end of the tubing and valve opening are shown in FIG. 9. The pressure applied on the control line is 100 kPa, which is substantially higher than the ~40 kPa required to close the valve. Thus, when closing, the valve is pushed closed with a pressure 60 kPa greater than required. When opening, however, the valve is driven back to its rest position only by its own spring force (≦40 kPa). Thus, τclose is expected to be smaller than τopen. There is also a lag between the control signal and control pressure response, due to the limitations of the miniature valve used to control the pressure. Calling such lags t and the 1/e time constants τ, the values are: topen=3.63 ms, τopen=1.88 ms, tclose=2.15 ms, τclose=0.51 ms. If 3τ each are allowed for opening and closing, the valve runs comfortably at 75 Hz when filled with aqueous solution.

If one used another actuation method which did not suffer from opening and closing lag, this valve would run at ~375 Hz. Note also that the spring constant can be adjusted by changing the membrane thickness; this allows optimization for either fast opening or fast closing. The spring constant could also be adjusted by changing the elasticity (Young's modulus) of the membrane, as is possible by introducing dopant into the membrane or by utilizing a different elastomeric material to serve as the membrane (described above in conjunction with FIGS. 7C–7H.)

When experimentally measuring the valve properties as illustrated in FIG. 9 the valve opening was measured by fluorescence. In these experiments, the flow channel was filled with a solution of fluorescein isothiocyanate (FITC) in buffer (pH≧8) and the fluorescence of a square area occupying the center ~⅓rd of the channel is monitored on an epi-fluorescence microscope with a photomultiplier tube with a 10 kHz bandwidth. The pressure was monitored with a Wheatstone-bridge pressure sensor (SenSym SCC15GD2) pressurized simultaneously with the control line through nearly identical pneumatic connections.

6. Flow Channel Cross Sections

The flow channels of the present invention may optionally be designed with different cross sectional sizes and shapes, offering different advantages, depending upon their desired application. For example, the cross sectional shape of the lower flow channel may have a curved upper surface, either along its entire length or in the region disposed under an upper cross channel). Such a curved upper surface facilitates valve sealing, as follows.

Referring to FIG. 10, a cross sectional view (similar to that of FIG. 7B) through flow channels 30 and 32 is shown. As can be seen, flow channel 30 is rectangular in cross sectional shape. In an alternate preferred aspect of the invention, as shown in FIG. 10, the cross-section of a flow channel 30 instead has an upper curved surface.

Referring first to FIG. 10, when flow channel 32 is pressurized, the membrane portion 25 of elastomeric block 24 separating flow channels 30 and 32 will move downwardly to the successive positions shown by the dotted lines 25A, 25B, 25C, 25D, and 25E. As can be seen, incomplete sealing may possibly result at the edges of flow channel 30 adjacent planar substrate 14.

In the alternate preferred embodiment of FIG. 11, flow channel 30a has a curved upper wall 25A. When flow channel 32 is pressurized, membrane portion 25 will move downwardly to the successive positions shown by dotted lines 25A2, 25A3, 25A4 and 25A5, with edge portions of the membrane moving first into the flow channel, followed by top membrane portions. An advantage of having such a curved upper surface at membrane 25A is that a more complete seal will be provided when flow channel 32 is pressurized. Specifically, the upper wall of the flow channel 30 will provide a continuous contacting edge against planar substrate 14, thereby avoiding the "island" of contact seen between wall 25 and the bottom of flow channel 30 in FIG. 10.

Figure 20:
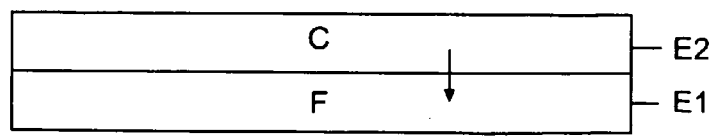
FIG. 20 shows a simplified cross-sectional view of the general microfluidic architecture of the devices of FIGS. 19A–B.

Another advantage of having a curved upper flow channel surface at membrane 25A is that the membrane can more readily conform to the shape and volume of the flow channel in response to actuation. Specifically, where a rectangular flow channel is employed, the entire perimeter (2× flow channel height, plus the flow channel width) must be forced into the flow channel. However where an arched flow channel is used, a smaller perimeter of material (only the semi-circular arched portion) must be forced into the channel. In this manner, the membrane requires less change in perimeter for actuation and is therefore more responsive to an applied actuation force to block the flow channel In an alternate aspect, (not illustrated), the bottom of flow channel 30 is rounded such that its curved surface mates with the curved upper wall 25A as seen in FIG. 20 described above.

In summary, the actual conformational change experienced by the membrane upon actuation will depend upon the configuration of the particular elastomeric structure. Specifically, the conformational change will depend upon the length, width, and thickness profile of the membrane, its attachment to the remainder of the structure, and the height, width, and shape of the flow and control channels and the material properties of the elastomer used. The conformational change may also depend upon the method of actuation, as actuation of the membrane in response to an applied pressure will vary somewhat from actuation in response to a magnetic or electrostatic force.

Moreover, the desired conformational change in the membrane will also vary depending upon the particular application for the elastomeric structure. In the simplest embodiments described above, the valve may either be open or closed, with metering to control the degree of closure of the valve. In other embodiments however, it may be desirable to alter the shape of the membrane and/or the flow channel in order to achieve more complex flow regulation. For instance, the flow channel could be provided with raised protrusions beneath the membrane portion, such that upon actuation the membrane shuts off only a percentage of the flow through the flow channel, with the percentage of flow blocked insensitive to the applied actuation force.

Many membrane thickness profiles and flow channel cross-sections are contemplated by the present invention, including rectangular, trapezoidal, circular, ellipsoidal, parabolic, hyperbolic, and polygonal, as well as sections of the above shapes. More complex cross-sectional shapes, such as the embodiment with protrusions discussed immediately above or an embodiment having concavities in the flow channel, are also contemplated by the present invention.

In addition, while the invention is described primarily above in conjunction with an embodiment wherein the walls and ceiling of the flow channel are formed from elastomer, and the floor of the channel is formed from an underlying substrate, the present invention is not limited to this particular orientation. Walls and floors of channels could also be formed in the underlying substrate, with only the ceiling of the flow channel constructed from elastomer. This elastomer flow channel ceiling would project downward into the channel in response to an applied actuation force, thereby controlling the flow of material through the flow channel. In general, monolithic elastomer structures as described elsewhere in the instant application are preferred for microfluidic applications. However, it may be useful to employ channels formed in the substrate where such an arrangement provides advantages. For instance, a substrate including optical waveguides could be constructed so that the optical waveguides direct light specifically to the side of a microfluidic channel.

7. Networked Systems

Figure 12A:
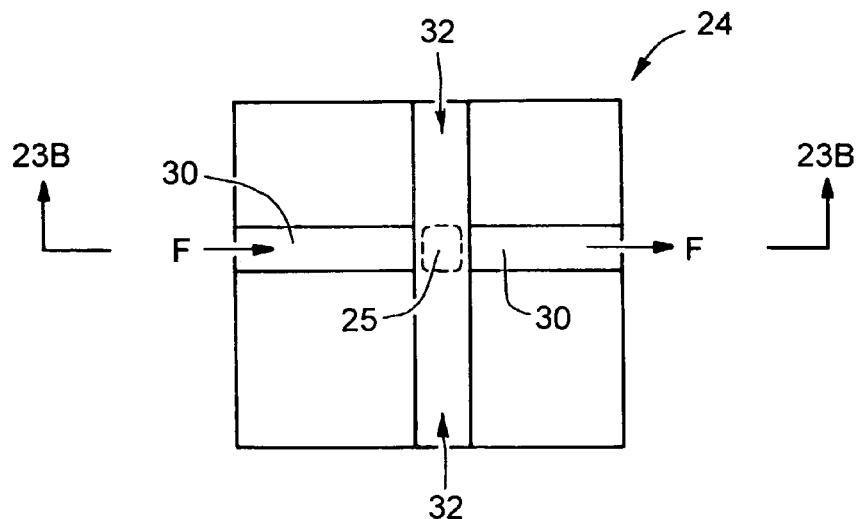
FIG. 12A is a top schematic view of an on/off valve.
Figure 13A:
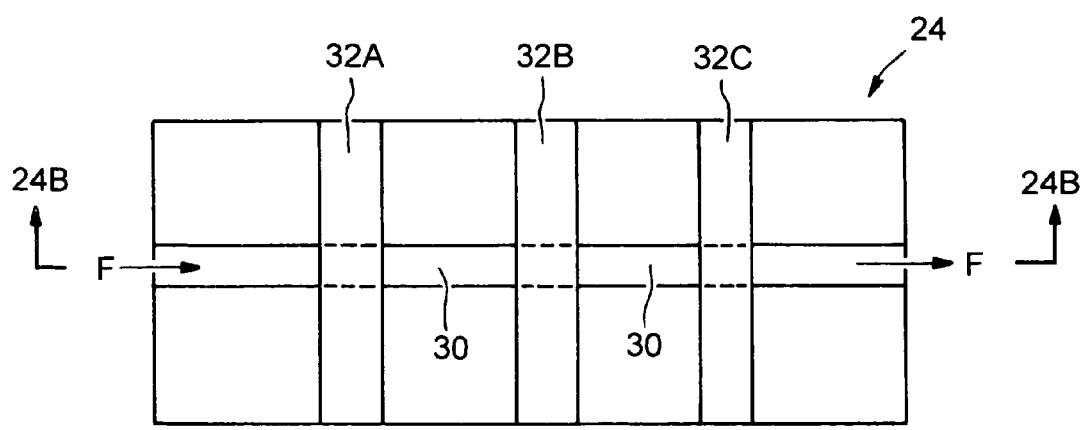
FIG. 13A is a top schematic view of a peristaltic pumping system.
Figure 12B:
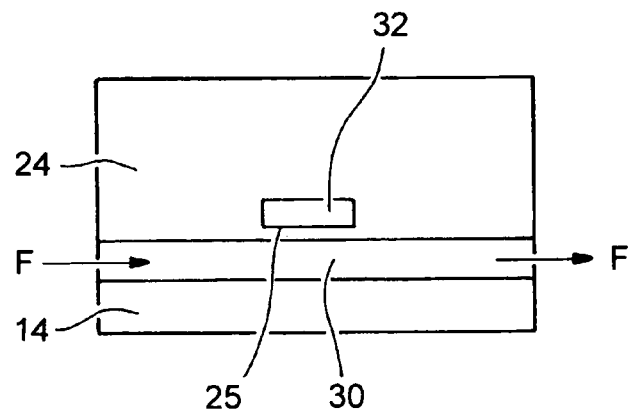
FIG. 12B is a sectional elevation view along line 23B—23B in FIG. 12A
Figure 13B:
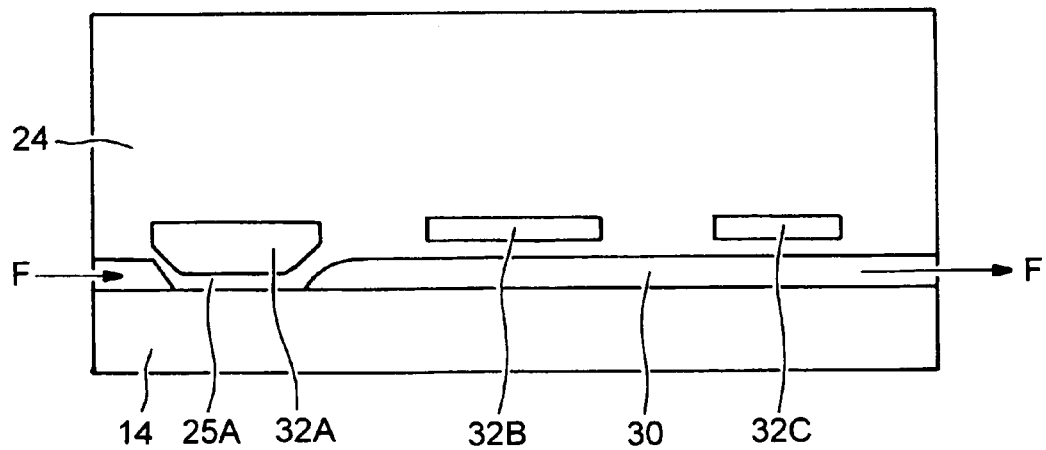
FIG. 13B is a sectional elevation view along line 24B—24B in FIG. 13A
Figure 14:
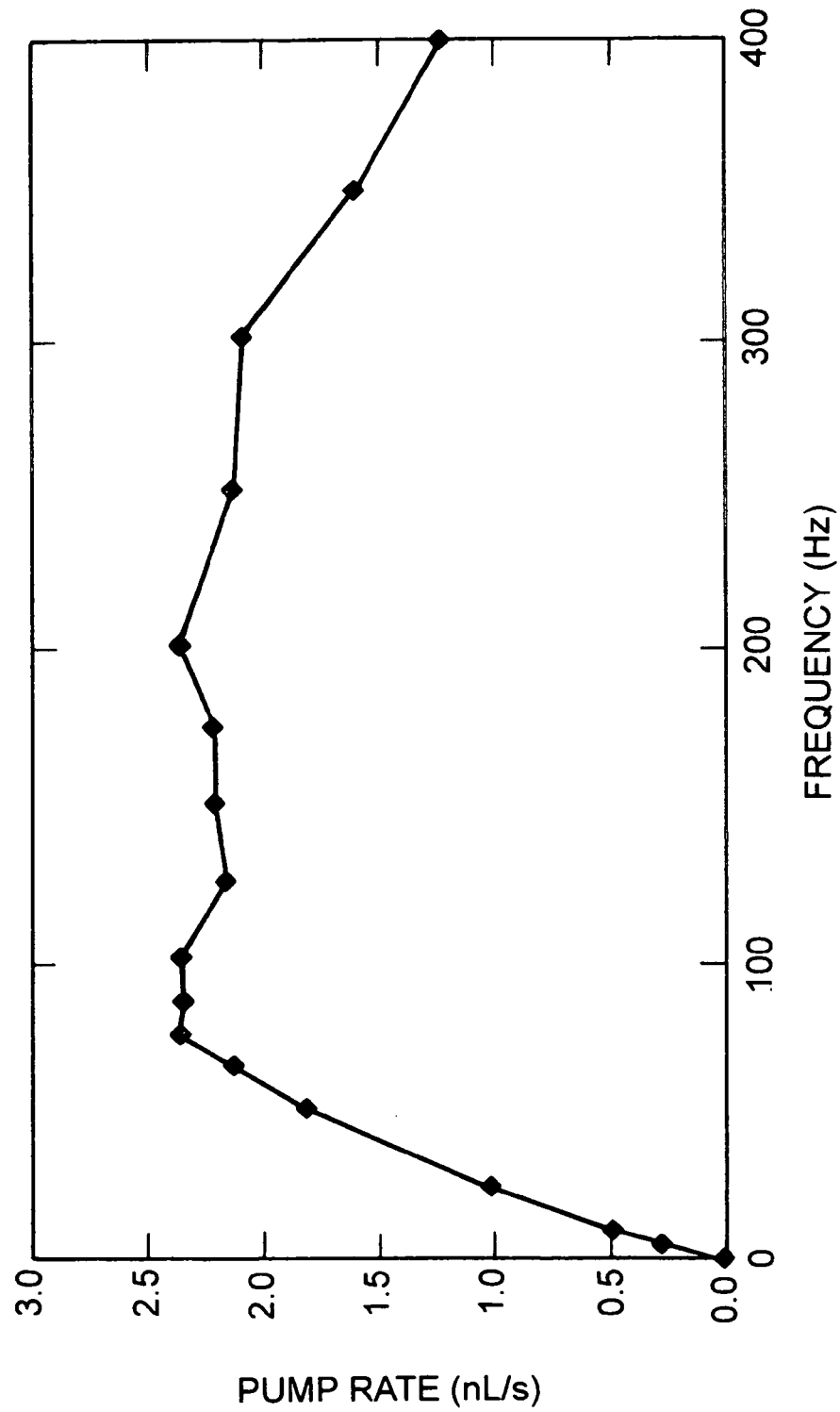
FIG. 14 is a graph showing experimentally achieved pumping rates vs. frequency for an embodiment of the peristaltic pumping system of FIG. 13.
Figure 15A:
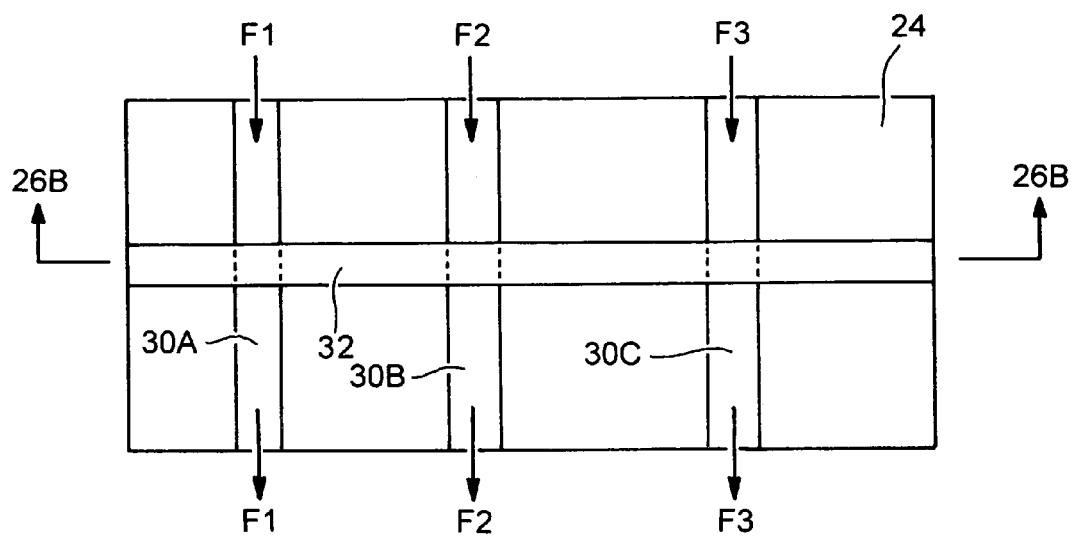
FIG. 15A is a top schematic view of one control line actuating multiple flow lines simultaneously.
Figure 15B:
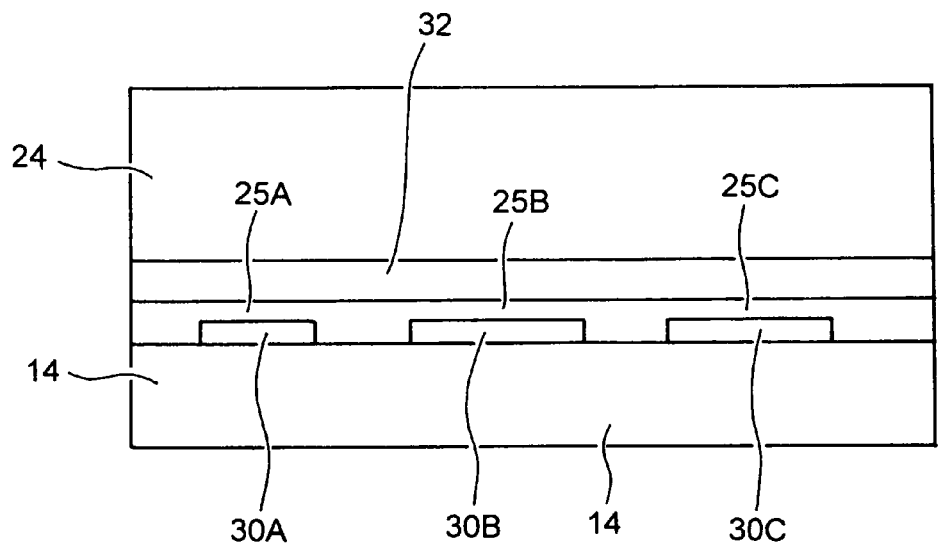
FIG. 15B is a sectional elevation view along line 26B—26B in FIG. 15A
Figure 16:
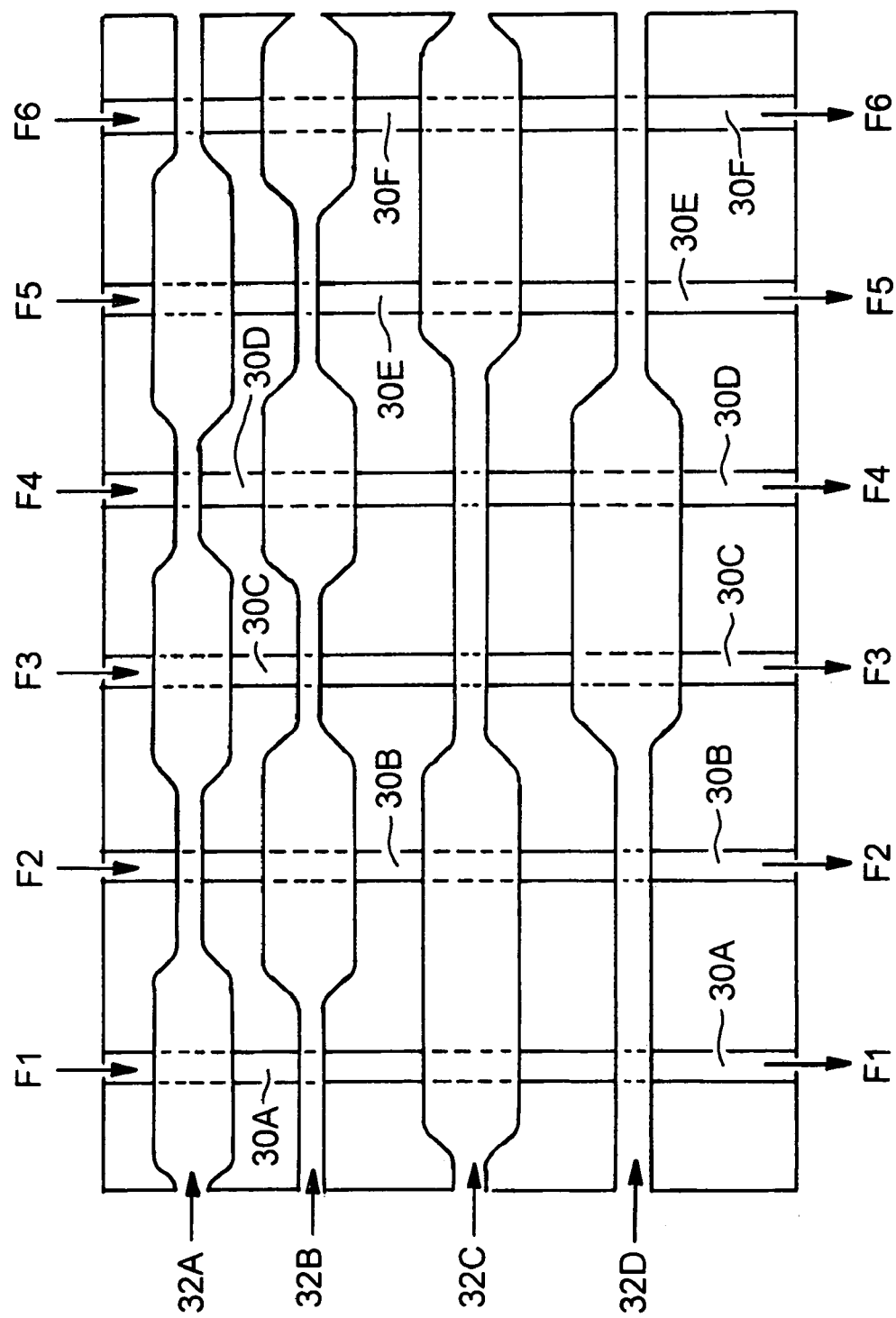
FIG. 16 is a schematic illustration of a multiplexed system adapted to permit flow through various channels.

FIGS. 12A and 12B show a views of a single on/off valve, identical to the systems set forth above, (for example in FIG. 7A). FIGS. 13A and 13B shows a peristaltic pumping system comprised of a plurality of the single addressable on/off valves as seen in FIG. 12, but networked together. FIG. 14 is a graph showing experimentally achieved pumping rates vs. frequency for the peristaltic pumping system of FIG. 13. FIGS. 15A and 15B show a schematic view of a plurality of flow channels which are controllable by a single control line. This system is also comprised of a plurality of the single addressable on/off valves of FIG. 12, multiplexed together, but in a different arrangement than that of FIG. 12. FIG. 16 is a schematic illustration of a multiplexing system adapted to permit fluid flow through selected channels, comprised of a plurality of the single on/off valves of FIG. 12, joined or networked together.

Referring first to FIGS. 12A and 12B, a schematic of flow channels 30 and 32 is shown. Flow channel 30 preferably has a fluid (or gas) flow F passing therethrough. Flow channel 32, (which crosses over flow channel 30, as was already explained herein), is pressurized such that membrane 25 separating the flow channels may be depressed into the path of flow channel 30, shutting off the passage of flow F therethrough, as has been explained. As such, "flow channel" 32 can also be referred to as a "control line" which actuates a single valve in flow channel 30. In FIGS. 12 to 15, a plurality of such addressable valves are joined or networked together in various arrangements to produce pumps, capable of peristaltic pumping, and other fluidic logic applications.

Referring to FIGS. 13A and 13B, a system for peristaltic pumping is provided, as follows. A flow channel 30 has a plurality of generally parallel flow channels (i.e.: control lines) 32A, 32B and 32C passing thereover. By pressurizing control line 32A, flow F through flow channel 30 is shut off under membrane 25A at the intersection of control line 32A and flow channel 30. Similarly, (but not shown), by pressurizing control line 32B, flow F through flow channel 30 is shut off under membrane 25B at the intersection of control line 32B and flow channel 30, etc.

Each of control lines 32A, 32B, and 32C is separately addressable. Therefore, peristalsis may be actuated by the pattern of actuating 32A and 32C together, followed by 32A, followed by 32A and 32B together, followed by 32B, followed by 32B and C together, etc. This corresponds to a successive "101, 100, 110, 010, 011, 001" pattern, where "0" indicates "valve open" and "1" indicates "valve closed." This peristaltic pattern is also known as a 120° pattern (referring to the phase angle of actuation between three valves). Other peristaltic patterns are equally possible, including 60° and 90° patterns.

In experiments performed by the inventors, a pumping rate of 2.35 nL/s was measured by measuring the distance traveled by a column of water in thin (0.5 mm i.d.) tubing; with 100×100×10 µm valves under an actuation pressure of 40 kPa. The pumping rate increased with actuation frequency until approximately 75 Hz, and then was nearly constant until above 200 Hz. The valves and pumps are also quite durable and the elastomer membrane, control channels, or bond have never been observed to fail. In experiments performed by the inventors, none of the valves in the peristaltic pump described herein show any sign of wear or fatigue after more than 4 million actuations. In addition to their durability, they are also gentle. A solution of E. Coli pumped through a channel and tested for viability showed a 94% survival rate.

FIG. 14 is a graph showing experimentally achieved pumping rates vs. frequency for the peristaltic pumping system of FIG. 13.

FIGS. 15A and 15B illustrates another way of assembling a plurality of the addressable valves of FIG. 12. Specifically, a plurality of parallel flow channels 30A, 30B, and 30C are provided. Flow channel (i.e.: control line) 32 passes thereover across flow channels 30A, 30B, and 30C. Pressurization of control line 32 simultaneously shuts off flows F1, F2 and F3 by depressing membranes 25A, 25B, and 25C located at the intersections of control line 32 and flow channels 30A, 30B, and 30C.

FIG. 16 is a schematic illustration of a multiplexing system adapted to selectively permit fluid to flow through selected channels, as follows. The downward deflection of membranes separating the respective flow channels from a control line passing thereabove (for example, membranes 25A, 25B, and 25C in FIGS. 15A and 15B) depends strongly upon the membrane dimensions. Accordingly, by varying the widths of flow channel control line 32 in FIGS. 15A and 15B, it is possible to have a control line pass over multiple flow channels, yet only actuate (i.e.: seal) desired flow channels. FIG. 16 illustrates a schematic of such a system, as follows.

A plurality of parallel flow channels 30A, 30B, 30C, 30D, 30E and 30F are positioned under a plurality of parallel control lines 32A, 32B, 32C, 32D, 32E and 32F. Control channels 32A, 32B, 32C, 32D, 32E and 32F are adapted to shut off fluid flows F1, F2, F3, F4, F5 and F6 passing through parallel flow channels 30A, 30B, 30C, 30D, 30E and 30F using any of the valving systems described above, with the following modification.

Each of control lines 32A, 32B, 32C, 32D, 32E and 32F have both wide and narrow portions. For example, control line 32A is wide in locations disposed over flow channels 30A, 30C and 30E. Similarly, control line 32B is wide in locations disposed over flow channels 30B, 30D and 30F, and control line 32C is wide in locations disposed over flow channels 30A, 30B, 30E and 30F.

At the locations where the respective control line is wide, its pressurization will cause the membrane (25) separating the flow channel and the control line to depress significantly into the flow channel, thereby blocking the flow passage therethrough. Conversely, in the locations where the respective control line is narrow, membrane (25) will also be narrow. Accordingly, the same degree of pressurization will not result in membrane (25) becoming depressed into the flow channel (30). Therefore, fluid passage thereunder will not be blocked.

For example, when control line 32A is pressurized, it will block flows F1, F3 and F5 in flow channels 30A, 30C and 30E. Similarly, when control line 32C is pressurized, it will block flows F1, F2, F5 and F6 in flow channels 30A, 30B, 30E and 30F. As can be appreciated, more than one control line can be actuated at the same time. For example, control lines 32A and 32C can be pressurized simultaneously to block all fluid flow except F4 (with 32A blocking F1, F3 and F5; and 32C blocking F1, F2, F5 and F6).

By selectively pressurizing different control lines (32) both together and in various sequences, a great degree of fluid flow control can be achieved. Moreover, by extending the present system to more than six parallel flow channels (30) and more than four parallel control lines (32), and by varying the positioning of the wide and narrow regions of the control lines, very complex fluid flow control systems may be fabricated. A property of such systems is that it is possible to turn on any one flow channel out of n flow channels with only 2(log2n) control lines.

8. Switchable Flow Arrays

Figure 17A:
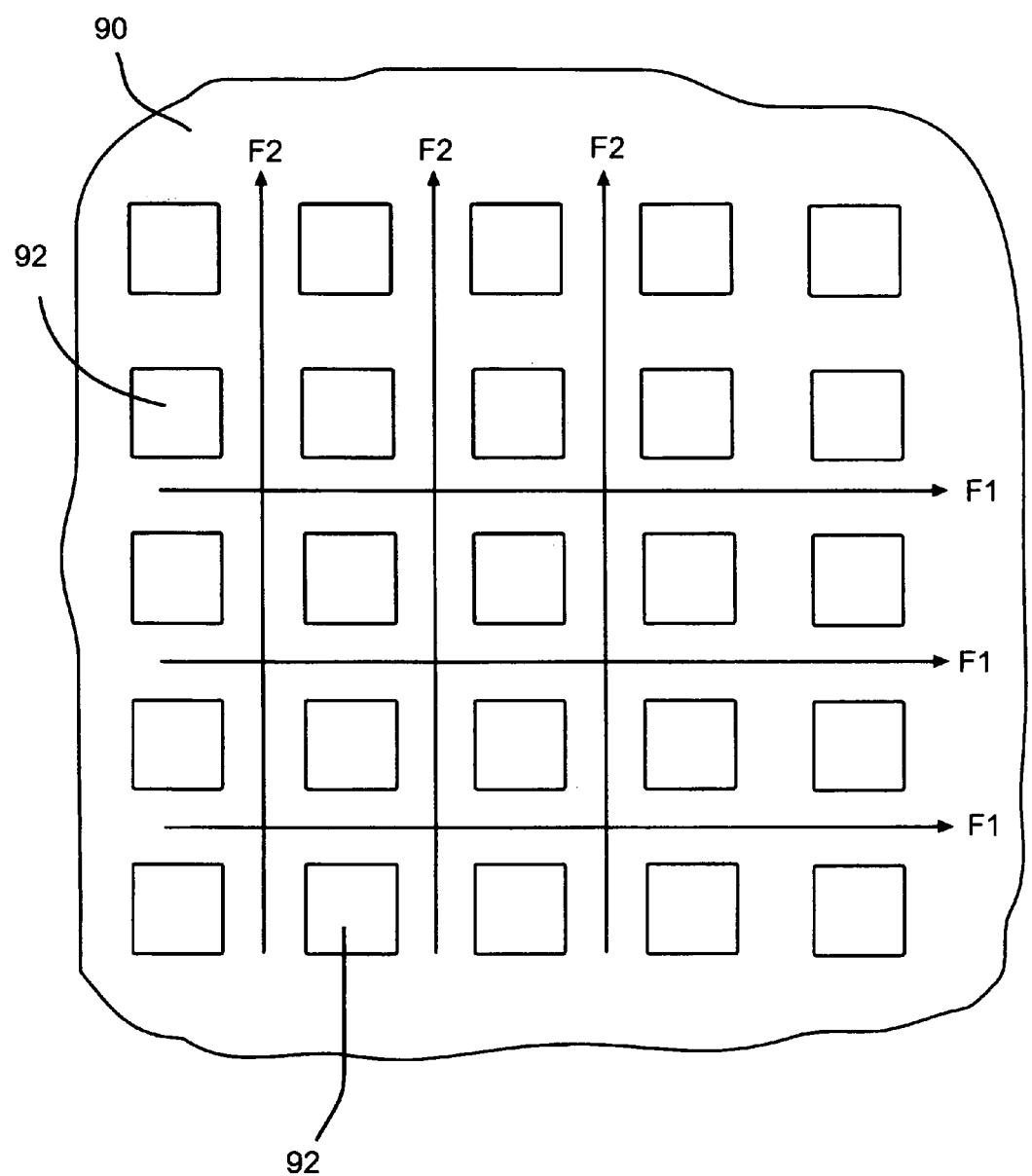
FIGS. 17A–D show plan views of one embodiment of a switchable flow array.

In yet another novel embodiment, fluid passage can be selectively directed to flow in either of two perpendicular directions. An example of such a "switchable flow array" system is provided in FIGS. 17A to 17D. FIG. 17A shows a bottom view of a first layer of elastomer 90, (or any other suitable substrate), having a bottom surface with a pattern of recesses forming a flow channel grid defined by an array of solid posts 92, each having flow channels passing therearound.

Figure 17B:
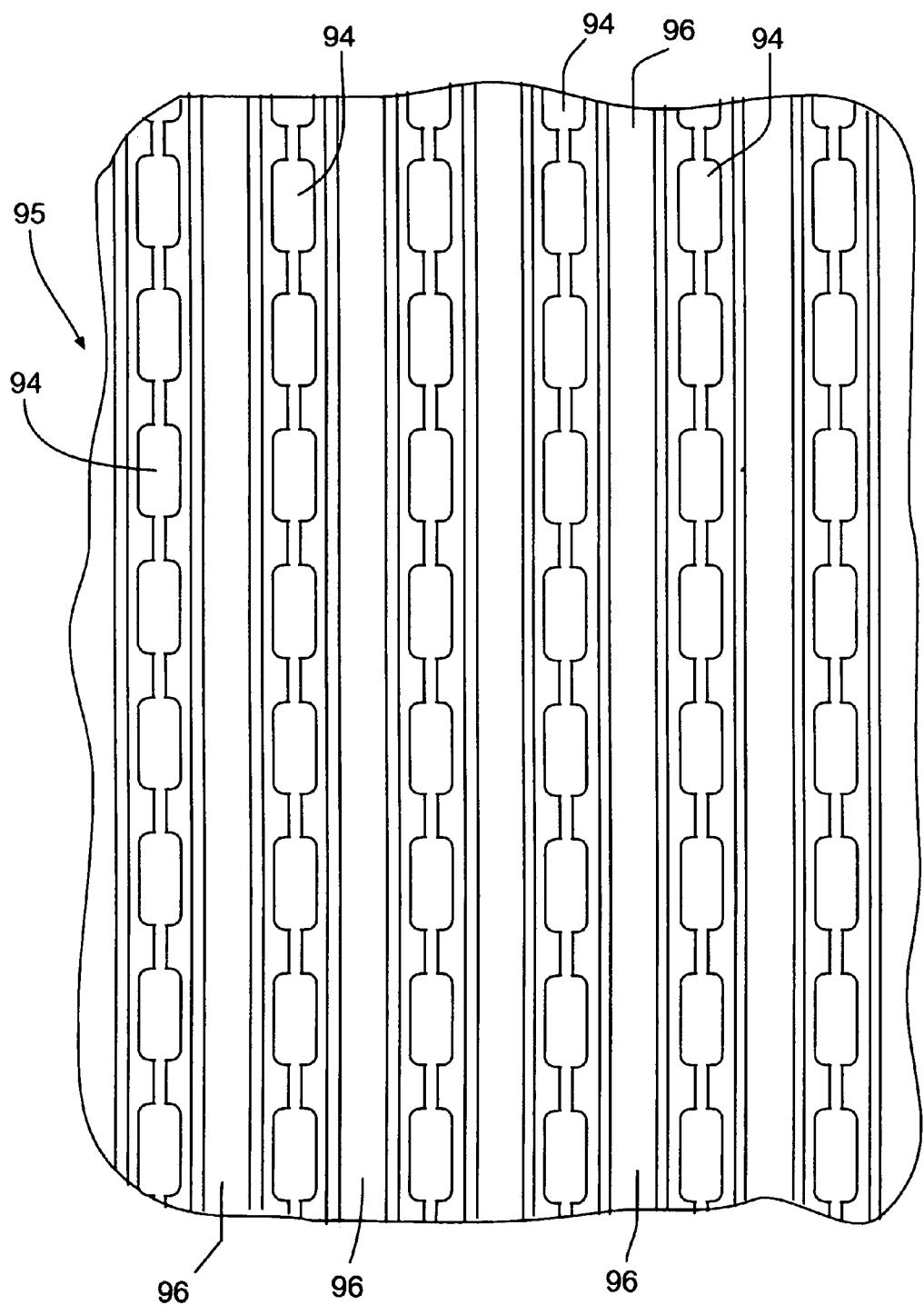

In preferred aspects, an additional layer of elastomer is bound to the top surface of layer 90 such that fluid flow can be selectively directed to move either in direction F1, or perpendicular direction F2. FIG. 17B is a bottom view of the bottom surface of the second layer of elastomer 95 showing recesses formed in the shape of alternating "vertical" control lines 96 and "horizontal" control lines 94. "Vertical" control lines 96 have the same width therealong, whereas "horizontal" control lines 94 have alternating wide and narrow portions, as shown.

Figure 17C:
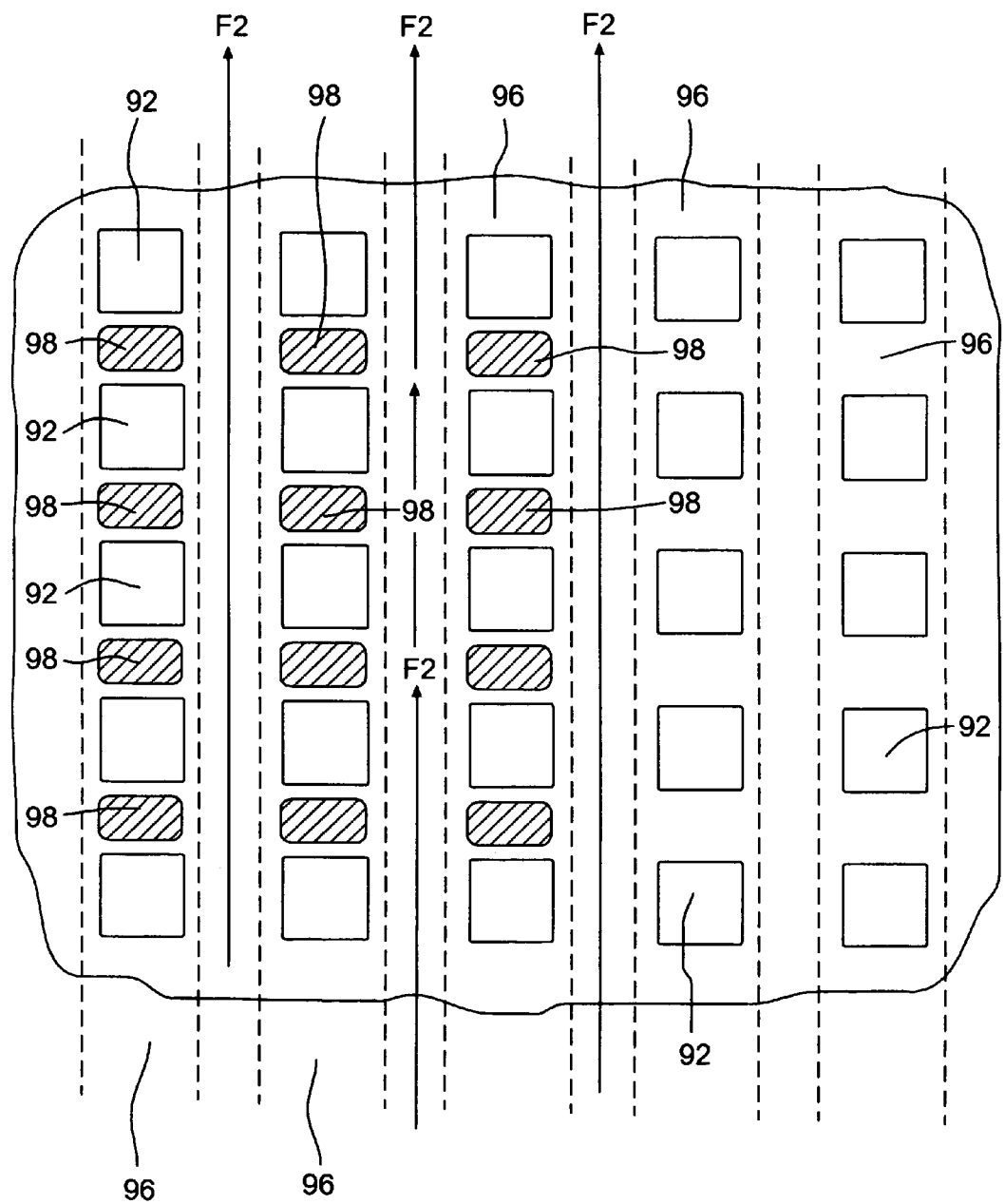
Figure 17D:
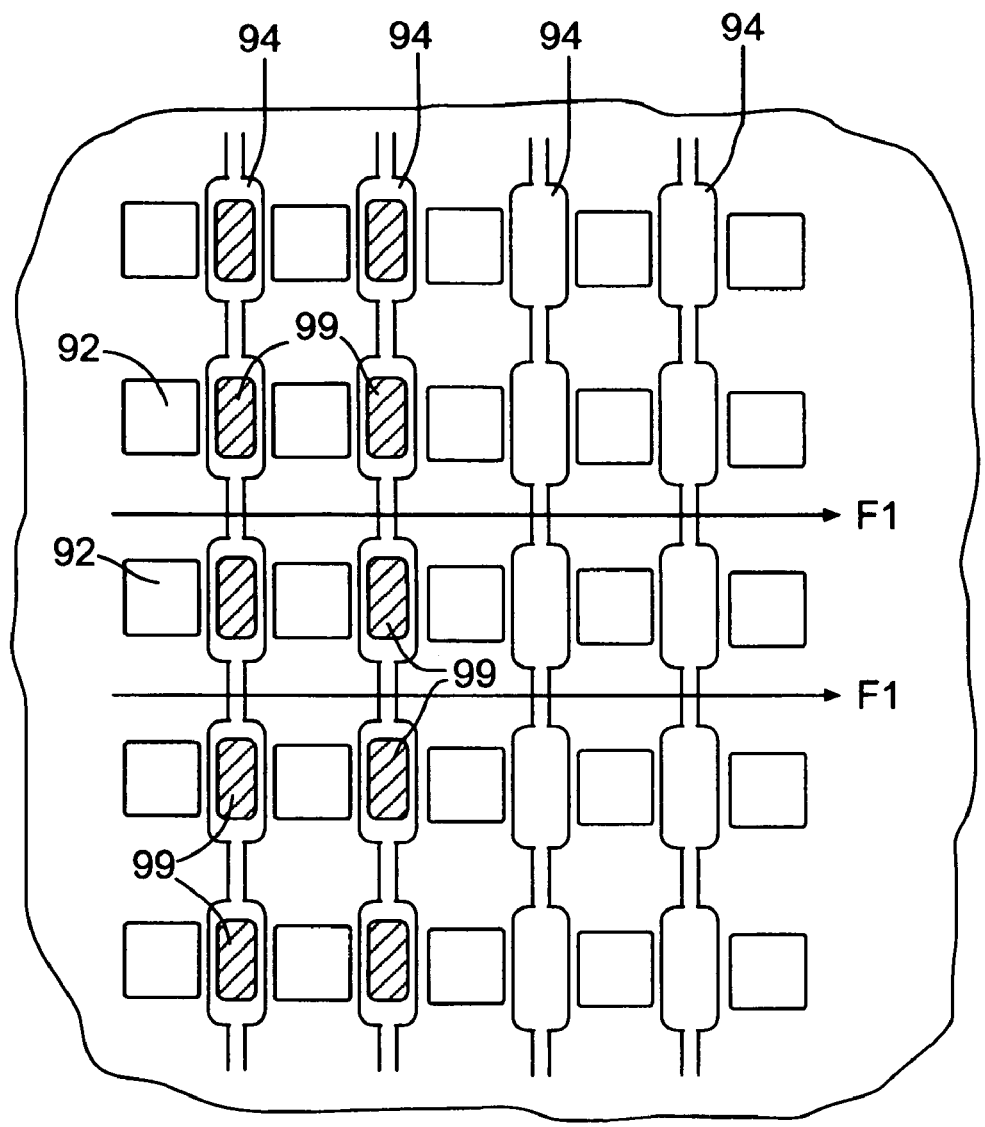

Elastomeric layer 95 is positioned over top of elastomeric layer 90 such that "vertical" control lines 96 are positioned over posts 92 as shown in FIG. 17C and "horizontal" control lines 94 are positioned with their wide portions between posts 92, as shown in FIG. 17D.

As can be seen in FIG. 17C, when "vertical" control lines 96 are pressurized, the membrane of the integrated structure formed by the elastomeric layer initially positioned between layers 90 and 95 in regions 98 will be deflected downwardly over the array of flow channels such that flow in only able to pass in flow direction F2 (i.e.: vertically), as shown.

As can be seen in FIG. 17D, when "horizontal" control lines 94 are pressurized, the membrane of the integrated structure formed by the elastomeric layer initially positioned between layers 90 and 95 in regions 99 will be deflected downwardly over the array of flow channels, (but only in the regions where they are widest), such that flow in only able to pass in flow direction F1 (i.e.: horizontally), as shown.

The design illustrated in FIGS. 17A–D allows a switchable flow array to be constructed from only two elastomeric layers, with no vertical vias passing between control lines in different elastomeric layers required. If all vertical flow control lines 94 are connected, they may be pressurized from one input. The same is true for all horizontal flow control lines 96.

9. Cell Pen

In yet a further application of the present invention, an elastomeric structure can be utilized to manipulate organisms or other biological material. FIGS. 18A-18D show plan views of one embodiment of a cell pen structure in accordance with the present invention.

Cell pen array 4400 features an array of orthogonally-oriented flow channels 4402, with an enlarged "pen" structure 4404 at the intersection of alternating flow channels. Valve 4406 is positioned at the entrance and exit of each pen structure 4404. Peristaltic pump structures 4408 are positioned on each horizontal flow channel and on the vertical flow channels lacking a cell pen structure.

Figure 18A:
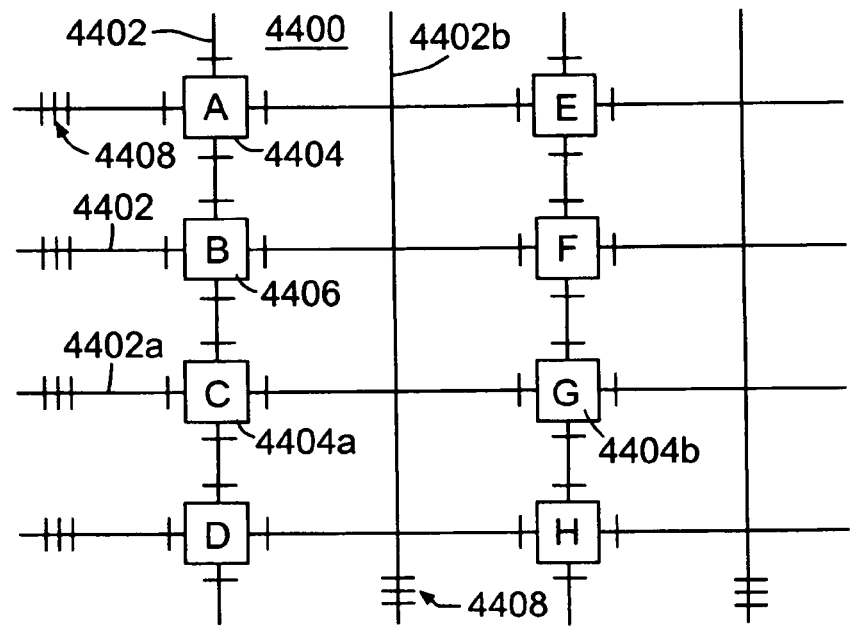
FIGS. 18A–D show plan views of one embodiment of a cell pen array structure.
Figure 18B:
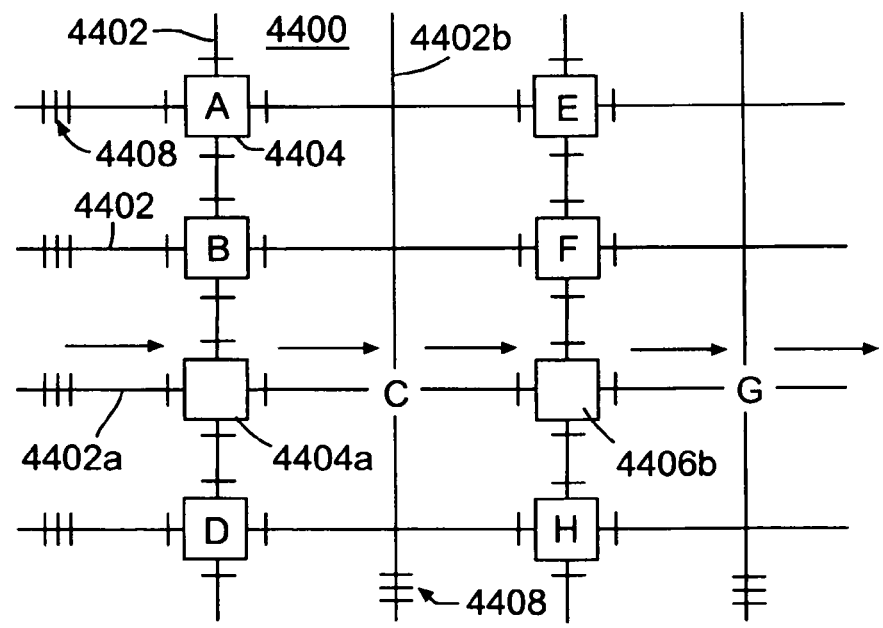
Figure 18C:
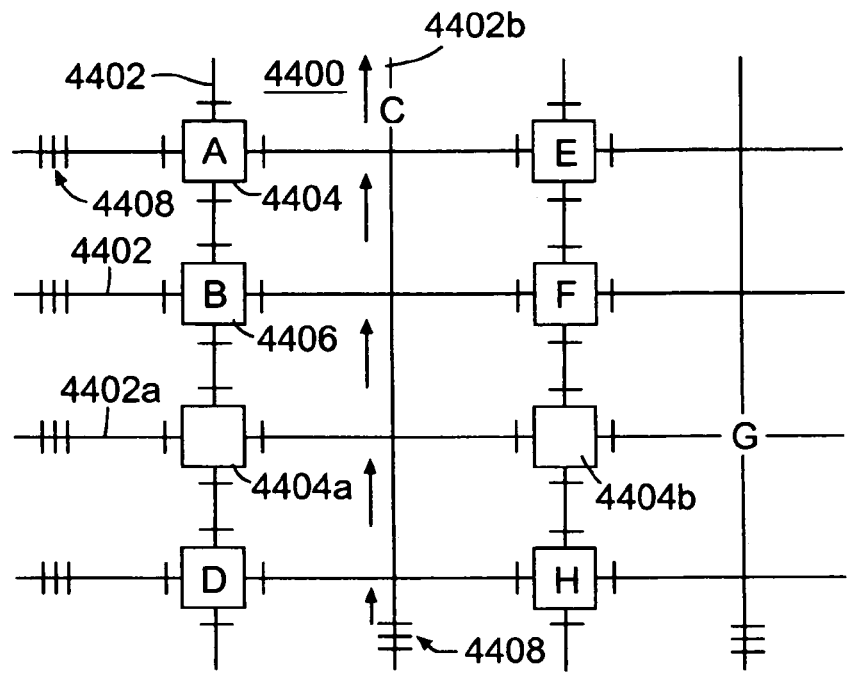
Figure 18D:
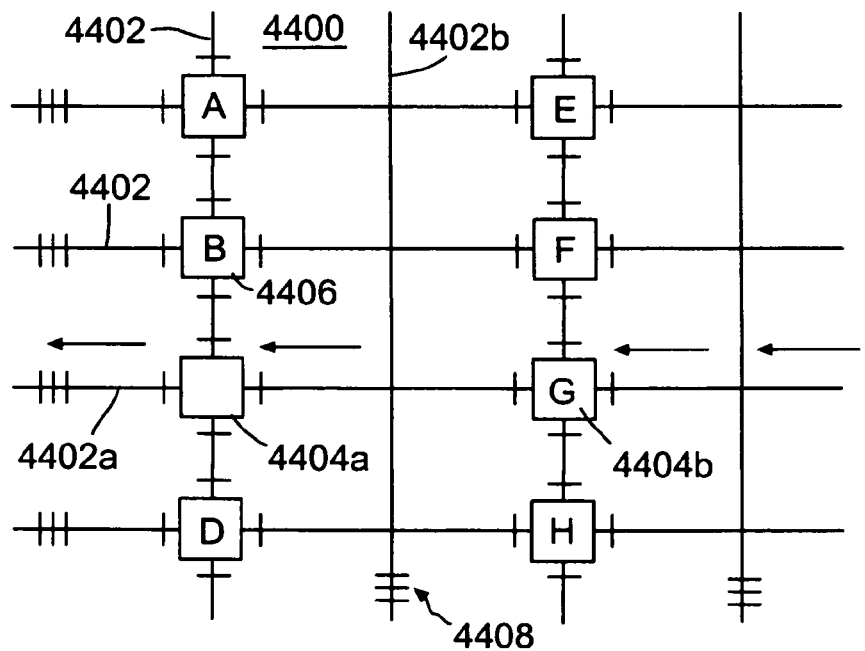

Cell pen array 4400 of FIG. 18A has been loaded with cells A–H that have been previously sorted. FIGS. 18B–18C show the accessing and removal of individually stored cell C by 1) opening valves 4406 on either side of adjacent pens 4404a and 4404b, 2) pumping horizontal flow channel 4402a to displace cells C and G, and then 3) pumping vertical flow channel 4402b to remove cell C. FIG. 18D shows that second cell G is moved back into its prior position in cell pen array 4400 by reversing the direction of liquid flow through horizontal flow channel 4402a. The cell pen array 4404 described above is capable of storing materials within a selected, addressable position for ready access.

While the embodiment shown and described above in connection with FIGS. 18A–18D utilizes linked valve pairs on opposite sides of the flow channel intersections, this is not required by the present invention. Other configurations, including linking of adjacent valves of an intersection, or independent actuation of each valve surrounding an intersection, are possible to provide the desired flow characteristics. With the independent valve actuation approach however, it should be recognized that separate control structures would be utilized for each valve, complicating device layout.

II. Microfluidic Large-Scale Integration

The previous section has described monolithic microvalves that are substantially leakproof and scalable, and has also described methods for fabricating these microvalves. For the relatively simple arrays of microfluidic valves previously described, each fluid flow channel may be controlled by its own individual valve control channel. However, such a non-integrated control strategy cannot be practicably implemented for more complex arrays comprising thousands or even tens of thousands of individually addressable valves. Accordingly, embodiments of the present invention provide a variety of techniques which may be applied alone or in combination to allow for the fabrication of large scale integrated microfluidic devices having individually addressable valves.

1. Control of Flow Lines by Multiplexor

Figure 19A:
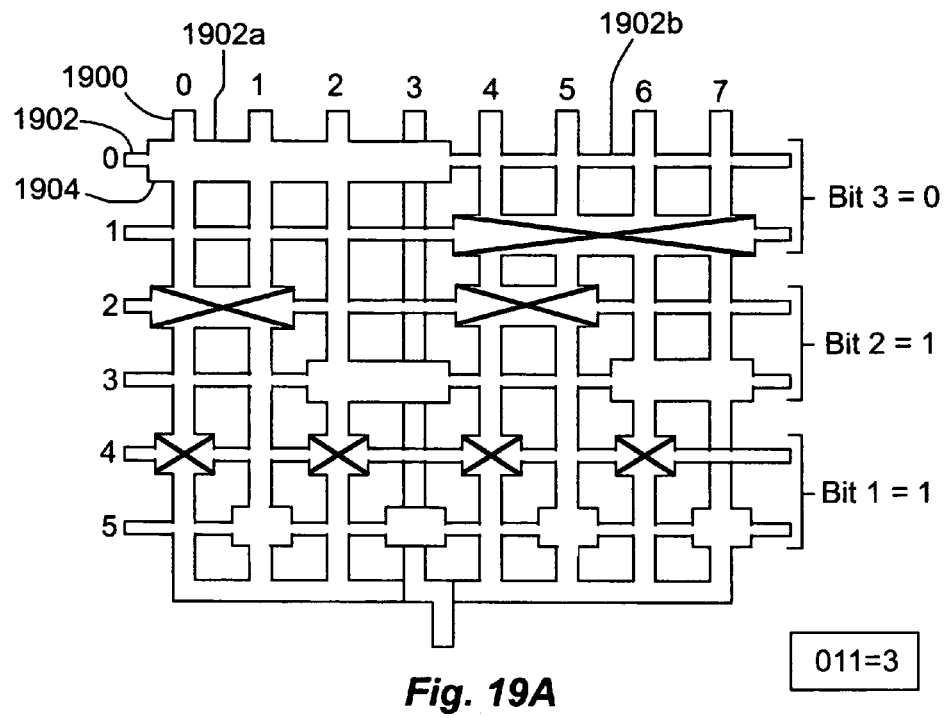
FIG. 19A shows a simplified plan view illustrating a binary tree microfluidic multiplexor operational diagram.

The use of multiplexor structures has previously been described in connection with a single set of control lines overlying a single set of flow channels. FIG. 19A shows a simplified plan view illustrating a microfluidic binary tree multiplexor operational diagram. Flow channels 1900 defined in a lower elastomer layer contain the fluid of interest, while control channels 1902 defined in an overlying elastomer layer represent control lines containing an actuation fluid such as air or water. Valves 1904 are defined by the membranes formed at the intersection of the wider portion 1902a of a control channel 1902 with a flow channel 1900. The actuation pressure is chosen so that only the wide membranes are fully deflected into the flow channel 1900. Specifically, the multiplexor structure is based on the sharp increase in pressure required to actuate a valve as the ratio of control channel width:flow channel width is decreased.

The multiplexor structure shown in FIG. 19A is in the form of a binary tree of valves where each stage selects one out of two total groups of flow channels. In the multiplexor embodiment shown in FIG. 19A, each combination of open/closed valves in the multiplexor selects for a single channel, so that n flow channels can be addressed with only $2\log_2 n$ control channels.

By using multiplexed valve systems, the power of the binary system becomes evident: only about 20 control channels are required to specifically address 1024 flow channels. This allows a large number of elastomeric microvalves to perform complex fluidic manipulations within these devices, while the interface between the device and the external environment is simple and robust.

Figure 19B:
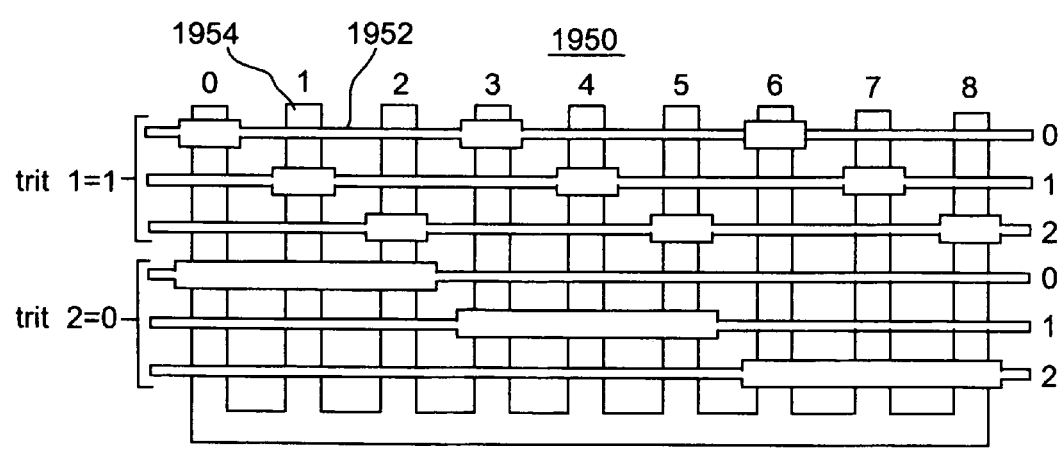
FIG. 19B shows a simplified plan view illustrating a tertiary tree microfluidic multiplexor operational diagram.

FIG. 19B shows a simplified plan view of an alternative embodiment of a multiplexor structure in accordance with the present invention. Multiplexor structure 1950 comprises control channels 1952 formed in an elastomer layer overlying flow channels 1954 of an underlying elastomer layer. Operating under the same physical principles of the multiplexor of FIG. 19A, multiplexor 1950 comprises a tertiary tree of valves, where each stage comprises three bits ("a trit") and selects one out of three total groups of flow channels. Each combination of open/closed valves in the multiplexor 1950 selects for a single channel, so that n flow channels can be addressed with only $3\log_3 n$ control channels.

The general microfluidic flow architecture of either of the basic multiplexor devices shown in FIGS. 19A–B may be generically represented in the simplified cross-sectional view of FIG. 20, wherein second elastomer layer E2 defining control channel network C overlies first elastomer layer E1 defining flow channel network F.

The base 3 multiplexor of FIG. 19B is the most efficient design that may be used to address large numbers of "flow" channels. This is because the $x \log_x n$ valve is minimized where e is used for the base of the log. As fractions are not used for the base of an actual multiplexor, the most efficient multiplexor structure is achieved where the value of x=3, the integer closest to e (~2.71828).

To highlight this point, Table 1 compares the efficiency of the base 2 multiplexor with the base 3 multiplexor.

TABLE 1

| Number of Control Lines | Number of Flow Lines Controlled by Control Lines | | Enhanced Efficiency of Base 3 Multiplexor Structure |
|---|---|---|---|
| | Base 2 Multiplexor | Base 3 Multiplexor | |
| 6 | 8 | 9 | +1 |
| 9 | 23 | 27 | +4 |
| 12 | 64 | 81 | +17 |
| 15 | 181 | 243 | +62 |
| 18 | 512 | 729 | +217 |

While the above description has focused upon various multiplexor structures utilizing stages having the same base number, this is not required by the present invention. Alternative embodiments of multiplexor structures in accordance with the present invention may comprise stages of unlike base numbers. For example, a two-stage plexor consisting of a bit stage and a trit stage represents the most efficient way of addressing six flow channels. The order of the stages is arbitrary, and will always result in the same number of flow lines being controlled. The use of multiplexor structures comprising different binary and tertiary stages allows the efficient addressing of any number of "flow" channels that are the product of the numbers 2 and 3.

Figure 33:
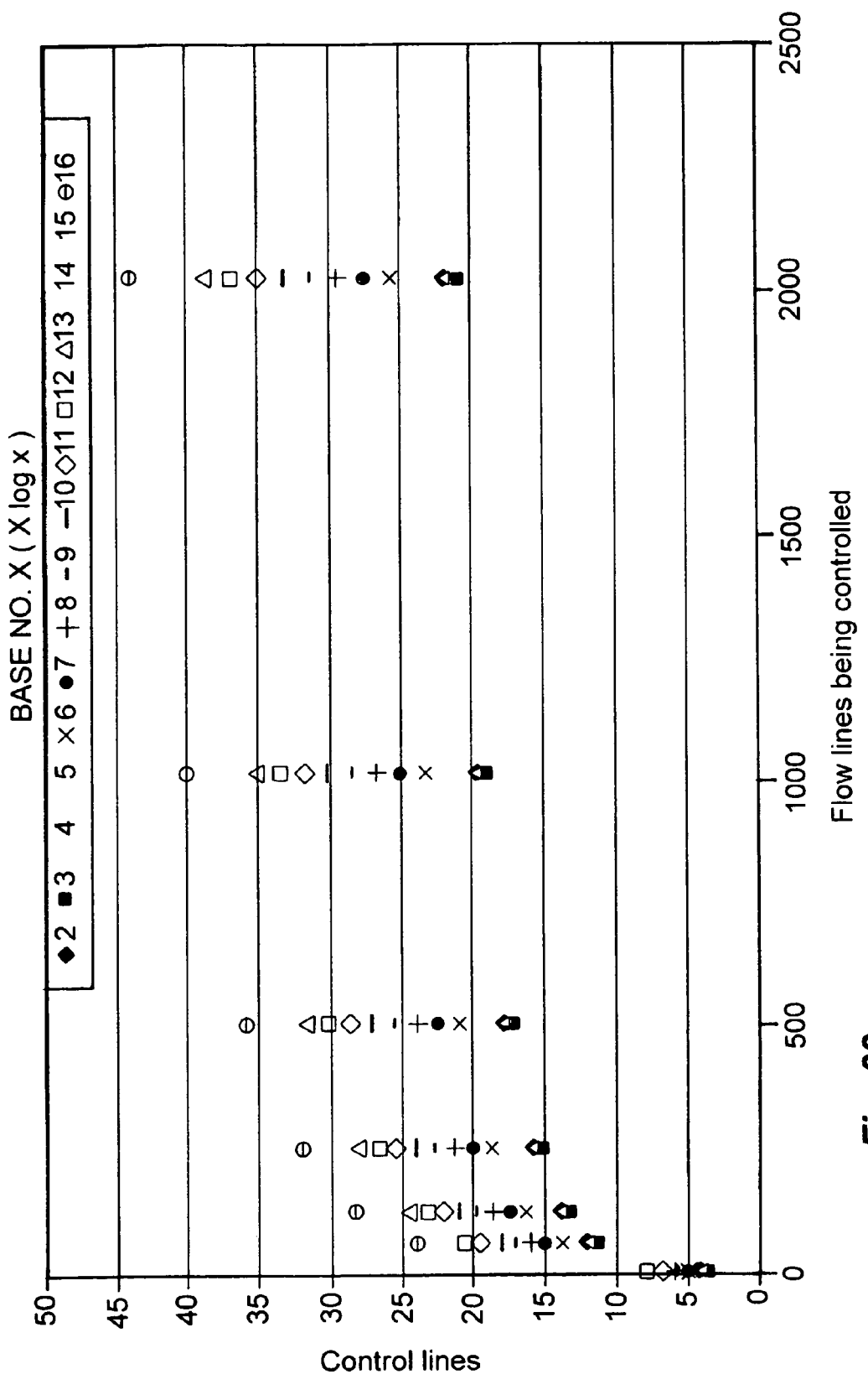
FIG. 33 plots the number of control lines versus the number of flow lines being controlled, for various base n multiplexer structures.

A multiplexor may conceivably use any base number. For example, five may also be used as the base number, if necessary. However, efficiency in utilization of control lines diminishes as the number of control lines moves away from the value of e. This is shown in FIG. 33, which plots the number of control lines versus the number of flow lines being controlled, for multiplexor structures having different base numbers.

The standard multiplexor structures previously shown and described a suitable for many applications. However, alternative embodiments of multiplexor structures may offer enhanced performance in certain situations.

Figure 28:
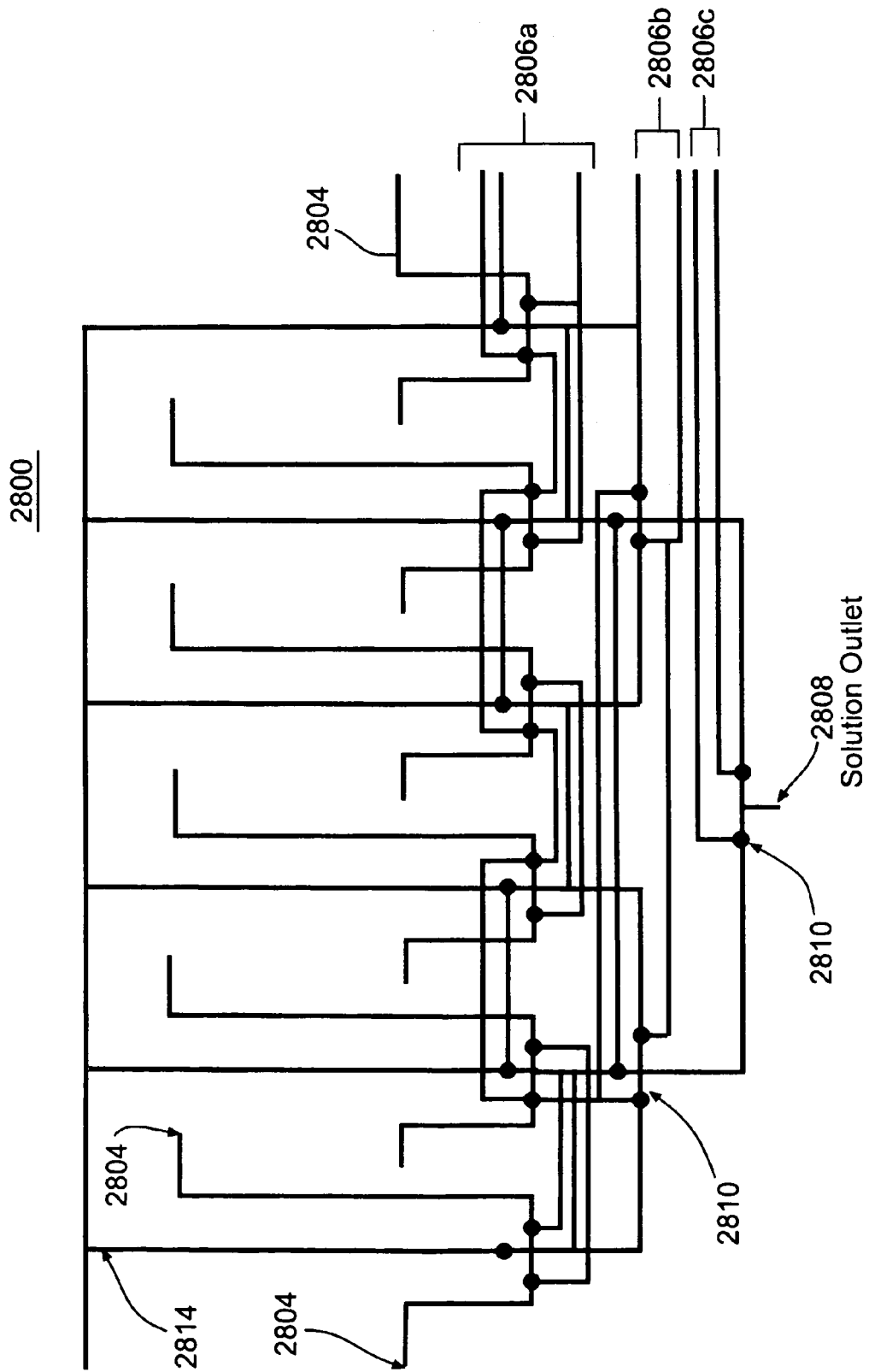
FIG. 28 shows a simplified plan view of an embodiment of a modified multiplexor in accordance with the present invention.

For example, where several fluid inputs are to be selected and introduced serially into other regions of a chip, unwanted cross-contamination attributable to dead volumes between valves can occur. Accordingly, FIG. 28 shows a simplified plan view of an alternative embodiment of a multiplexor structure of the present invention, which features a minimum of dead volume.

Specifically, multiplexor 2800 comprises a flow channel network 2802 having sample inputs 2804 arranged in the shape of a fluidic input tree. Control lines 2806 are arranged in three stages, with first and second tertiary states 2806a and 2806b, and binary stage 2806c control lines access of the flowed fluid to outlet 2808 of the flow channel network. The control lines 2806 are positioned to locate control valves 2810 as close as possible to each flow channel junction in order to minimize dead volumes. Additionally, a final input line 2814 of every multiplexor is allocated to receive a buffer, thereby allowing cleaning of the contents of the flow channels and flow channel junctions.

2. Control of Control Lines by Other Control Lines

One technique allowing for the fabrication of large scale integrated (LSI) microfluidic devices is the use of multiple layers of control lines. FIGS. 21–21B illustrate this approach. FIG. 21 shows a plan view of one embodiment of a microfluidic device having a first control line controlled by a second control line. FIG. 21A shows a cross-sectional view of the microfluidic device of FIG. 21, taken along line 21A–21A'. FIG. 21B shows a cross-sectional view of the microfluidic device of FIG. 21, taken along line 21B–21B'.

Microfluidic structure 2100 comprises two flow channels 2102a-b formed in lowermost elastomer layer 2104. First control channel network 2106 including first inlet 2106a in fluid communication with first and second branches 2106b and 2106c, is formed in a second elastomer layer 2108 overlying first elastomer layer 2104. First branch 2106b of first control channel network 2106 includes widened portion 2110 overlying first flow channel 2102a to define first valve 2112. Second branch 2106c of first control channel network 2106 includes widened portion 2114 overlying second flow channel 2102b to define second valve 2116.

Second control channel network 2118 comprising third control channel 2118a is formed in third elastomer layer 2120 overlying second elastomer layer 2108. Third control channel 2118a includes widened portion 2118b overlying first branch 2106b of first control channel network 2106 to form valve 2122.

The microfluidic device illustrated in FIGS. 21–21B may be operated as follows. A fluid that is to be manipulated is present in flow channels 2102a and 2102b. Application of a pressure to the first control channel network 2106 causes the membranes of valves 2112 and 2116 to deflect downward into their respective flow channels 2102a and 2102b, thereby valving flow through the flow channels.

Application of a pressure to second control channel network 2118 causes the membrane of valve 2122 to deflect downward into underlying first branch 2106c only of first control channel network 2106. This fixes the valve 2112 in its deflected state, in turn allowing the pressure within the first control channel network 2106 to be varied without affecting the state of valve 2112.

Figure 22:
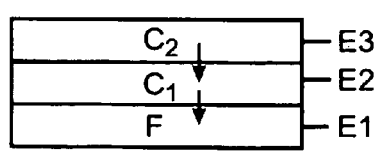
FIG. 22 shows a simplified cross-sectional view of the general microfluidic architecture of the device of FIGS. 21–21B.

The general architecture of the microfluidic device depicted in FIGS. 21–21B is summarized in the simplified cross-sectional view of FIG. 22. Specifically, elastomeric device 2200 comprises lowest elastomer layer E1 defining flow channel network F, underlying second elastomer layer E2 defining first control channel network C1. First control channel network C1 in turn underlies second control channel network C2 that is defined within third elastomer layer E3.

While the embodiment of the microfluidic device of FIGS. 21–21B is described as being fabricated from three separate elastomer layers, this is not required by the present invention. Large scale integrated microfluidic structures in accordance with embodiments of the present invention featuring multiplexed control lines may be fabricated utilizing only two elastomer layers. This approach is shown and illustrated in connection with FIGS. 23–23B.

Figure 23:
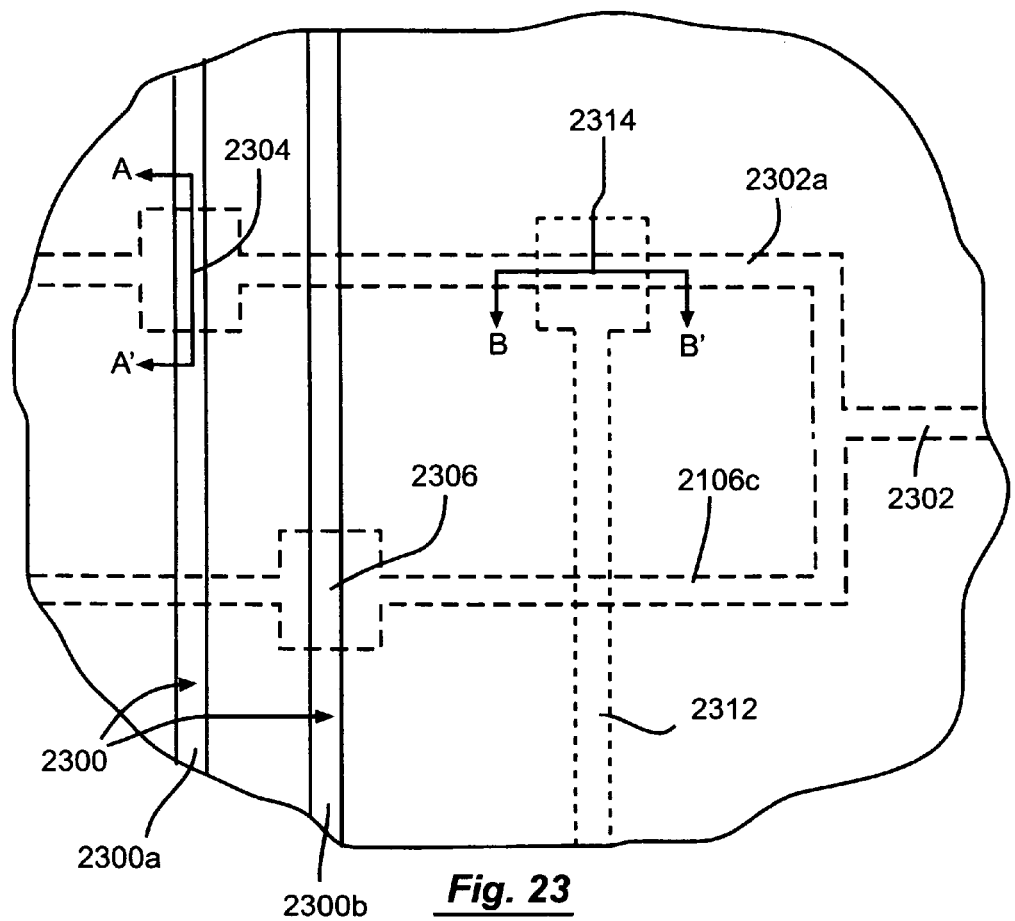
FIG. 23 shows a simplified plan view of an alternative embodiment of a microfluidic structure utilizing control channels to control other control channels.
Figure 23A:
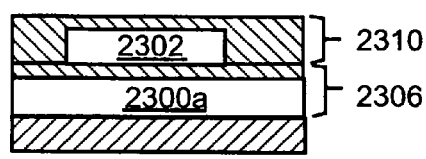
FIG. 23A shows a simplified cross-sectional view of the structure of FIG. 23 taken along the line 23A–23A'.

FIG. 23 shows a simplified plan view of a microfabricated elastomer device including first and second flow channels 2300a and 2300b, and first branched control channel network 2302 overlying flow channels 2300a and 2300b to define valves 2304 and 2306 respectively. FIG. 23A shows a cross-sectional view of the microfabricated elastomer device of FIG. 23, taken along line 23A–23A', with flow channel 2300a defined in lower elastomer layer 2306, and first control channel 2302 defined in upper elastomer layer 2310.

Figure 23B:
FIG. 23B shows a simplified cross-sectional view of the structure of FIG. 23 taken along the line 23B–23B'.

Lower elastomer layer 2308 further comprises a second control channel network 2312 running underneath first control channel 2302 to define valve 2314. Accordingly, FIG. 23B shows a cross-sectional view of the microfabricated elastomer device of FIG. 23, taken along line 23B–23B'. While present in the same (lower) elastomer layer 2308, flow channel network 2300 and second control channel network 2312 are separate and do not intersect one another.

Figure 24:
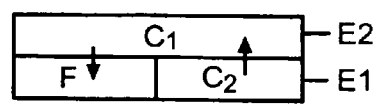
FIG. 24 shows a simplified cross-sectional view of the general microfluidic architecture of the device of FIGS. 23–23B.

As represented in the simplified cross-sectional view of FIG. 24, separate flow channel network F and control channel network C2 may thus be present on a single (lower) elastomer layer E1 that is overlaid by another elastomer layer E2 defining only a control channel network C1.

The microfluidic device illustrated in FIGS. 23–23B may be operated as follows. A fluid that is to be manipulated is present in flow channels 2300a and 2300b. Application of a pressure to the first control channel network 2302 causes the membranes of valves 2304 to deflect downward into their respective flow channels 2300a and 2300b, thereby valving flow through the flow channels.

Application of a pressure to second control channel network 2312 causes the membrane of valve 2314 to deflect upward into the overlying branch 2302a of first control channel network 2302. This fixes the valve 2314 in its deflected state, in turn allowing the pressure within the first control network 2302 to be varied without affecting the state of valve 2314.

In contrast with the embodiment shown in FIG. 21, the microfluidic device of FIGS. 23–23B features a valve that operates by deflecting upward into an adjacent control channel in response to an elevated pressure. Large scale integrated microfluidic structures incorporating such upwardly deflecting valves may include flow channels having rounded or arched cross-sections to facilitate valve closure, in a manner similar to that described above in connection with FIG. 11. Thus in a two-layer microfluidic structure comprising flow channels on both the upper and lower levels, both the upper and lower channels preferably exhibit an arched profile.

Figure 25:
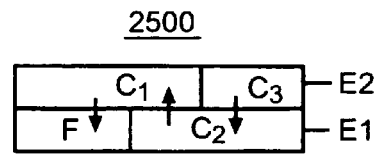
FIG. 25 shows a simplified cross-sectional view of the general microfluidic architecture of another embodiment of a device utilizing control over control lines by other control lines.

The approach of FIGS. 23–23B and 24 may be utilized to introduce almost unlimited control over complex flow functionality, without having to resort to more than two layers. This is illustrated in conjunction with FIG. 25, which represents a simplified cross-sectional view of a microfluidic structure 2500 comprising lower elastomer layer E1 having flow channel network F and second control channel network C2 defined therein, underlying upper elastomer layer E2 and having separate first and third control channel networks $C_1$ and $C_3$ defined therein.

A microfluidic device utilizing control channels to control other control channels as shown and described in connection with FIGS. 21–25 offers a number of advantages over conventional microfluidic devices employing a single control channel network. One potential advantage is enhanced functionality.

Specifically, the simple multiplexor structure of FIGS. 19A–B allows valving of all but one of n flow channels given only $x\log_x n$ control channels, thereby allowing flow through a single channel. However, the simple multiplexors of FIGS. 19A–B do not allow for the inverse functionality, wherein only one of the valves may be simultaneously actuated utilizing a multiplexor having the same number ($x\log_x n$) control lines.

Figure 26:
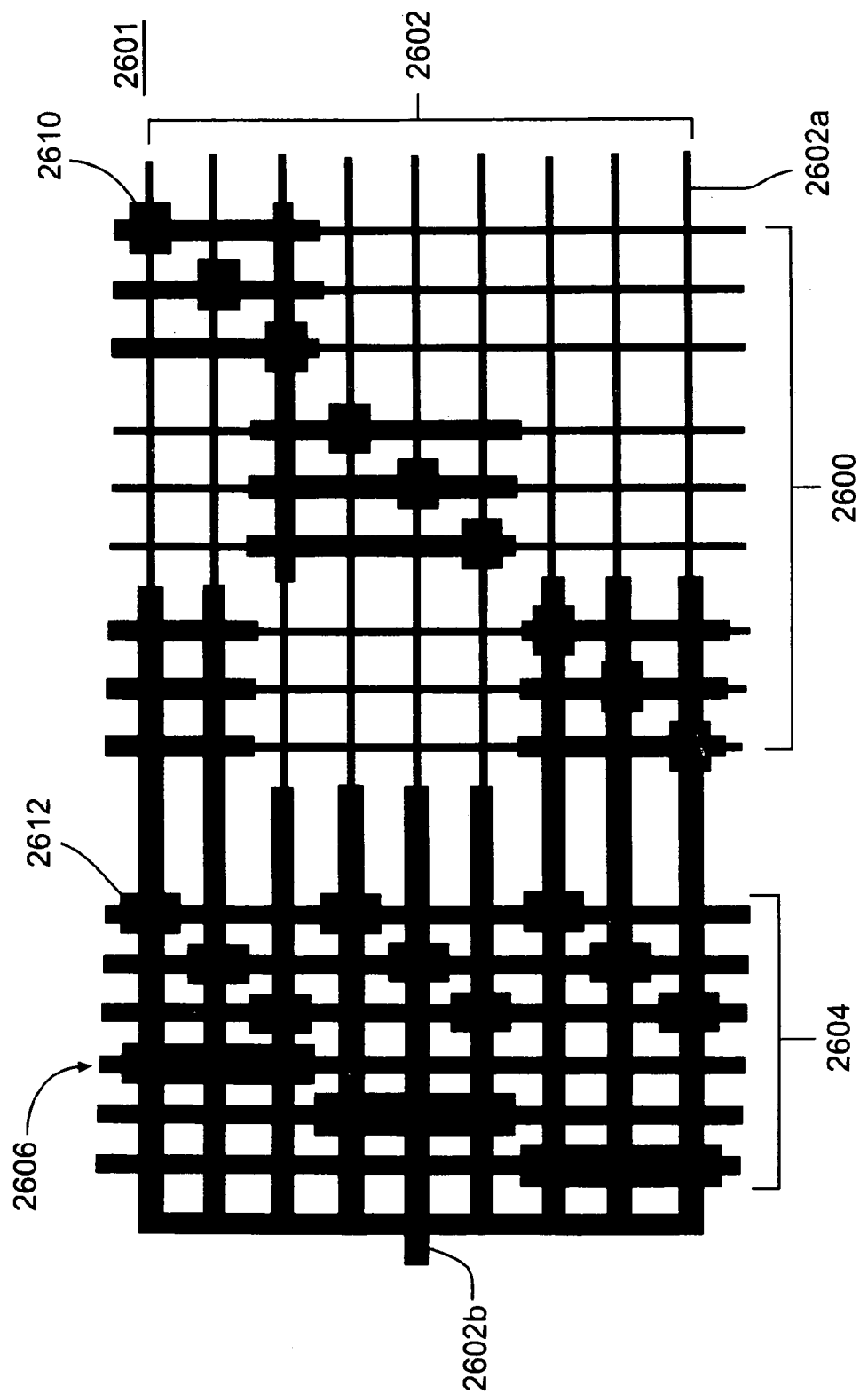
FIG. 26 shows a simplified plan view of one embodiment of an inverse multiplexor structure in accordance with the present invention.

Such functionality is, however, available through the use of control lines to control other control lines, as previously described. FIG. 26 illustrates one embodiment of an inverse multiplexor structure 2601 in accordance with an embodiment of the present invention, which utilizes multiple layers of control lines.

Parallel flow channels 2600 formed in a first elastomer layer are overlaid by a control channel network 2602 comprising a parallel set of control channels 2602a formed in a second elastomer layer and sharing a common inlet 2602b. There are the same number of control channels 2602a as flow channels 2600, with each control channel having a widened portion 2602b overlying one of the corresponding flow channels 2600 to define valve 2610.

At a point between common inlet 2602b and the first flow channel, a second network 2604 of control channels passes proximate to the first control channel network 2602, defining a multiplexor structure 2606 comprising valves 2612 in the form of a plurality of actuable membranes. In certain embodiments, this second network of control lines defining the multiplexor may be formed in a third elastomer layer overlying the second elastomer layer containing first control channel network. Alternatively, the second network of control lines defining the multiplexor may be formed in the first elastomer layer, alongside but not intersecting with, the flow channel network.

During operation of the inverse multiplexor structure shown in FIG. 26, common inlet 2602b of first control channel network 2602 is initially depressurized. Multiplexor 2604 is then actuated to select all but one of the channels of first control channel network 2602. Next, pressure is applied to inlet 2602b to cause a pressure increase in the sole unselected control channel of network 2602, thereby actuating the valve of only that unselected control channel. Inverse multiplexing functionality has thus been achieved.

Another potential advantage offered by the use of control lines to control other control lines is a reduction in the number of externally-accessible control lines required to control complex microfluidic structures. Specifically, the use of multiple layers of control lines can be combined with the multiplexor concept just described, to allow a few externally-accessible control lines to exert control over a large number of control channels responsible for operating large numbers of internal valve structures.

Figure 27:
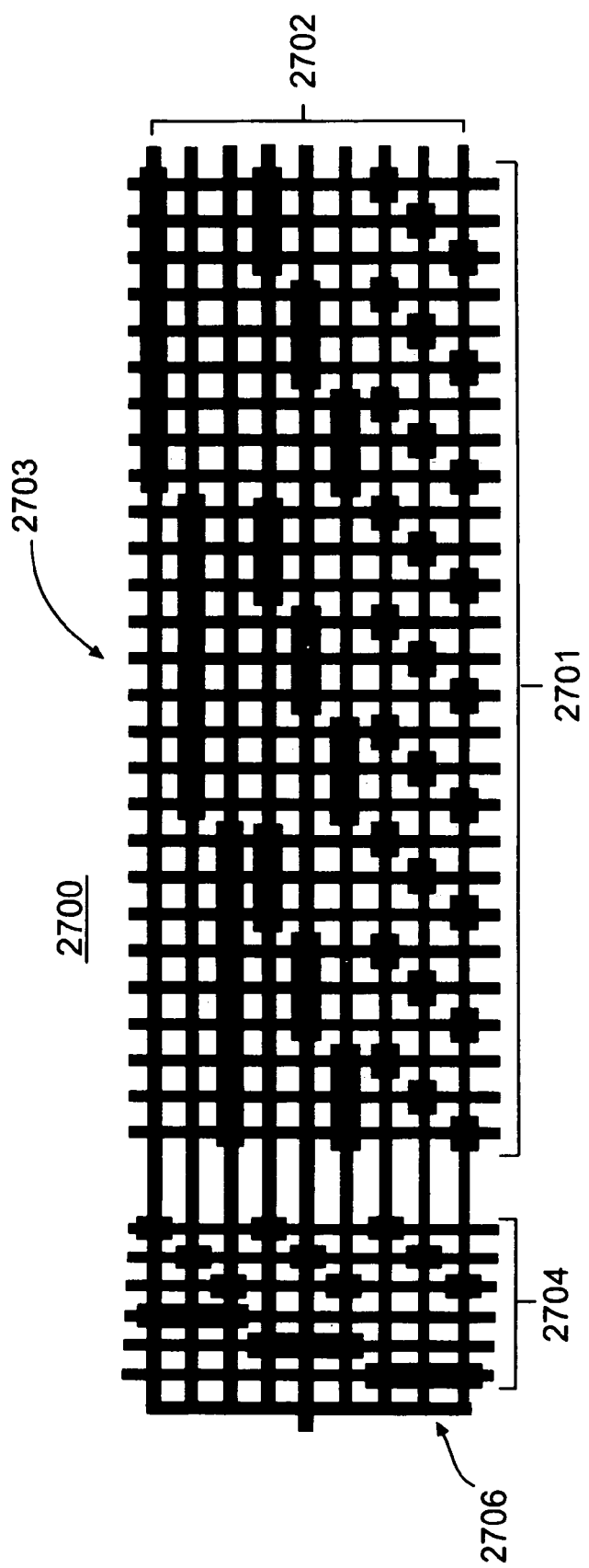
FIG. 27 shows a simplified plan view of one embodiment of a cascaded multiplexor structure in accordance with the present invention.

FIG. 27 shows a simplified plan view of one embodiment of microfluidic device 2700 in accordance with the present invention utilizing cascaded multiplexors. Specifically, parallel flow channels 2701 defined in one elastomeric layer are overlaid by first control channel network 2702 featuring wide and narrow control channel portions defining multiplexor 2703. First control channel network 2702 in turn either overlies or is underlaid by second flow channel network 2704, which also features wide and narrow control channel portions defining second multiplexor 2706.

FIG. 27 shows how a multiplexor comprising only six control lines may control a total of twenty-seven flow lines after cascading it with second multiplexor, requiring only a single input, resulting in a total of only seven control lines. The logical states of the second multiplexor may be set sequentially by addressing each line using the first multiplexor, and then setting the state using the additional input. High pressure (on) states may generally be retained for a limited amount of time, due to the intrinsic gas permeability of PDMS, as over time pressure within the second multiplexor is reduced via evaporation or outgussing of actuation fluid. This loss in pressure can be counteracted two ways, either by periodically refreshing the state of the second multiplexor, or by reducing the rate of loss in actuation fluid to negligible levels relative to the total time of the experiment.

As just described, combinatorial arrays of binary or other valve patterns can increase the processing power of a network by allowing complex fluid manipulations with a minimal number of controlled inputs. Such multiplexed control lines can be used to fabricate silicone devices with thousands of valves and hundreds of individually addressable reaction chambers, with a substantial reduction in the number of control inputs required to address individual valve structures.

3. Microfluidic Memory Array Structure

Microfluidic techniques in accordance with embodiments of the present invention may be utilized to fabricate a chip that contains a high density array of 1000 individually addressable picoliter scale chambers and which may serve as a microfluidic memory storage device. Using two multiplexors as fluidic design elements, a microfluidic memory storage device was designed with 1000 independent compartments and 3574 microvalves, organized as an addressable 25×40 chamber microarray.

Figure 29A:
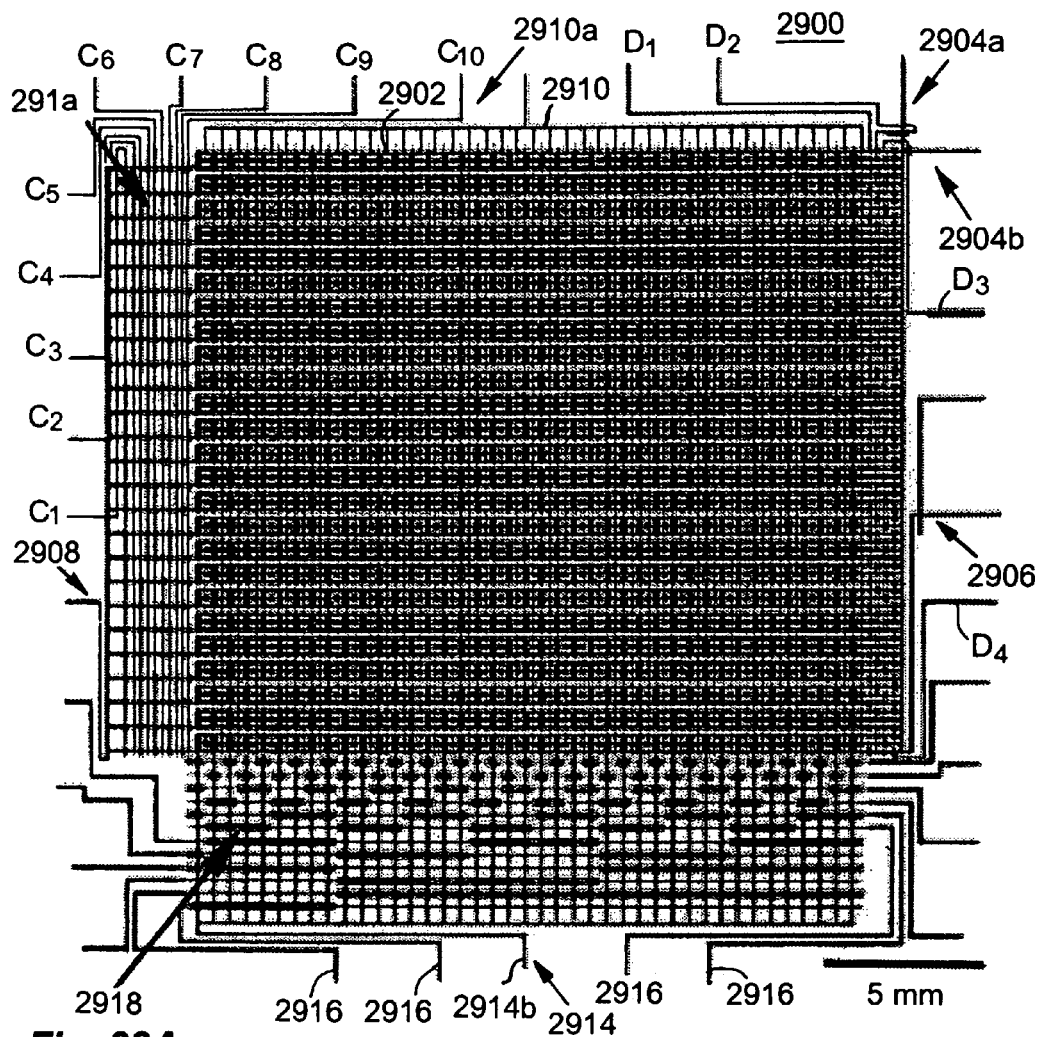
FIG. 29A shows an optical micrograph of a microfluidic memory storage device.
Figure 29B:
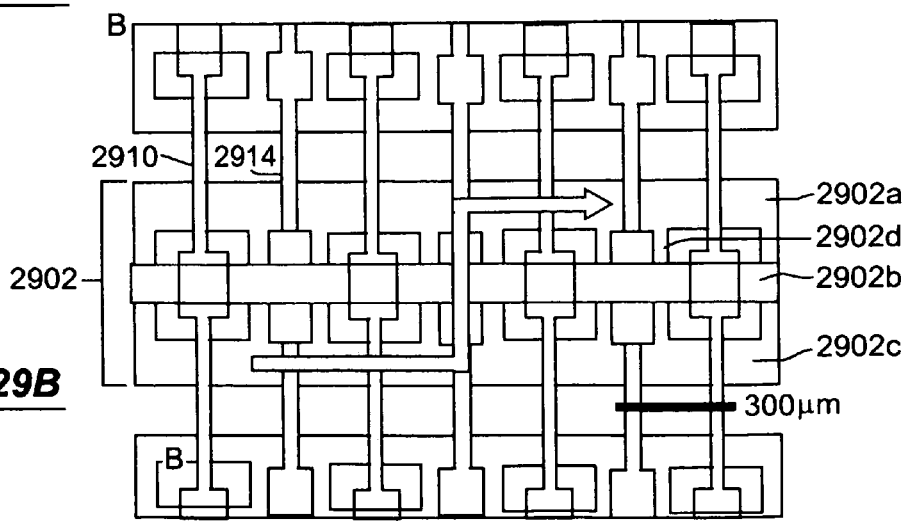
FIG. 29B is a simplified and enlarged plan view showing purging mechanics for a single chamber within a selected row of the chip shown in FIG. 29A.

FIG. 29A is a simplified plan view showing a mask design for the microfluidic memory storage device. FIG. 29B shows a simplified enlarged view of one storage location of the array of FIG. 29A, illustrating purging machanics.

Array 2900 comprises a first elastomer layer defining rows 2902 of parallel triplet flow channels 2902a–c having interconnecting vertical branch flow channels 2902d. For the purposes of this application, flow channels 2902a and 2902c flanking central flow channel 2902b in each row are referred to as "bus lines". Each intersection between a vertical branch 2902d and a central flow channel 2902b defines a separate storage location in that row and for the storage device. Each of the flow channels shares a common sample input 2904a or 2904b, and a common sample output 2906. Each of the row flow channels 2902a–c shares a common purge input 2908.

Overlying the first elastomer layer containing flow channels is a second elastomer layer containing networks of control channels. Horizontal compartmentalization control channel network 2910 having common inlet 2910a is formed in second elastomer layer. Control lines C1–C10 defining row multiplexor 2912 are also formed in the second elastomer layer.

Row access control lines D1–D4 are also formed in the second elastomer layer. Row access control lines D1–D4 are selectively actuable to control the flow of fluid through the central flow channel or one of the flanking bus lines for any one of the rows of the array.

The second elastomer layer also defines vertical compartmentalization control channel network 2914 having common inlet 2914b. At a point between common inlet 2914b and the first row of the array 2900, a separate control channel network 2916 formed in the first elastomer layer crosses under the vertical compartmentalization control channel network 2914 to define column multiplexor 2918. The embodiment of FIG. 29 thus represents a two-layer device allowing control over vertical compartmentalization control channels utilizing two separate control channel networks multiplexor structures 2914 and 2916. Specifically, during operation of the storage device, actuation of select control channels of the column multiplexor allows access to only one particular storage location in the array while all other storage locations remain sealed and uncontaminated. Operation of the storage device 2900 is now described in detail.

Figure 29C:
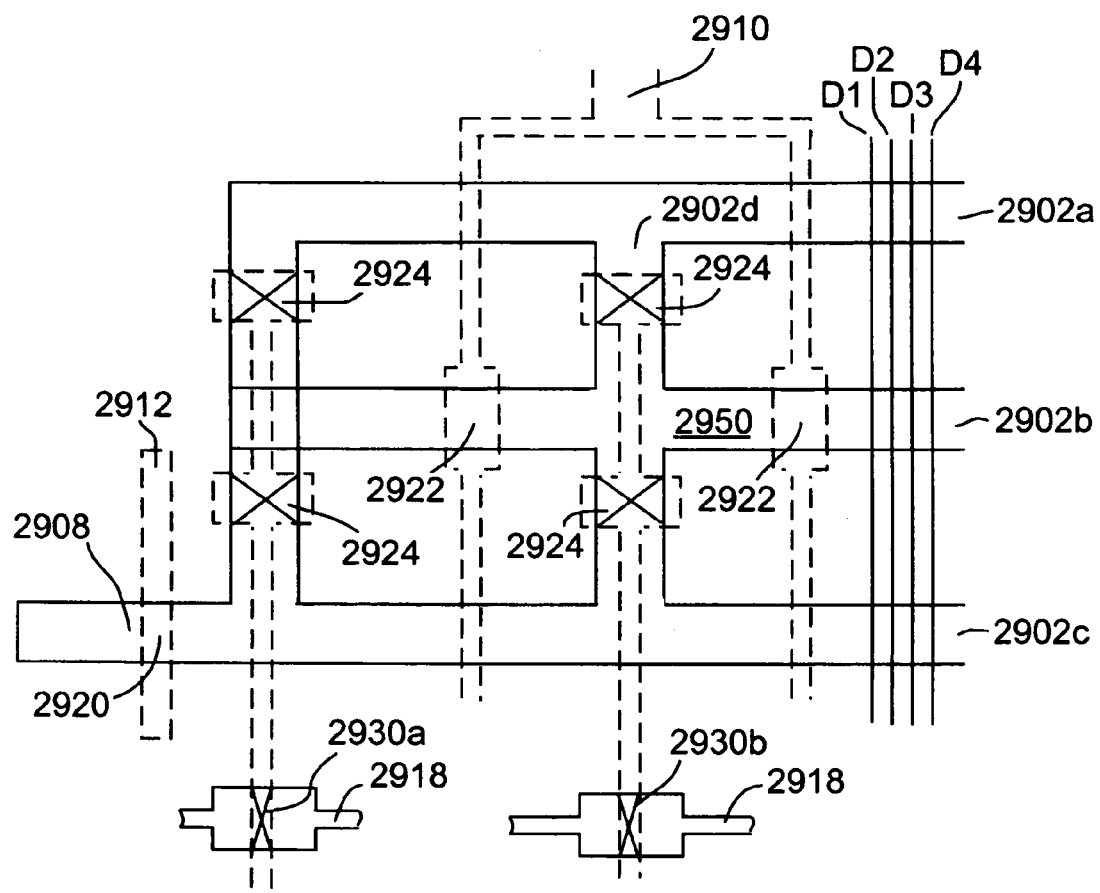
FIGS. 29C–F are simplified enlarged views of the array of FIG. 29A showing loading and purging of an individual storage location.

FIGS. 29C–F show enlarged plan views of one storage location of the array. As shown in FIG. 29C, at an initial time vertical compartmentalization control channel 2914 is pressurized to close vertical compartmentalization valves 2924. Column multiplexor 2918 is then pressurized to activate valves 2930a–b to seal the vertical compartmentalization valves 2924 in their pressurized state.

Figure 29D:
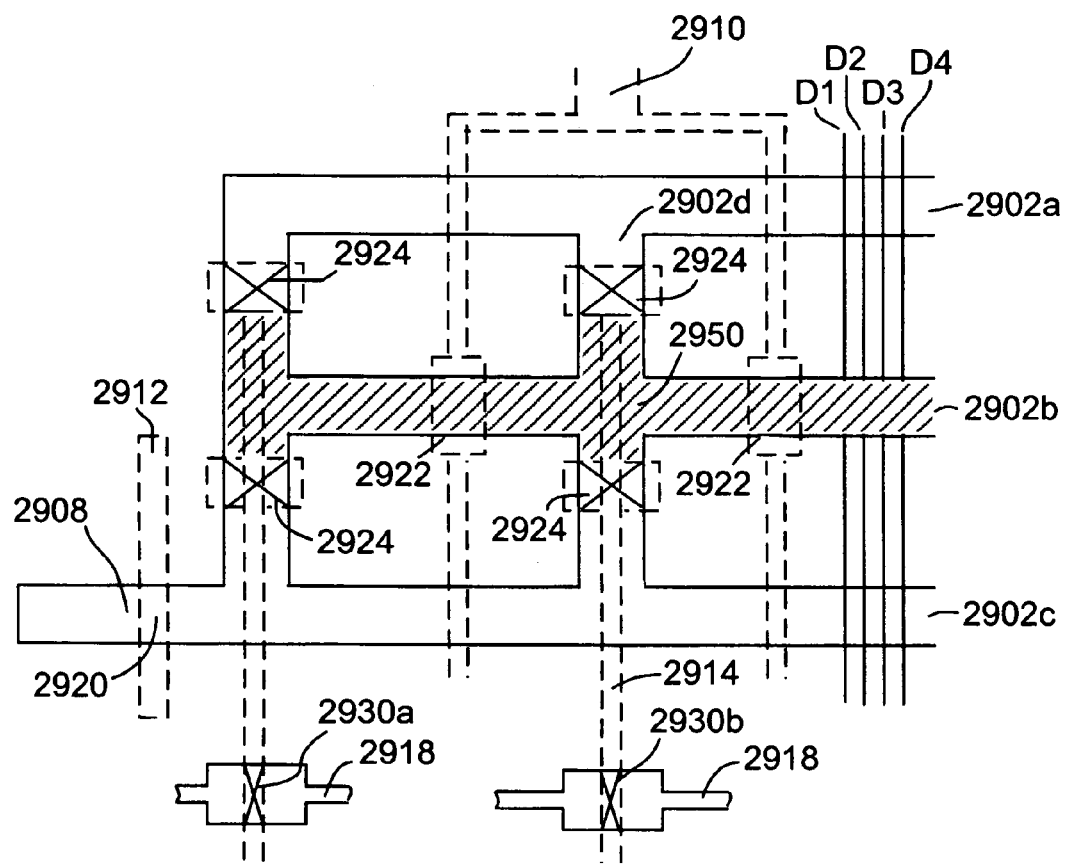
Figure 29E:
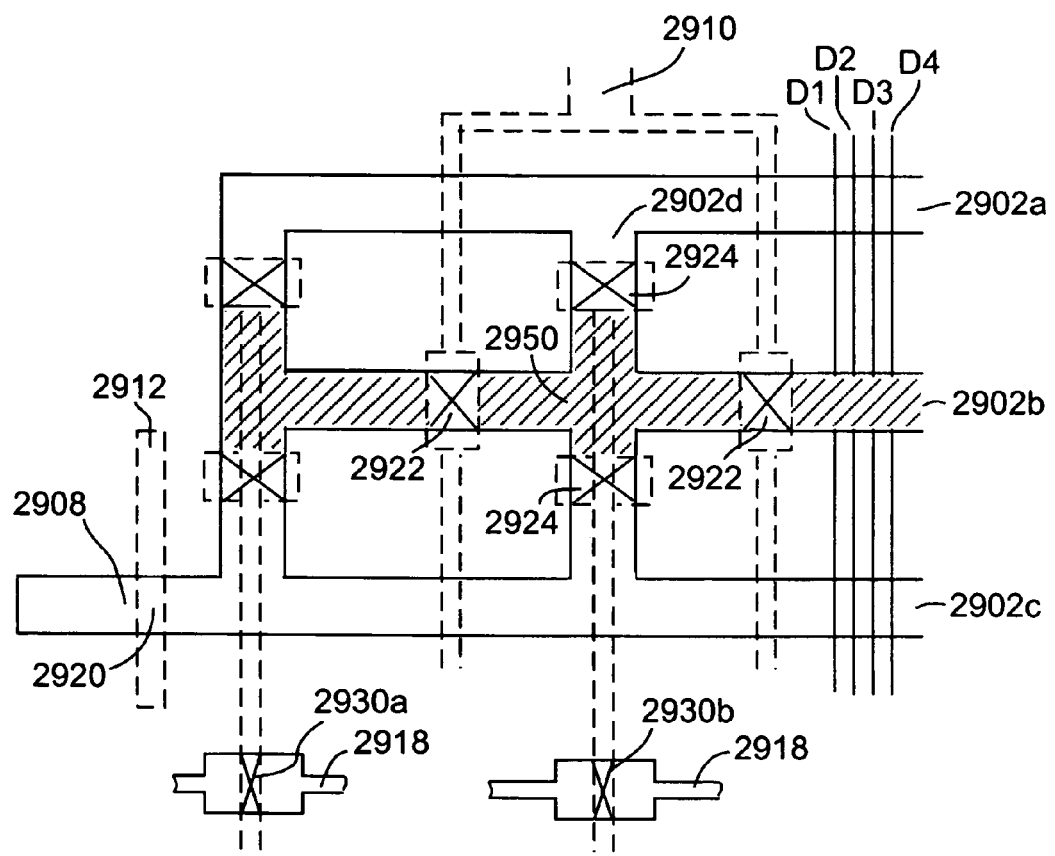

FIG. 29D shows the loading of all storage locations located along a particular central flow line with fluid, by selective manipulation of control lines D1–4. The closed state of vertical compartmentalization valves 2924 limits the vertical movement of the loaded fluid. FIG. 29E shows pressurization of horizontal compartmentalization control channel 2910 to close horizontal compartmentalization valves 2922, thereby isolating adjacent storage locations.

Figure 29F:
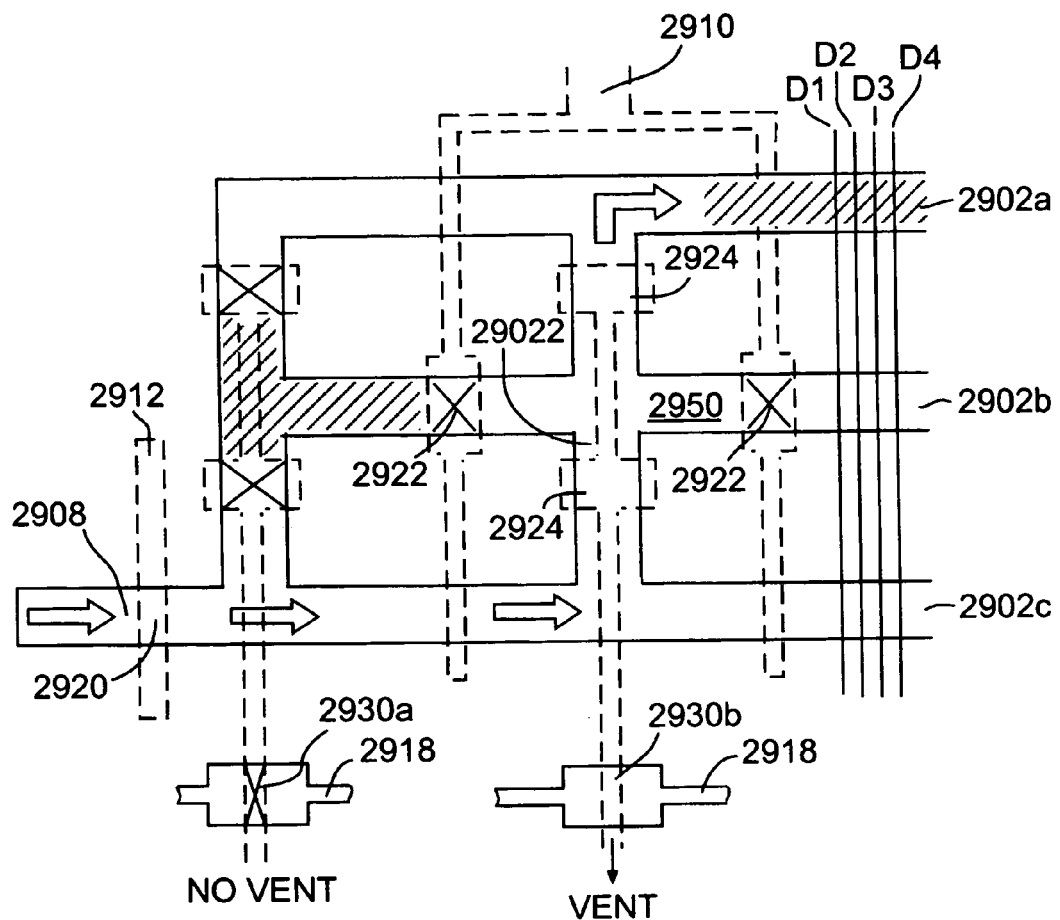

FIG. 29F shows the purging of loaded fluid from specific storage locations. Specifically, column multiplexor 2918 is depressurized to deactuate valve 2930b, allowing venting of control channel and deactuation of the vertical compartmentalization valves 2924 lying above and below storage location 2950. Column multiplexor 2918 remains pressurized to keep valve 2930a actuated, thereby maintaining in a closed state vertical compartmentalization valves 2924 of adjacent storage locations.

Finally, contol lines D1–4 are manipulated to allow flow through only the top bus line 2902a. Pressure is applied to purge inlet 2908, forcing the contents of storage location 2950 into top bus line 2902a, along the bus line 2902a, and ultimately out of output 2906.

Summarizing, the storage array chip contains an array of 25×40 chambers, each of which has volume ~250 pL. Each chamber can be individually addressed using the column multiplexor and row multiplexor. The contents of each memory/storage location can be selectively programmed to be either dye (sample input) or water (wash buffer input).

The large scale integrate multiplexor valve systems in accordance with embodiments of the present invention allow each chamber of the matrix to be individually addressed and isolated, and reduces the number of outside control interconnects to twenty-two. Fluid can be loaded into the device through a single input port, after which control layer valves then act as gates to compartmentalize the array into 250 pL chambers. Individual chamber addressing is accomplished through flow channels that run parallel to the sample chambers and use pressurized liquid under the control of the row and column multiplexors and to flush the chamber contents to the output.

FIG. 29B is a simplified and enlarged plan view again showing purging mechanics for a single chamber within a selected row of the chip shown in FIG. 29A. Each row contains three parallel microchannels. To purge a specific chamber pressurized fluid is first introduced in the purge buffer input. The row multiplexor then directs the fluid to the lower most channel of the selected row. The column multiplexor releases the vertical valves of the chamber, allowing the pressurized fluid to flow through the chamber and purge its contents.

This device adds a significant level of complexity to previous microfluidic plumbing in that there are two successive levels of control—the column multiplexor actuates valve control lines, which in turn actuate the valves themselves. The design and mechanics of the microfluidic array are similar to random access memory (RAM). Each set of multiplexors is analogous to a memory address register, mapping to a specific row or column in the matrix.

Like dynamic RAM, the row and column multiplexors have unique functions. The row multiplexor is used for fluid trafficking: it directs the fluid responsible for purging individual compartments within a row and refreshes the central compartments (memory elements) within a row, analogous to a RAM word line. The column multiplexor acts in a fundamentally different manner, controlling the vertical input/output valves for specific central compartments in each row.

To operate the column multiplexor, the vertical containment valve on the control layer is pressurized to close off the entire array. The column multiplexor, located on the flow layer, is activated with its valves deflected upwards into the control layer to trap the pressurized liquid in the entire vertical containment valve array. A single column is then selected by the multiplexor, and the pressure on the vertical containment valve is released to open the specified column, allowing it to be rapidly purged by pressurized liquid in a selected row.

Figure 29G:
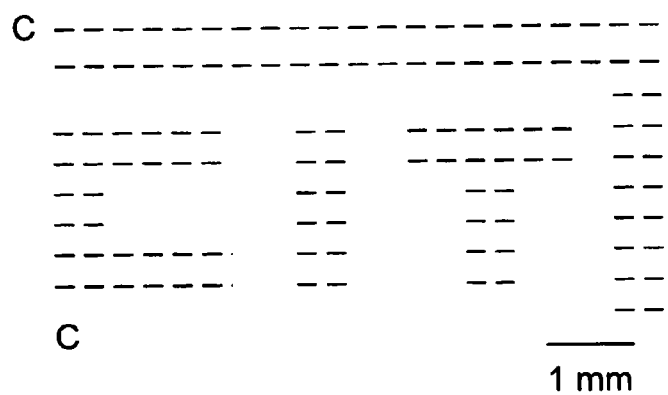
FIG. 29G shows a demonstration of microfluidic memory display.

To demonstrate the functionality of the microfluidic memory storage device, the central memory storage chambers of each row were loaded with dye (2.4 mM bromophenol blue in sodium citrate buffer, pH 7.2) and proceeded to purge individual chambers with water to spell out "CIT". Since the readout is optical, this memory device also essentially functions as a fluidic display monitor. FIG. 29G shows a demonstration of microfluidic memory display. Individual chambers are selectively purged to spell out "CIT". A key advantage of the plumbing display is that once the picture is set, the device consumes very little power.

4. One Way Valve/Fluidic Display

The storage device depicted in FIG. 29A comprises an array of chambers whose contents are individually accessible through horizontal movement of fluid through co-planar bus lines positioned on either side of a central flow channel. However, techniques for fabricating large scale integrated microfluidic structures in accordance with embodiments of the present invention are not limited to fabricating this particular device.

Figure 34A:
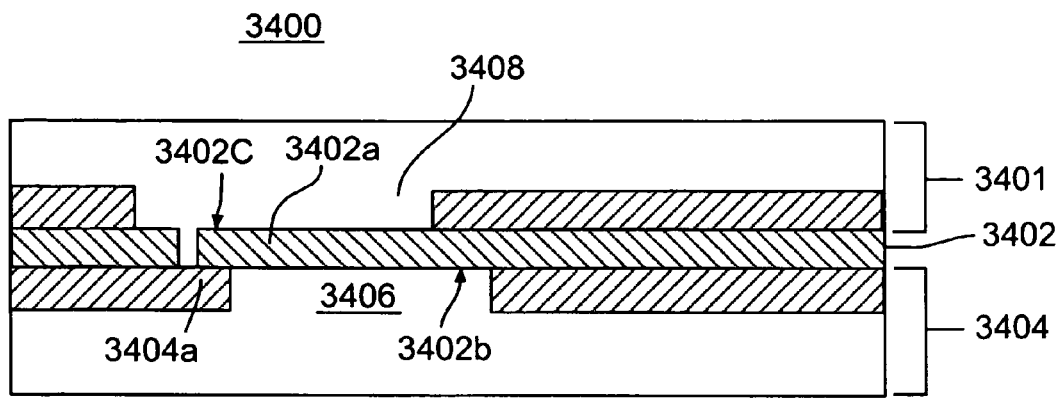
FIGS. 34A–C show simplified cross-sectional views illustrating structure and operation of an embodiment of a vertical one-way valve in accordance with an embodiment of the present invention.
Figure 34B:
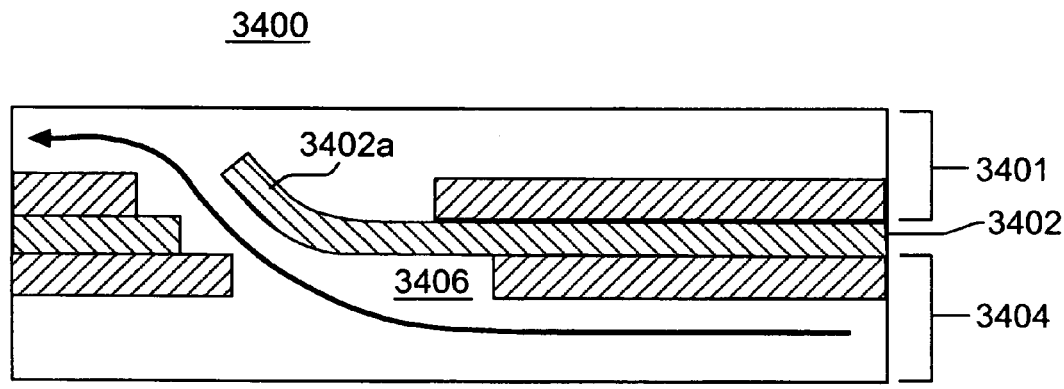
Figure 34C:
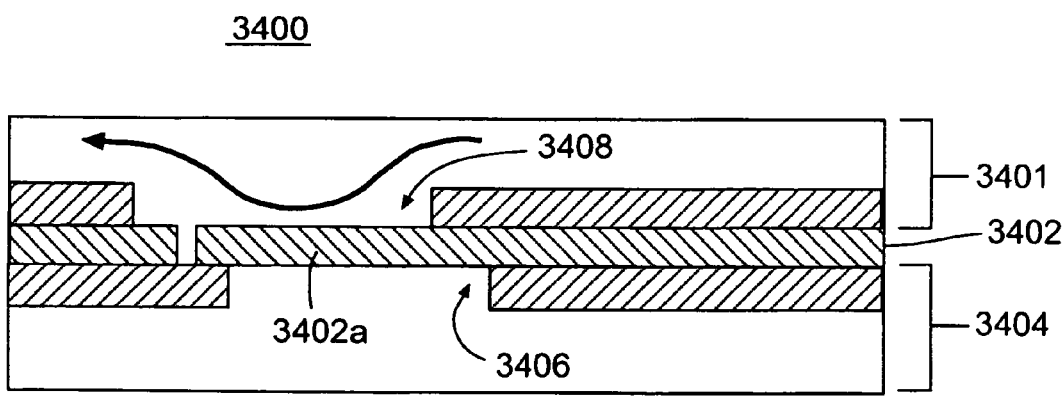

FIGS. 34A–C show simplified cross-sectional views illustrating the structure and operation of an embodiment of a valve structure in accordance with the present invention, which allows for the vertical flow of fluid in one direction only. As described in detail below, these one-way valves may in turn be utilized to create an alternative embodiment of a large-scale integrated microfluidic storage device utilizing movement of fluid in the vertical, as well as horizonatal directions.

As shown in FIG. 34A, one way valve 3400 is formed from upper elastomer layer 3401 overlying middle elastomer layer 3402 that in turn overlies lower elastomer layer 3404. Lower elastomer layer 3404 defines first via opening 3406. Middle elastomer layer 3402 comprises a flexible membrane portion 3402a integral on only side 3402b with the surrounding elastomer material of middle layer 3402. Membrane portion 3402a of middle elastomer layer 3402 overlies the entirety of first via opening 3406, with edge 3402c of membrane portion 3402 resting on seat portion 3404a of lower elastomer layer 3404. Upper elastomer layer 3401 defines second via opening 3408 horizontally offset from the location of first via opening 3406.

As shown in FIG. 34B, fluid may freely flow through one-way valve 3400 in the upward direction. Specifically, a pressurized fluid will move through first via opening 3406 and unseat flexible membrane portion 3402a, deflecting it into the overlying second via opening 3408 and allowing pressurized fluid to enter second via opening 3408 and upper elastomer layer 3401.

By contrast, as shown in FIG. 34C, fluid may not flow through one-way valve 3400 in the downward direction. Specifically, a pressurized fluid attempting to move through second via opening 3408 will encounter seated membrane portion 3402a. Membrane portion 3402a will remain seated, and valve 3400 closed, until such time as the pressure of fluid in the underlying first via opening 3406 exceeds the pressure in second via opening 3408.

While the specific embodiment of a one-way valve shown in FIGS. 34A–C is fabricated utilizing three distinct elastomer layers, this is not required. It may be possible to fabricate this structure from only two elastomer layers, forming the membrane portion and the top layer utilizing a single mold.

And while the specific embodiment of a one-way valve shown in FIGS. 34A–C allow passage of fluid in the upward direction, alternative embodiments may allow passage of fluid in the downward direction only. Such a valve structure may be fabricated by reversing the orientation of the one-way valves.

One-way valves in accordance with embodiments of the present invention may be utilized to fabricate display devices. FIGS. 35A–D are simplified cross-sectional views illustrating one embodiment of such a pixel structure.

Figure 35A:
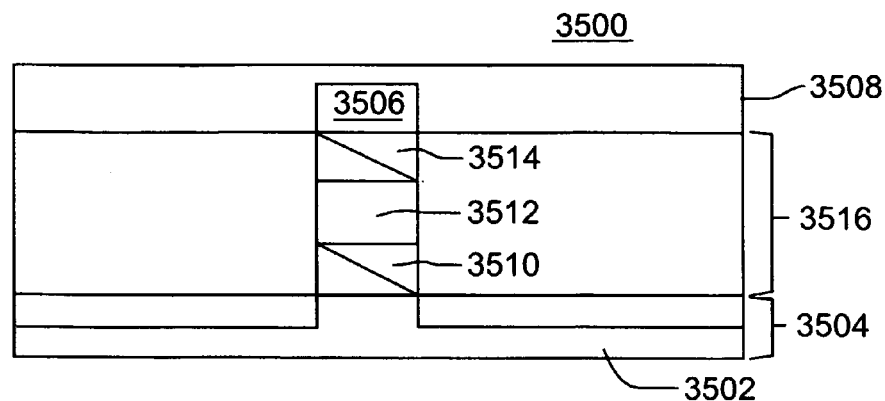
FIGS. 35A–D show simplified cross-sectional views illustrating structure and operation of one pixel of a microfluidic display device in accordance with the present invention.

As shown in FIG. 35A, pixel 3500 comprises first flow channel 3502 formed in lowermost elastomer layer 3504. Second flow channel 3506, orthogonal to first flow channel 3502, is formed in uppermost elastomer layer 3508. First one-way valve 3510, chamber 3512, and second one way valve 3514, are formed in elastomer layers 3516 intervening between layers 3504 and 3508.

Figure 35B:
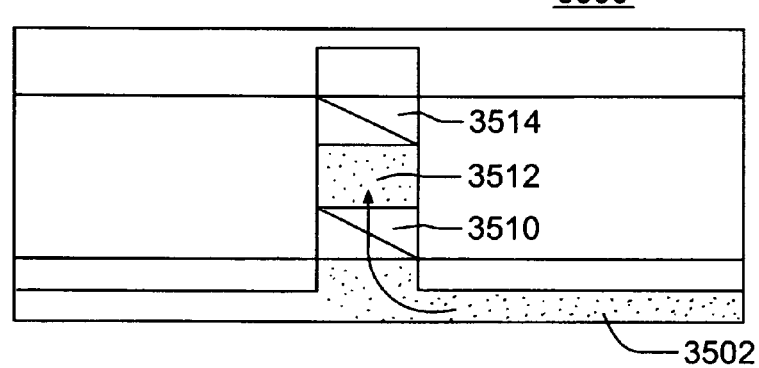
Figure 35C:
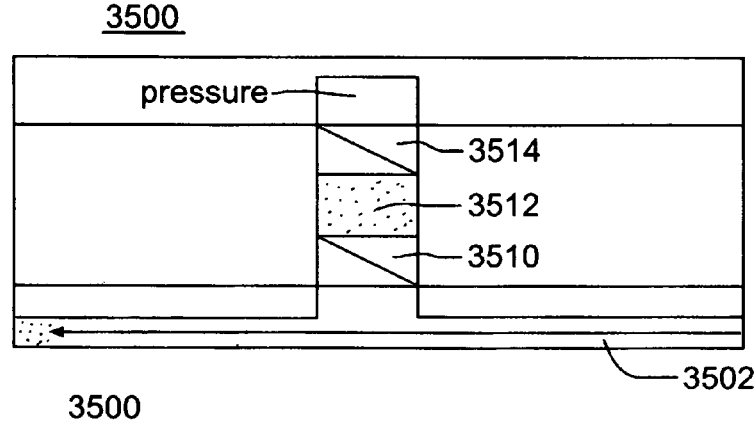
Figure 35D:
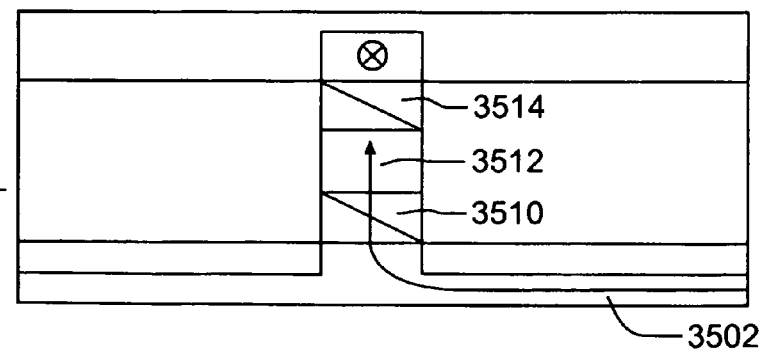

Operation of display pixel 3500 is summarized in FIGS. 35B–D. In FIG. 35B, colored fluid 3518 from first flow channel 3502 is introduced under pressure through first one-way valve 3510 into chamber 3512. Pixel 3500 has now been charged with a colored dye.

This pixel charging may be performed nonselectively by applying a higher pressure to first flow channel 3502 than is present in any of the second flow channels. Alternatively, this pixel charging may be performed selectively by also utilizing a multiplexor in communication with the second flow channels, to create the necessary pressure differential between the first and only select second flow channels.

In FIG. 35C, the colored fluid is purged from first flow channel 3502 while maintaining second flow channel 3506 at a higher pressure, thereby maintaining first one-way valve 3510 closed.

As shown in FIG. 35D, the color of pixel 3500 may be changed by lessening the pressure in second flow channel 3506 and flowing a colorless fluid through first flow channel 3502, first one-way valve 3510, chamber 3512, second one-way valve 3514, and ultimately second flow channel 3506.

Figure 36:
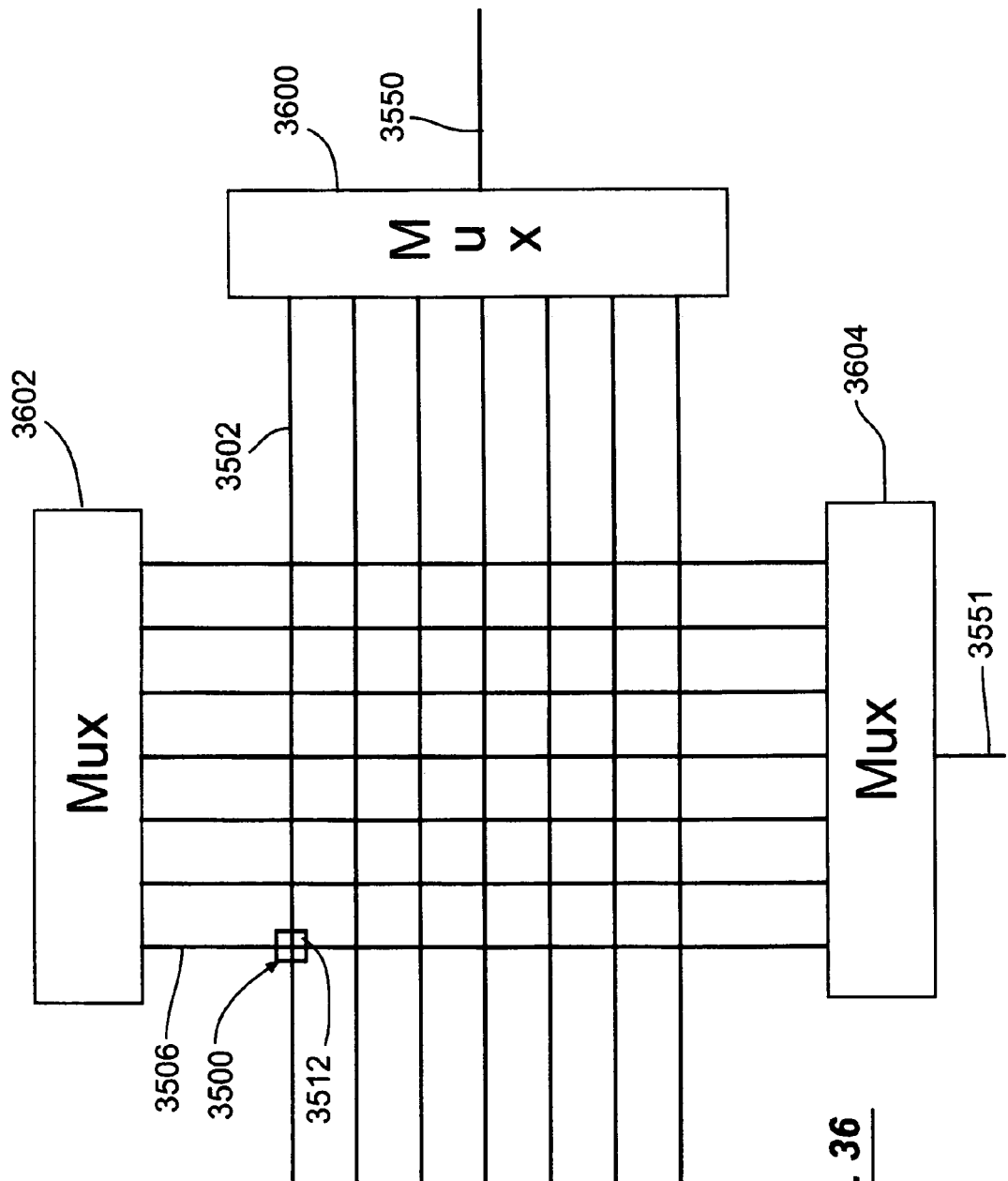
FIG. 36 shows a plan view of one embodiment of a display simplified cross-sectional views illustrating structure and operation of one pixel of a display device in accordance with the present invention.

FIG. 36 shows a plan view of a display device comprising an entire array of pixels as described in FIGS. 35A–D. Specifically, flow of fluid from inlet 3550 through parallel lowermost flow channels 3502 is governed by first multiplexor 3600. The pressure and flow of fluid from inlet 3551 through parallel uppermost flow channels 3506 in the parallel uppermost flow channel is governed by second and third multiplexors 3602 and 3604.

5. Large Scale Integrated Comparator Structure

While the memory array structure previously described above represents an important advance over existing microfluidic structures, it does not allow for two different materials to be separately introduced and then mixed in a particular chamber. This functionality, however, is provided in a second chip microfabricated with large scale integration technology which is analogous to an array of 256 comparators. Specifically, a second device containing 2056 microvalves was designed which is capable of performing more complex fluidic manipulations.

Figure 30A:
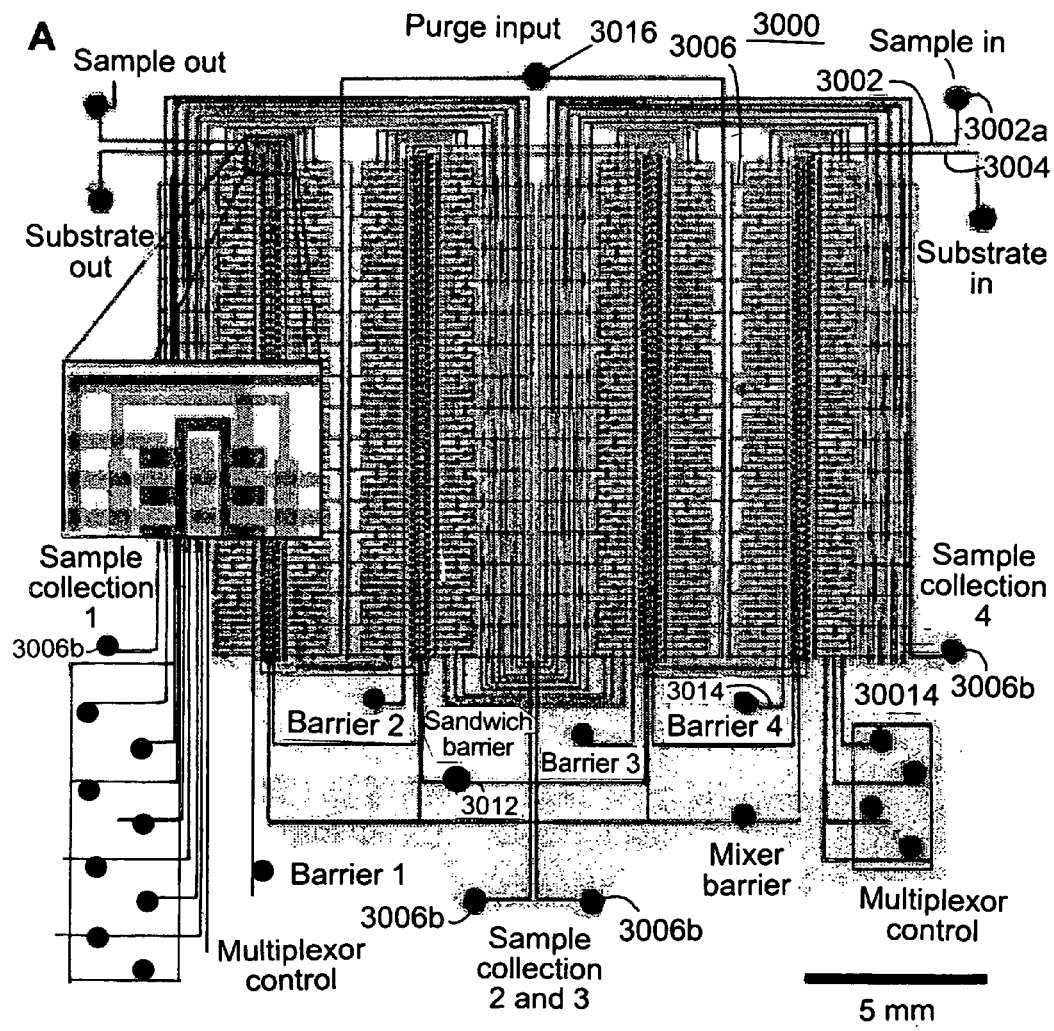
FIG. 30A shows an optical micrograph of a microfluidic comparator chip.
Figure 30B:
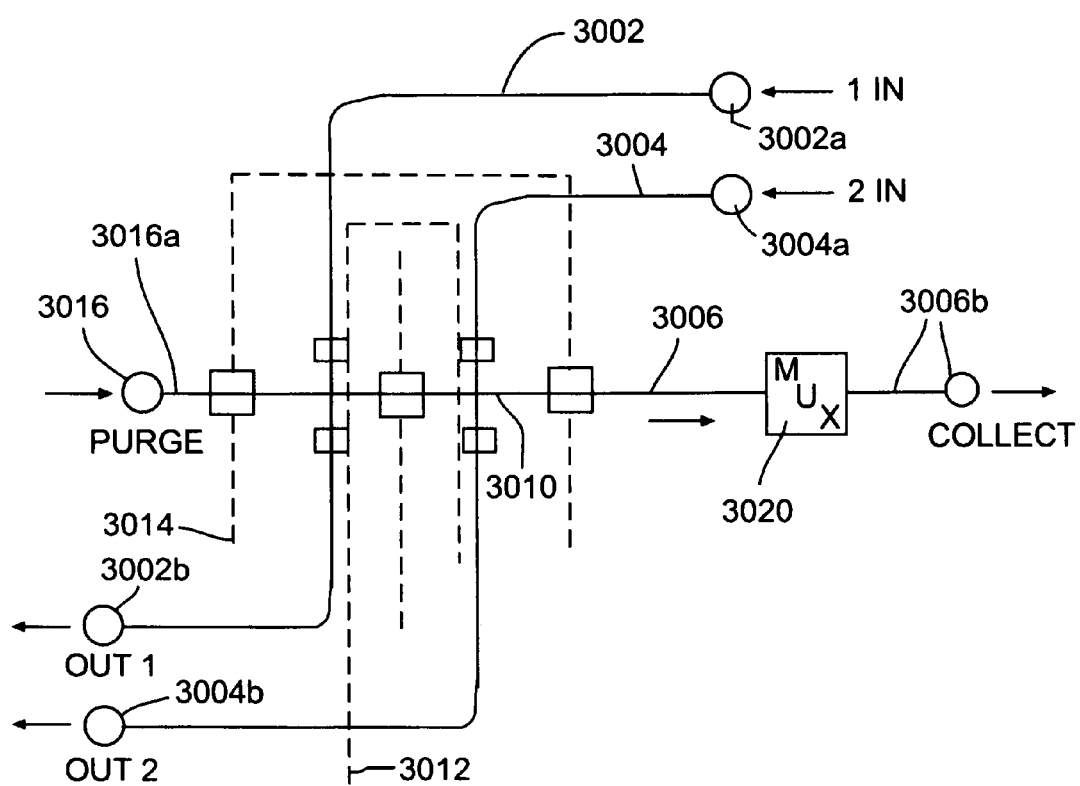
FIG. 30B is a simplified schematic view of the microfluidic comparator chip of FIG. 30A.

FIG. 30A shows an optical micrograph of a microfluidic comparator chip 3000. The various inputs have been loaded with colored food dyes to visualize the channels and sub-elements of the fluidic logic. FIG. 30B shows a simplified schematic plan view of one portion of the chip of FIG. 30A.

Comparator chip 3000 is formed from a pair of parallel, serpentine flow channels 3002 and 3004 having inlets 3002a and 3004a respectively, and having outlets 3002b and 3004b respectively, that are intersected at various points by branched horizontal rows of flow channels 3006. Portions of the horizontal flow channels located between the serpentine flow channels define mixing locations 3010.

A first barrier control line 3012 overlying the center of the connecting channels is actuable to create adjacent chambers, and is deactivable to allow the contents of the adjacent chambers to mix. A second barrier control line 3014 doubles back over either end of the adjacent chambers to isolate them from the rest of the horizontal flow channels.

One end 3006a of the connecting horizontal flow channel 3006 is in fluid communication with pressure source 3016, and the other end 3006b of the connecting horizontal flow channel 3006 is in fluid communication with a sample collection output 3018 through multiplexor 3020.

Figure 30C:
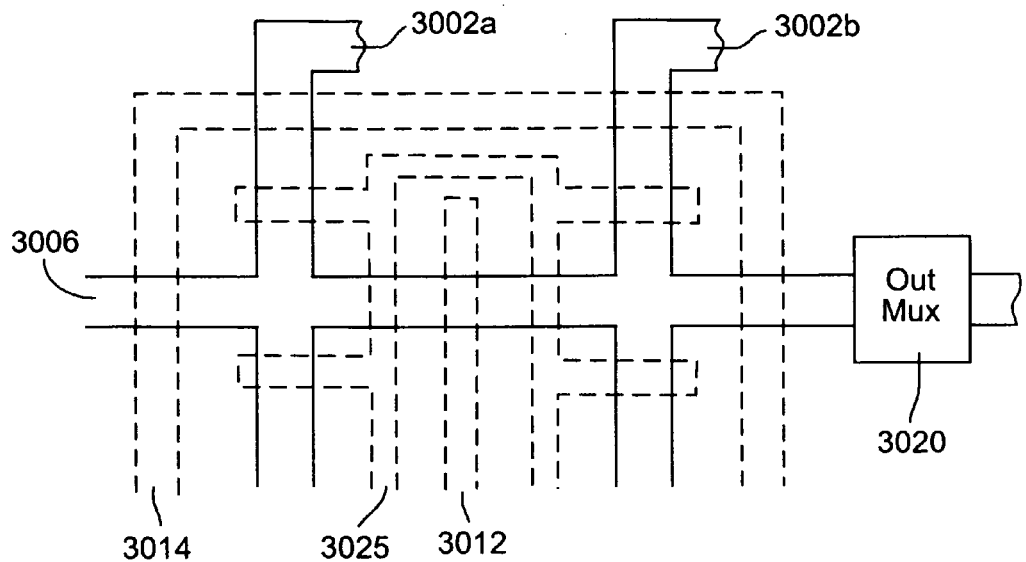
FIGS. 30C–H are enlarged simplified plan views showing loading of the chamber of the microfluidic structure of FIG. 30A.
Figure 30D:
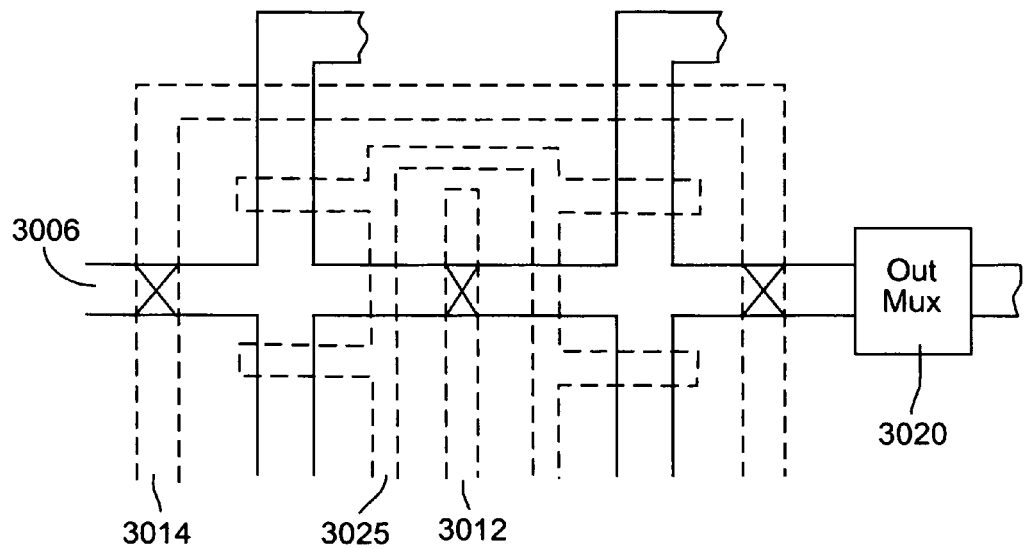
Figure 30E:
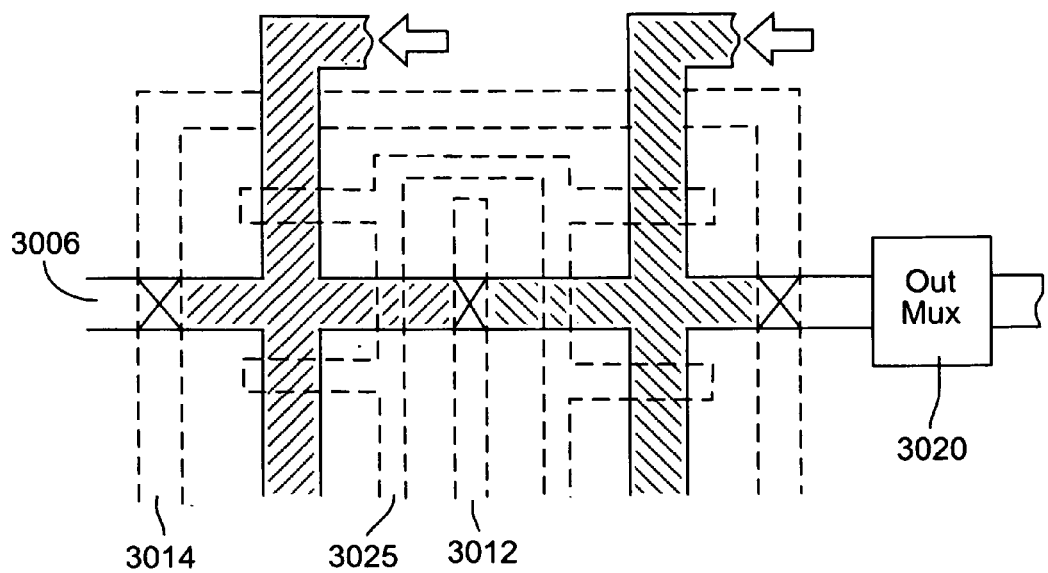
Figure 30F:
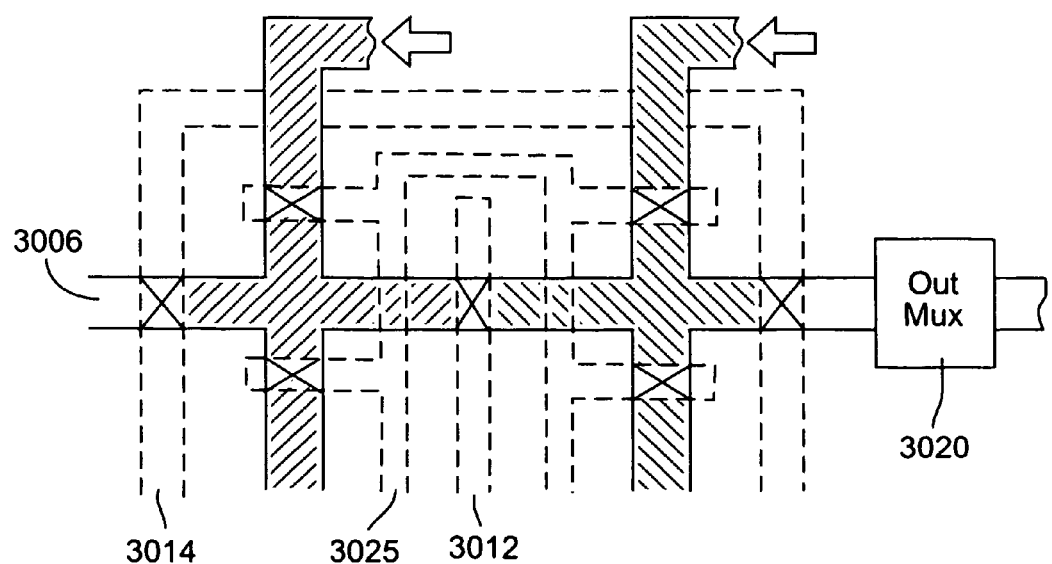

FIGS. 30C–H show simplified enlarged plan views of operation of one mixing element of the structure of FIGS. 30A–B. FIG. 30C shows the mixing element prior to loading, with the mixer barrier control line and wrap-around barrier control line unpressurized. FIG. 30D shows pressurization of the wrap-around barrier control line and barrier mixer line to activate isolation valves and separation valve to define adjacent chambers 3050 and 3052. FIG. 30E shows loading of the chambers with a first component and a second component by flowing these materials down the respective flow channels. FIG. 30F shows pressurization of the vertical compartmentalization control line 3025 and the isolation to define the adjacent chambers.

Figure 30G:
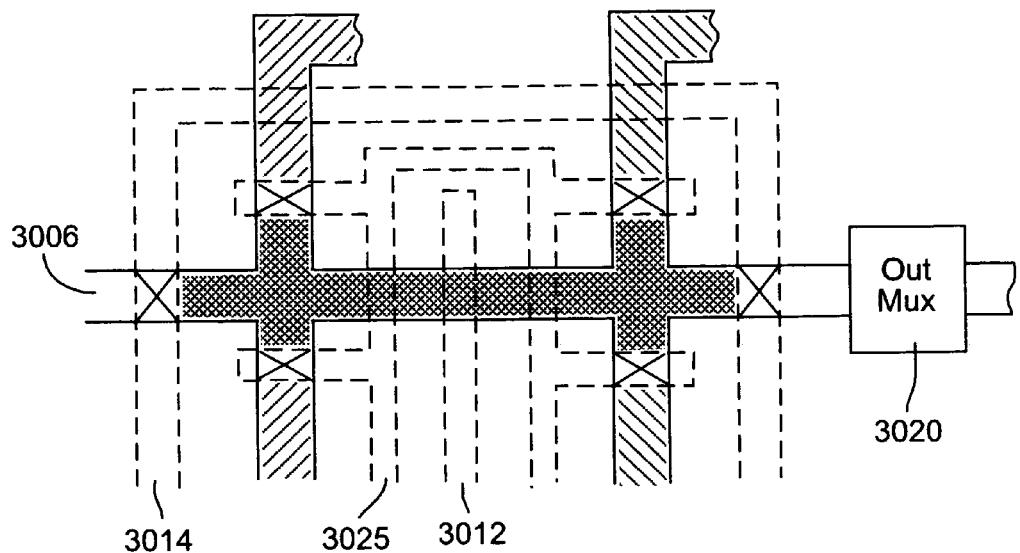

FIG. 30G shows depressurization of the mixing barrier control channel to deactivate the separation barrier valve, thereby allowing the different components present in the adjacent chambers to mix freely.

Figure 30H:
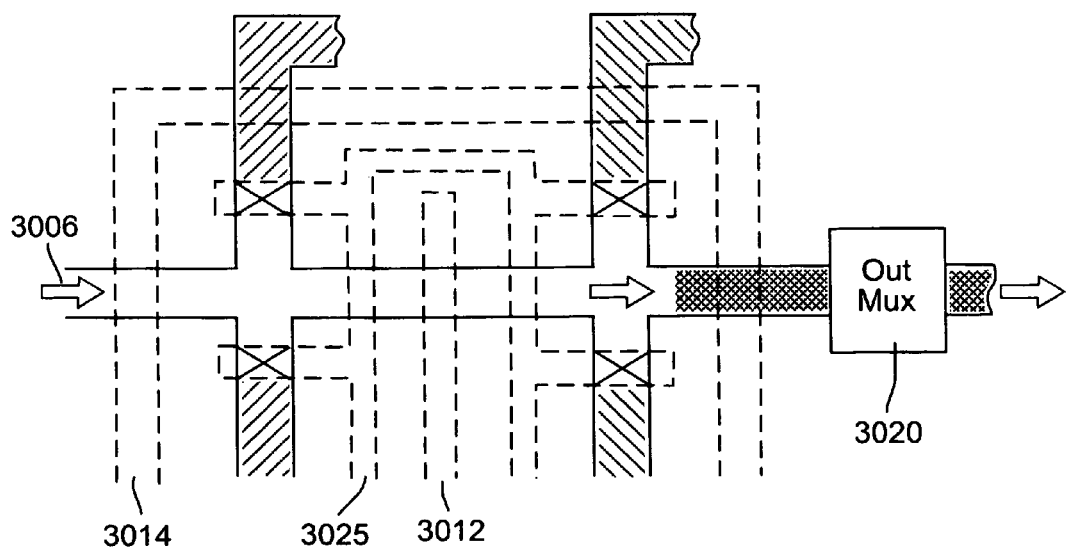
Figure 31A:
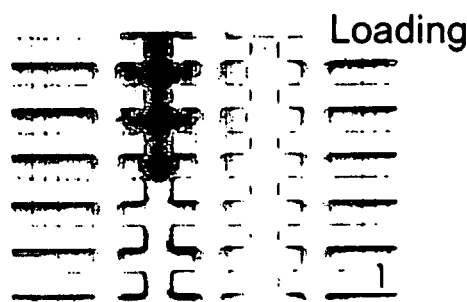
FIGS. 31A–D are a set of optical micrographs showing a portion of the comparator in action.
Figure 31B:
Figure 31C:
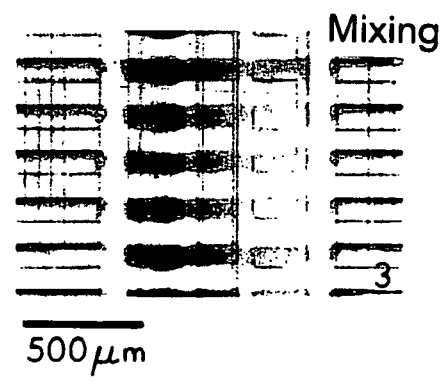
Figure 31D:
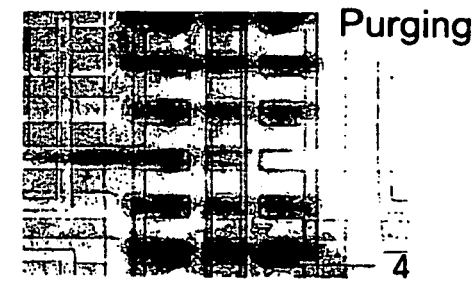

FIG. 30H shows the deactivation of barrier the isolation control line, causing deactivation of the isolation valves, followed by application of pressure to the control line and deactivation of the multiplexor to allow the combined mixture to be recovered.

In the case of the device shown in FIGS. 30A–H, two different reagents can be separately loaded, mixed pair wise, and selectively recovered, making it possible to perform distinct assays in 256 sub-nanoliter reaction chambers and then recover a particularly interesting reagent. The microchannel layout consists of four central columns in the flow layer consisting of 64 chambers per column, with each chamber containing ~750 pL of liquid after compartmentalization and mixing. Liquid is loaded into these columns through two separate inputs under low external pressure (~20 kPa), filling up the array in a serpentine fashion. Barrier valves on the control layer function to isolate the sample fluids from each other and from channel networks on the flow layer used to recover the contents of each individual chamber. These networks function under the control of a multiplexor and several other control valves.

The control channels are first dead end filled with water prior to actuation with pneumatic pressure; the compressed air at the ends of the channels is forced into the bulk porous silicone. This procedure eliminates gas transfer into the flow layer upon valve actuation, as well as evaporation of the liquid contained in the flow layer. The elastomeric valves are analogous to electronic switches, serving as high impedance barriers for fluidic trafficking.

To demonstrate the device plumbing, the fluid input lines were filled with two dyes to illustrate the process of loading, compartmentalization, mixing and purging of the contents of a single chamber within a column.

FIGS. 31A–D show a set of optical micrographs showing a portion of the comparator in action. A subset of the chambers in a single column is being imaged. Elastomeric microvalves enable each of the 256 chamber on the chip to be independently compartmentalized, mixed pairwise, and selectively purged with the blue and yellow solutions. Each of the 256 chambers on the chip can be individually addressed and its respective contents recovered for future analysis using only 18 connections to the outside world, illustrating the integrated nature of the microfluidic circuit.

The large scale integrated microfluidic device of FIG. 30A of FIG. 30 was used as a microfluidic comparator to test for the expression of a particular enzyme. A population of bacteria is loaded into the device, and a fluorogenic substrate system provides an amplified output signal in the form of a fluorescent product. An electronic comparator circuit is designed to provide a large output signal when the input signal exceeds a reference threshold value. An op amp amplifies the input signal relative to the reference, forcing it to be high or low. In the microfluidic comparator structure illustrated in FIG. 30A, the non-fluorescent resorufin derivative, Amplex Red, functions as the reference signal. The input signal consists of a suspension of $E.$ $coli$ expressing recombinant cytochrome c peroxidase (CCP); the enzyme serves as a chemical amplifier in the circuit.

Figure 32A:
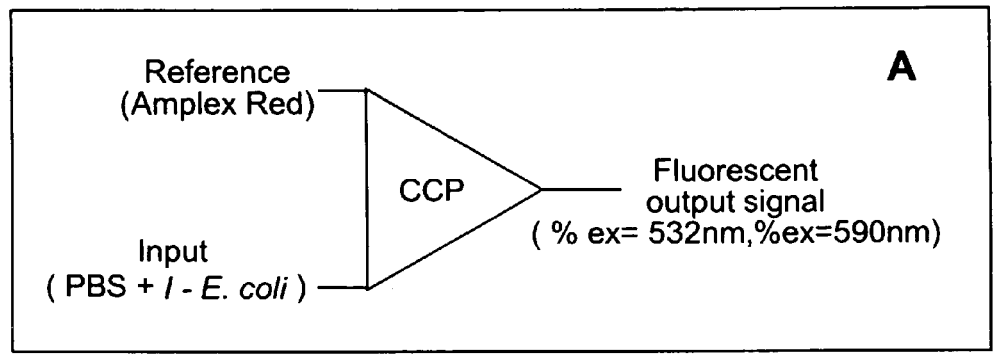
FIG. 32A shows a schematic diagram of the microfluidic comparator logic using and enzyme and fluorogenic substrate.

FIG. 32A shows a schematic diagram of the microfluidic comparator logic using and enzyme and fluorogenic substrate. When a input signal chamber contains cells expressing the enzyme CCP, non-fluorescent Amplex Red is converted to the fluorescent product, resorufin. In the absence of CCP, the output signal remains low.

The cells and substrate are loaded into separate input channels with the central mixing barrier closed in each column and compartmentalized exactly like the procedure illustrated for the blue and orange dyes. The cell dilution (1:1000 of confluent culture) creates a median distribution of ~0.2 cells/compartment, verified by fluorescent microscopy.

The barrier between the substrate and cell sub-compartments is opened for a few minutes to allow substrate to diffuse into the compartments containing the cell mixture. The barrier is then closed to reduce the reaction volume and improve the signal/noise for the reaction.

After a one hour incubation at room temperature, the chip is scanned ($\lambda ex,=532$ nm, $\lambda em=590$ DS 40) with a modified DNA microarray scanner (Axon Industries GenePix 4000B). The presence of one or more CCP expressing cells in an individual chamber produces a strong amplified output signal as Amplex Red is converted to the fluorescent compound resorufin, while the signal in the compartments with no cells remains low.

One example of a scanner for use in detecting signals from LSI microfluidic structure in accordance with the present invention is the Genepix 4000B scanner manufactured by Axon Instruments, Inc. of Union City Calif. The Genepix 4000B was originally designed for DNA array chip scanning. It has two lasers (532/635 mm) that are optimized for Cy3/Cy5 fluorescent dyes respectively. The Genepix normally functions by scanning the bottom surface of a slide coated with Cy3/Cy5 labeled DNA probes sitting on 3-calibrated sapphire mounts. There are, however, several constraints with this scanner that render it less than optimal as a microfluidic chip screener. First, current microfluidic devices used in our experiments are bonded to a 25×25 mm Number 1 coverslip (130–170 um thick). While the laser focal plane can be adjusted through a software interface, it can only penetrate the cover slip to a depth of 50 um, leaving the channels slightly out of focus. However, the resolution obtained is still sufficient for fluorescence measurements within the channel.

A second option being explored is removing the microfluidic chip of the calibrated mounts and seating it in the back of the slide holder. This position places the chip closer to the lens, placing it within the aforementioned software-controlled focal plane range. The disadvantage of this method is that the chip is slightly off normal relative to the laser beams, resulting in an artificial intensity gradient across the chip. This gradient can be compensated for during analysis. Another sub-optimal characteristic of the Genepix scanners is its lack of hardware to stabilize the microfluidic chips when they are connected to several tubing lines. This effect can be successfully compensated for through the addition of weight to the top of the chip. The weight should be non-reflective to prevent scattering of the laser beams that may create artificial noise during the scanning process.

The effect of the hardware focal setting was determined by placing the chip of FIG. 30A filled with Amplex Red solution (neg. control, ~100 µM in the back of the slide holder with a No. 1 cover slip as a spacer. The chip was weighted down and fluorescence was measured consecutively in the same spot with varying focal settings. Readings were taken twice to assess any effect bleaching or light activation of the substrate may have had. Results indicate that fluorescence measurements are somewhat consistent in a range of ±15 µm from optimal focus and then decay rapidly.

Figure 32B:
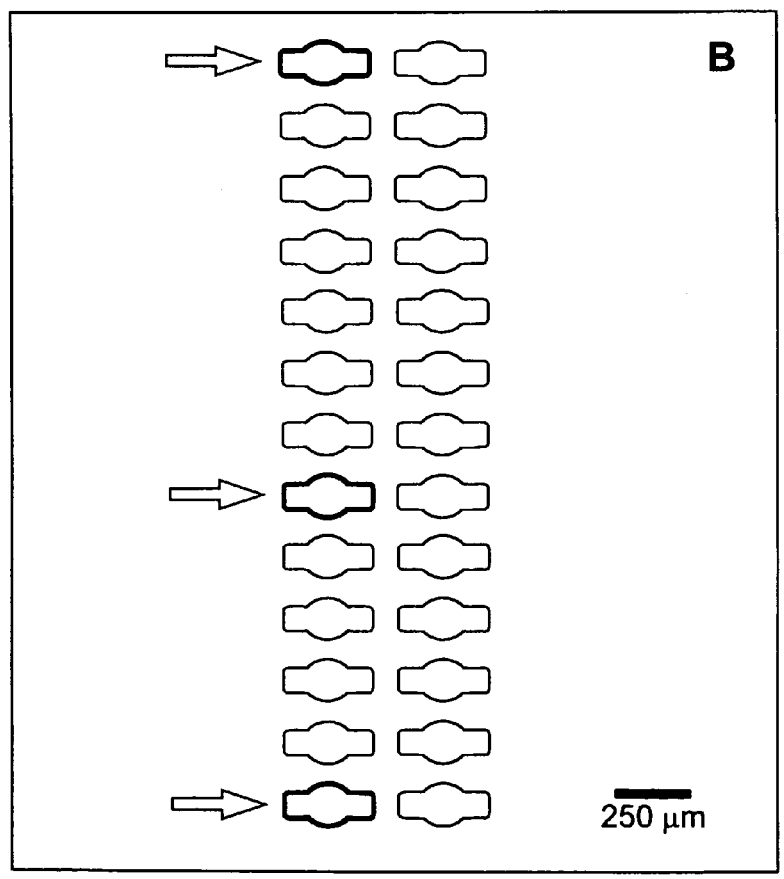
FIG. 32B shows a scanned fluorescence image of the chip in comparator mode.

FIG. 32B shows a scanned fluorescence image of the chip in comparator mode. The left half of column is a dilute solution of CCP expressing $E.$ $coli$ in sterile PBS (137 mM NaCl, 2.68 mM KCl, 10.1 mM Na2HP04, 1.76 mM KH2P04, pH 7.4) after mixing reaction with Amplex Red. Arrows indicate chambers containing single cells. Chambers without cells show low fluorescence. The converted product (resorufin) is clearly visible as green signal. Right half of column is uncatalyzed Amplex Red substrate. To verify that the output signal is a function of CCP activity, a similar experiment was performed using a heterogeneous mixture of $E.$ $coli$ expressing either CCP or enhanced green fluorescent protein (eGFP). The amplified output signal was only dependent on the number of CCP-expressing cells in an individual chamber.

Figure 32C:
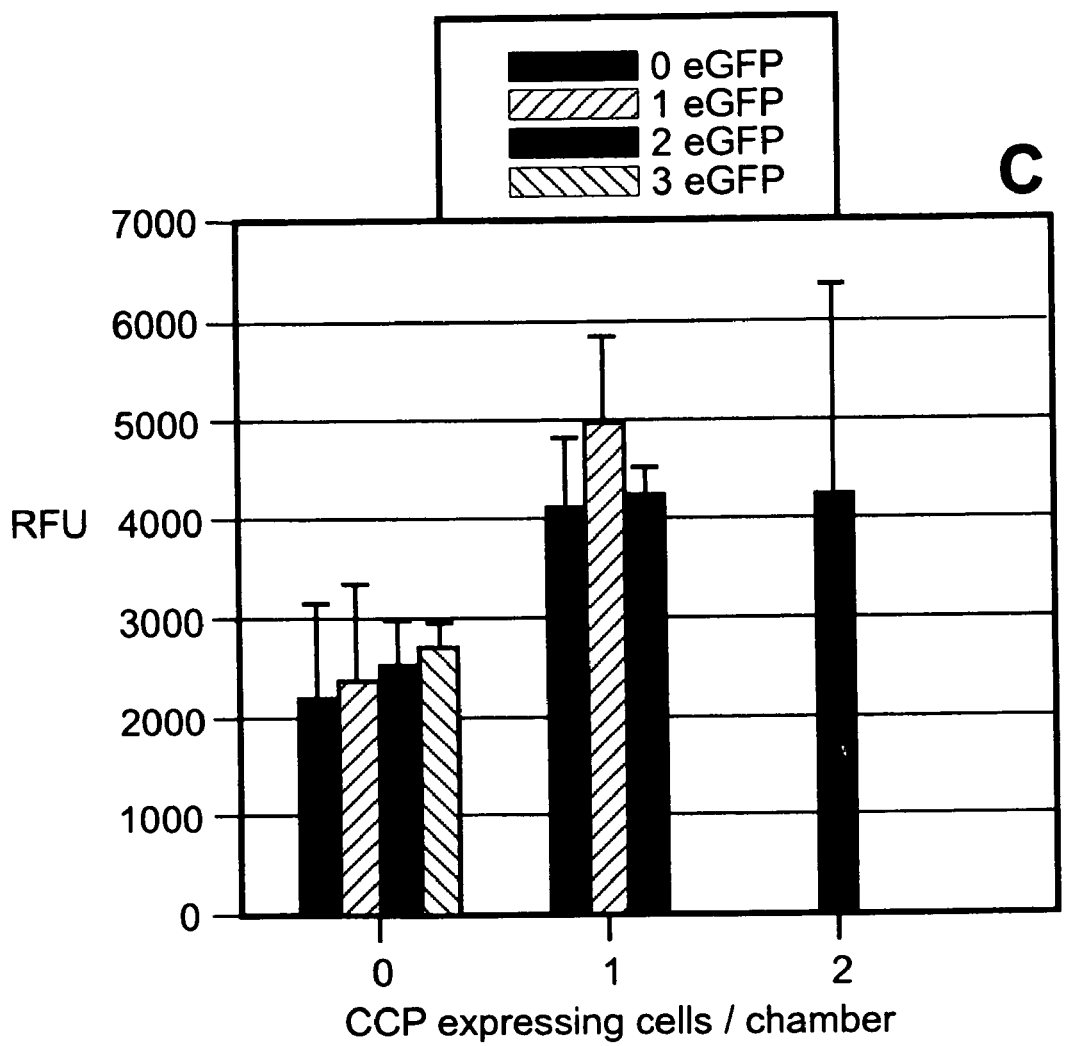
FIG. 32C shows a µHTS comparator and the effect of heterogeneous mixture of eGFP expressing control cells and CCP expressing cells on output signal.

FIG. 32C shows a µHTS comparator and the effect of heterogeneous mixture of eGFP expressing control cells and CCP expressing cells on output signal. The resorufin fluorescence measurement ($\lambda ex=532$ nm, $\lambda em=590$ nm) was made in individual comparator chambers containing $E.$ $coli$ cells expressing either eGFP or CCP. There is a strong increase in signal only when CCP expressing cells are present, with little effect on the signal from eGFP expressing cells. The vertical axis is relative fluorescence units (RFU); error bars represent one standard deviation from the median RFU.

Recovery from the chip can be accomplished by selecting a single chamber, and then purging the contents of a chamber to a collection output. Each column in the chip has a separate output, enabling a chamber from each column to be collected without cross-contamination.

To illustrate the efficacy of the collection process, a dilute phosphate buffered saline (PBS) solution of E. coli expressing GFP was injected into the chip. After compartmentalization approximately every 2nd chamber contained a bacterium. Using an inverted light microscope (Olympus IX50) equipped with a mercury lamp and GFP filter set, single GFP cells were identified with a 20× objective and their respective chambers were purged.

The purged cells were collected from the outputs using polyetheretherketone (PEEK) tubing, which has low cell adhesion properties. Isolations of single GFP-expressing bacteria were confirmed by the visualization of the collected liquid samples under a 40× oil immersion lens using the fluorescence filter set and by observations of single colony growth on Luria-Bertani broth (LB) plates inoculated with the recovered bacteria. Since it has been shown that single molecules of DNA can be effectively manipulated in elastomeric microfluidic devices, it is possible that in future applications individual molecules or molecular clusters will be selected or manipulated in this fashion.

The performance of an electronic comparator is not ideal. For example, there is a finite noise floor, there are absolute voltage and current limitations, there are leakage currents at the inputs, and so forth. Some of these limits result from intrinsic properties of the materials used for the devices, while others depend on either fabrication tolerances or design limitations. The performance of integrated fluidic circuits suffers from similar imperfections.

6. Fabrication Techniques

The storage array and comparator microfluidic devices shown in FIGS. 29A and 30A respectively, were fabricated with multilayer soft lithography techniques using two distinct layers. The "control" layer, which harbors all channels required to actuate the valves, is situated on top of the "flow" layer, which contains the network of channels being controlled. A valve is created where a control channel crosses a flow channel. The resulting thin membrane in the junction between the two channels can be deflected by hydraulic or pneumatic actuation. All biological assays and fluid manipulations are performed on the "flow" layer.

Master molds for the microfluidic channels were made by spin-coating positive photoresist (Shipley SJR 5740) on silicon 9 μm high and patterning them with high resolution (3386 dpi) transparency masks. The channels on the photoresist molds were rounded at 120° C. for 20 minutes to create a geometry that allows full valve closure.

The devices were fabricated by bonding together two layers of two-part cure silicone (Dow Corning Sylgard 184) cast from the photoresist molds. The bottom layer of the device, containing the "flow" channels, is spin-coated with 20:1 part A:B Sylgard at 2500 rpm for 1 minute. The resulting silicone layer is ~30 μm thick. The top layer of the device, containing the "control" channels, is cast as a thick layer (~0.5 cm thick) using 5:1 part A:B Sylgard using a separate mold. The two layers are initially cured for 30 minutes at 80° C.

Control channel interconnect holes are then punched through the thick layer (released from the mold), after which it is sealed, channel side down, on the thin layer, aligning the respective channel networks. Bonding between the assembled layers is accomplished by curing the devices for an additional 45–60 minutes at 80° C. The resulting multilayer devices are cut to size and mounted on RCA cleaned No. 1, 25 mm square glass coverslips, or onto coverslips spin coated with 5:1 part A:B Sylgard at 5000 rpm and cured at 80° C. for 30 minutes, followed by incubation at 80° C. overnight.

Simultaneous addressing of multiple non-contiguous flow channels is accomplished by fabricating control channels of varying width while keeping the dimension of the flow channel fixed (100 μm wide and 9 μm high). The pneumatic pressure in the control channels required to close the flow channels scales with the width of the control channel, making it simple to actuate 100 μm×100 μm valves at relatively low pressures (~40 kPa) without closing off the 50 μm×100 μm crossover regions, which have a higher actuation threshold.

Introduction of fluid into these devices is accomplished through steel pins inserted into holes punched through the silicone. Unlike micromachined devices made out of hard materials with a high Young's modulus, silicone is soft and forms a tight seal around the input pins, readily accepting pressures of up to 300 kPa without leakage. Computer-controlled external solenoid valves allow actuation of multiplexors, which in turn allow complex addressing of a large number of microvalves.

Fluidic circuits fabricated from PDMS will not be compatible with all organic solvents—in particular, flow of a nonpolar solvent may be affected. This issue can be addressed by the use of chemically resistant elastomers. Surface effects due to non-specific adhesion of molecules to the channel walls may be minimized by either passive or chemical modifications to the PDMS surface.

Cross contamination in microfluidic circuits is analogous to leakage currents in an electronic circuit, and is a complex phenomenon. A certain amount of contamination will occur due to diffusion of small molecules through the elastomer itself. This effect is not an impediment with the organic dyes and other small molecules used in the examples in this work, but at some level and performance requirement it may become limiting.

Cross-contamination is also a design issue whose effects can be mitigated by the design of any particular circuit. In the 256 well comparator chip, compensation scheme was introduced by which each of the four columns has a separate output in order to prevent cross contamination during the recovery operation. As fluidic circuit complexity increases, similar design rules will evolve in order to obtain high performance despite the limitations of the particular material and fabrication technology being used.

The computational power of the memory and comparator chips is derived from the ability to integrate and control many fluidic elements on a single chip. For example, the multiplexor component allows specific addressing of an exponentially large number of independent chambers. This permits selective manipulation or recovery of individual samples, an important requirement for high throughput screening and other enrichment applications. It may also be a useful tool for chemical applications involving combinatorial synthesis, where the number of products also grows exponentially.

7. Segmentation Applications

Another example of computational power is the ability to segment a complex or heterogeneous sample into manageable subsamples, which can be analyzed independently as shown in the comparator chip. For example, a large scale integrated microfluidic device such as is shown in FIG. 30A could be utilized to isolate desired component of a heterogeneous mixture. In a first step, the heterogeneous sample could be flowed down one of the serpentine flow channels, with the heterogeneous mixture sufficiently diluted to ensure the presence of no more than one soluble entity between the vertical compartmentalization valves. The flow would then be halted, and the vertical compartmentalization valves actuated to create isolated segments in the serpentine flow channel. Where interrogation/inspection of the various segments indicates the presence of a desired entity within a particular segment, that segment could be purged and the output collected. In the embodiment just described, it is important to note that only one flow channel is utilized, with the other remaining empty or filled with buffer to allow collection of the desired entity absent cross-contamination.

Heterogeneous mixtures susceptible to assaying utilizing large scale integrated microfluidic structures in accordance with embodiments of the present invention can generally be subdivided into two categories. A first category of heterogeneous mixtures comprises particles or molecules. A listing of such particles includes but is not limited to prokaryotic cells, eukaryotic cells, phages/viruses, and beads or other non-biological particles.

One example of such a mixture of particles for assaying is a heterogeneous mixture of bacteria, each harboring a plasmid containing a specific DNA sequence including a gene, a segment of a gene, or some other sequence of interest. The assay could select for the bacteria containing the desired DNA sequence, for example by identifying bacteria harboring the gene encoding a particular enzyme or protein that results in the desired traits.

Another example of a particle mixture for assaying by LSI microfluidic structures in accordance with the present invention comprises a heterogeneous mixture of eukaryotic cells. The assay performed on such a mixture could select a hybridoma cell that expresses a specific antibody.

Still another example of a particle mixture for assaying by LSI microfluidic structures in accordance with the present invention comprises a heterogeneous mixture of phages displaying recombinant protein on their surface. The assay performed on such a mixture could select for the phage that displays the protein with the desired traits.

Yet another example of a particle mixture for assaying by LSI microfluidic structures in accordance with the present invention comprises a heterogeneous mixture of beads, each coated with a single molecule type such as a particular protein, nucleic acid, peptide, or organic molecule. The assay performed on such a mixture could select the bead that is coated with the molecule with the wanted trait.

Large scale integrated microfluidic structures in accordance with embodiments of the present invention can also be utilized to perform assays on heterogenous mixtures of molecules. DNA lends itself to such an approach, due to its inherent capability for amplification utilizing the polymerase chain reaction (PCR) technique. Once amplified, downstream methods may be applied to the DNA, such as in vitro transcription/translation of the amplified template molecule.

One example of such a mixture of molecules for assaying is a heterogeneous mixture of linear or circular templates containing either different genes or clones of the same gene. Following amplification and in vitro transcription/translation, the assay could select for the template whose product (protein) exhibiting desired trait(s).

Another example of a molecular mixture for assaying by LSI microfluidic structures in accordance with the present invention comprises a heterogeneous mixture of linear or circular templates of simply various sequences. The assay could select for the template whose amplified product (DNA) exhibits the desired trait.

Yet another example of a molecular mixture for assaying by LSI microfluidic structures in accordance with the present invention comprises cDNA. An assay could be performed which selects the cDNA clone whose amplified (DNA) or final product (protein/peptide) has the desired traits.

Another example of a molecular mixture for assaying by LSI microfluidic structures in accordance with the present invention comprises a mixture of mRNA. The assay could select the mRNA template whose product (DNA or protein) exhibits the desired trait.

Another example of a molecular mixture for assaying by LSI microfluidic structures in accordance with the present invention comprises genomic DNA. The assay could select the genome or chromosome that exhibits the desired trait, i.e. shows an amplicon of a certain size and/or sequence.

Large scale integrated microfluidic structures in accordance with embodiments of the present invention could also be utilized to perform assays on molecular mixtures comprising other than nucleic acids. For example, molecular mixtures of proteins such as enzymes could be assayed, as these molecules would yield a signal amplification due to turnover of a substrate. The assay could select for the molecule with the desired activity and/or specificity.

The following techniques may be employed to detect the particle or molecule being separated out utilizing a LSI microfluidic structure in accordance with an embodiment of the present invention. Beads, Prokaryotic, and Eukaryotic cells may be detected by either light microscopy or fluorescence. Very small samples such as phages/viruses, non-amplified DNA, protein, and peptides may be detectable utilizing fluorescence techniques. Moreover, the use of micro-electro mechanical (MEMS) techniques may enable the fluorescence of even single molecules to be detected.

A number of assays may be utilized to detect a specific trait of an entity being separated utilizing an LSI microfluidic device in accordance with the present invention. For example, various binding assays may be utilized to detect all combinations between DNA, proteins, and peptides (i.e. protein-protein, DNA-protein, DNA–DNA, protein-peptide etc.). Examples of binding assays include but are not limited to ELISA, FRET, and autoradiography.

Various functional assays may be utilized to detect chemical changes in a target. Examples of such changes detectable by functional assays include but are not limited to, 1) enzymatic turnover of a non-fluorescent substrate to a fluorescent one, 2) enzymatic turnover of a non-chromagenic substrate to a chromagenic one, or from one color to another, 3) enzymatic turnover generating a chemilumiscent signal, and 4) autoradiography.

Homogeneous solutions of various substances may be screened against one another through diffusive mixing. A number of applications are susceptible to these types of assays. One example of such an application is screening cDNA library clones that have been separated for the presence of a specific DNA sequence (i.e. gene) or function. Another example of such an application is screening of chemical libraries including but not limited to peptide libraries, organic molecule libraries, oligomer libraries, and small molecules such as salt solutions. The chemical libraries may be screened for specific functions such as interference with an enzymatic reaction, disrupting specific binding, specific binding, ability to cause crystallization of proteins (small molecule/salt solutions), ability to serve as a substrate.

Other segmentation applications call for subdividing a homogeneous sample into aliquots that can be analyzed separately with independent chemical methods. For example, a large scale integrated microfluidic device such as is shown in FIG. 30 could be utilized to screen these individual entities of a homogenous mixture by exposure to many different reactants. In a first step, the homogenous sample could be flowed through an elongated flow channels. The flow would then be halted, and the vertical compartmentalization valves actuated to create reaction chamber segments isolated from each other. Next, a variety of chemical species differing from each other in identity or concentration could be flowed through a respective flow channel to each of the segments, and then mixed by deactuation of an intervening barrier valve. Observation of a resulting change in the mixture could reveal information about the homogeneous entity.

In a homogeneous segmentation application, it is possible to perform a 1*m screen, i.e. screen one homogeneous solution against 256 others in the structure of FIG. 30A. First, the solution to be assayed is loaded 256 times separate times into the sample input. Next, the chambers are compartmentalized using the sandwich barrier.

Now it is possible to dead end load a different solution into the chambers of the substrate serpentine using the multiplexers. In order to avoid problems with cross contamination and purging and cross contamination, the sandwich barrier could be decoupled into two separate valves, one valve compartmentalizing only the substrate serpentine, and a second valve compartmentalizing the sample serpentine.

By closing both sandwich barriers to compartmentalize both the substrate and sample serpentines, a different solution may be introduced into each of the 256 rows using the multiplexer for fluidic routing. For this purpose, the sample collection ports may be advantageously used fluid introduction instead of the purge input.

Once each of the 256 rows contains a separate homogenous solution, all the barrier valves and the mixing barrier may be closed. This loading is followed by purging either the substrate serpentine or sample serpentine with the solution to be assayed. Decoupling is useful during this step by allowing the substrate serpentine to remain compartmentalized while new fluid may be introduced into the sample serpentine, filling the 256 adjacent chambers with a new homogeneous fluid. By opening the mixing barrier, 256 experiments may be performed by diffusive mixing.

In summary, the devices previously described illustrate that complex fluidic circuits with nearly arbitrary complexity can be fabricated using microfluidic LSI. The rapid, simple fabrication procedure combined with the powerful valve multiplexing can be used to design chips for many applications, ranging from high throughput screening applications to the design of new liquid display technology. Scalability of the process makes it possible to design robust microfluidic devices with even higher densities of functional valve elements.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth. Therefore, many modifications may be made to adapt a particular situation or material to the teachings of the invention without departing from the essential scope and spirit of the present invention. It is intended that the invention not be limited to the particular embodiment disclosed as the best mode contemplated for carrying out this invention, but that the invention will include all embodiments and equivalents falling within the scope of the claims.

What is claimed is:

1. A microfluidic device comprising:
   a microfluidic flow channel formed in a first layer;
   a first microfluidic control channel formed in a second layer adjacent to the first layer, the first microfluidic control channel separated from the microfluidic flow channel by a first deflectable membrane integral with the first layer or the second layer; and
   a second microfluidic control channel adjacent to the first microfluidic control channel and separated from the first microfluidic control channel by a second deflectable membrane.

2. The microfluidic device of claim 1 wherein the first layer underlies the second layer.

3. The microfluidic device of claim 1 wherein the first layer overlies the second layer.

4. The microfluidic device of claim 1 wherein the second microfluidic control channel is formed in a third layer adjacent to the second layer.

5. The microfluidic device of claim 1 wherein:
   the microfluidic flow channel comprises a network of flow channels;
   the first microfluidic control channel comprises a branched network of channels sharing a common inlet and having widened portions; and
   the second microfluidic control channel comprises a network of channels having separate inlets and also having widened portions.

6. The microfluidic device of claim 5 wherein:
   a number of branches of the first control channel network equals a number of the flow channels, each first control channel branch including only one widened portion at a corresponding flow channel branch; and
   the channels of the second control channel network are arranged in a multiplexor configuration, thereby defining an inverse multiplexor structure.

7. The microfluidic device of claim 5 wherein:
   a number of branches of the first control channel network is fewer than a number of the flow channels and have widened portions arranged in a first multiplexor configuration; and
   a number of channels of the second control channel network is fewer than a number of the flow channels and have widened portions arranged in a second multiplexor configuration, thereby defining a cascaded multiplexor structure.

8. The microfluidic device of claim 5 wherein at least one of the first control channel network and the second control channel network comprise a first stage having at least xlogxn control channels, where n is the number of flow channels and x is an integer greater than 2.

9. The microfluidic device of claim 8 wherein the at least one of the first control channel network and the second control channel network further comprises a second stage having at least xlogxn control channels, where n is the number of flow channels and x is an integer greater than 1.

10. The A microfluidic device comprising:
    a microfluidic flow channel formed in a first layer;
    a first microfluidic control channel formed in a second layer adjacent to the first layer, the first microfluidic control channel separated from the microfluidic flow channel by a first deflectable membrane; and
    a second microfluidic control channel adjacent to the first microfluidic control channel and separated from the first microfluidic control channel by a second deflectable membrane, wherein the second microfluidic control channel is formed in the first layer and does not intersect with the microfluidic flow channel.

11. The microfluidic device of claim 10 wherein:
the microfluidic flow channel comprises a network of flow channels;
the first microfluidic control channel comprises a branched network of channels sharing a common inlet and having widened portions; and
the second microfluidic control channel comprises a network of channels having separate inlets and also having widened portions.

12. The microfluidic device of claim 11 wherein:
a number of branches of the first control channel network equals a number of the flow channels, each first control channel branch including only one widened portion at a corresponding flow channel branch; and
the channels of the second control channel network are arranged in a multiplexor configuration, thereby defining an inverse multiplexor structure.

13. The microfluidic device of claim 11 wherein:
a number of branches of the first control channel network is fewer than a number of the flow channels and have widened portions arranged in a first multiplexor configuration; and
a number of channels of the second control channel network is fewer than a number of the flow channels and have widened portions arranged in a second multiplexor configuration, thereby defining a cascaded multiplexor structure.

14. The microfluidic device of claim 11 wherein at least one of the first control channel network and the second control channel network comprise a first stage having at least xlogxn control channels, where n is the number of flow channels and x is an integer greater than 2.

15. The microfluidic device of claim 14 wherein the at least one of the first control channel network and the second control channel network further comprises a second stage having at least xlogxn control channels, where n is the number of flow channels and x is an integer greater than 1.

16. A microfluidic device comprising:
a microfluidic flow channel formed in a first layer;
a first microfluidic control channel formed in a second layer adjacent to the first layer, the first microfluidic control channel separated from the microfluidic flow channel by a first deflectable membrane;
a second microfluidic control channel adjacent to the first microfluidic control channel and separated from the first microfluidic control channel by a second deflectable membrane; and
a third microfluidic control channel adjacent to the second microfluidic control channel and separated from the second microfluidic control channel by a third deflectable membrane.

17. The microfluidic device of claim 16 wherein:
the first microfluidic flow channel comprises a network of flow channels;
the first microfluidic control channel comprises a first branched network of channels sharing a first common inlet and having widened portions;
the second microfluidic control channel comprises a second branched network of channels sharing a second common inlet and also having widened portions; and
the third microfluidic control channel comprises a network of channels having separate inlets and also having widened portions.

18. The microfluidic device of claim 17 wherein:
a number of branches of the first control channel network equals a number of the flow channels, each first control channel branch including only one widened portion at a corresponding flow channel branch; and
the channels of the second control channel network are arranged in a multiplexor configuration, thereby defining an inverse multiplexor structure.

19. The microfluidic device of claim 17 wherein:
a number of branches of the first control channel network is fewer than a number of the flow channels and have widened portions arranged in a first multiplexor configuration; and
a number of channels of the second control channel network is fewer than a number of the flow channels and have widened portions arranged in a second multiplexor configuration, thereby defining a cascaded multiplexor structure.

20. The microfluidic device of claim 17 wherein at least one of the first control channel network, the second control channel network, and the third control channel network comprise a first stage having at least xlogxn control channels, where n is the number of flow channels and x is an integer greater than 2.

21. The microfluidic device of claim 20 wherein the at least one of the first control channel network, the second control channel network, and the third control channel network further comprises a second stage having at least xlogxn control channels, where n is the number of flow channels and x is an integer greater than 1.

* * * * *